(12) United States Patent
Martin et al.

(10) Patent No.: US 11,944,671 B2
(45) Date of Patent: Apr. 2, 2024

(54) HIPPO PATHWAY DEFICIENCY REVERSES SYSTOLIC HEART FAILURE POST-INFARCTION

(71) Applicant: Baylor College of Medicine, Houston, TX (US)

(72) Inventors: James F. Martin, Pearland, TX (US); John Leach, Houston, TX (US)

(73) Assignee: BAYLOR COLLEGE OF MEDICINE, Houston, TX (US)

( * ) Notice: Subject to any disclaimer, the term of this patent is extended or adjusted under 35 U.S.C. 154(b) by 587 days.

(21) Appl. No.: 16/644,435

(22) PCT Filed: Sep. 6, 2018

(86) PCT No.: PCT/US2018/049792
§ 371 (c)(1),
(2) Date: Mar. 4, 2020

(87) PCT Pub. No.: WO2019/051117
PCT Pub. Date: Mar. 14, 2019

(65) Prior Publication Data
US 2020/0206327 A1    Jul. 2, 2020

Related U.S. Application Data

(60) Provisional application No. 62/554,627, filed on Sep. 6, 2017.

(51) Int. Cl.
*A61K 38/53* (2006.01)
*A61K 31/7105* (2006.01)
(Continued)

(52) U.S. Cl.
CPC .......... *A61K 38/53* (2013.01); *A61K 31/7105* (2013.01); *A61P 9/04* (2018.01);
(Continued)

(58) Field of Classification Search
CPC ....... A61K 38/53; A61K 31/7105; A61P 9/04; C07K 16/18; C12N 15/113; C12N 2310/531
See application file for complete search history.

(56) References Cited

U.S. PATENT DOCUMENTS

2005/0246794 A1 * 11/2005 Khvorova .......... C12N 15/1138
536/23.1
2012/0277286 A1    11/2012 Youle et al.

OTHER PUBLICATIONS

Heallen et al., "Hippo signaling impedes adult heart regeneration", Development, vol. 140, No. 23, Jan. 1, 2013 (Jan. 1, 2013), pp. 4683-4690.
(Continued)

*Primary Examiner* — Terra C Gibbs
(74) *Attorney, Agent, or Firm* — Norton Rose Fulbright US LLP

(57) ABSTRACT

Embodiments of the disclosure include methods and compositions related to treating or reducing the severity or delaying the onset of one or more cardiac conditions in a mammal. In particular embodiments, the compositions concern Park2 and its use for a cardiac medical condition. In specific cases, effective amounts of Park2 polynucleotide(s) and/or Park2 polypeptide(s) are provided to an individual in need thereof, including for heart failure, for example. The administration may be locally to the heart, for example.

9 Claims, 71 Drawing Sheets
Specification includes a Sequence Listing.

(51) Int. Cl.
*A61P 9/04* (2006.01)
*C07K 16/18* (2006.01)
*C12N 15/113* (2010.01)
*A61K 45/06* (2006.01)

(52) U.S. Cl.
CPC ............ *C07K 16/18* (2013.01); *C12N 15/113* (2013.01); *A61K 45/06* (2013.01); *C12N 2310/531* (2013.01)

(56) References Cited

OTHER PUBLICATIONS

Kubli et al., "Parkin Protein Deficiency Exacerbates Cardiac Injury and Reduces Survival following Myocardial Infarction", Journal of Biological Chemistry, vol. 288, No. 2, Jan. 1, 2013 (Jan. 1, 2013), pp. 915-926.
Marin-Garcia et al., "The Mitochondrial Organelle and the Heart" Rev Esp Cardiel, Dec. 2002 (Dec. 2002), vol. 55, No. 12, p. 1293-1310.

\* cited by examiner

FIG. 13a
FIG. 13b
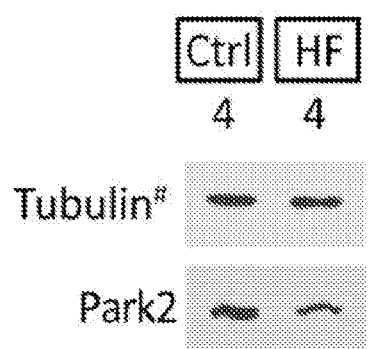
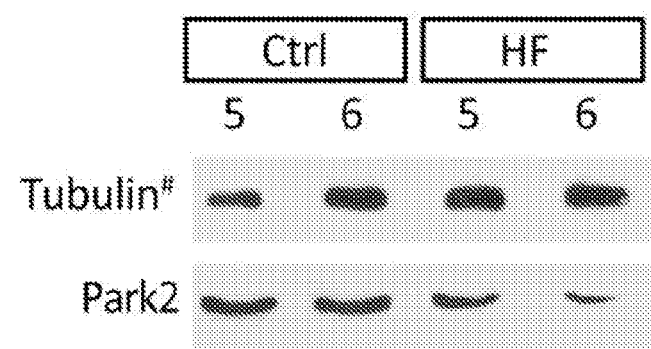
FIG. 13c
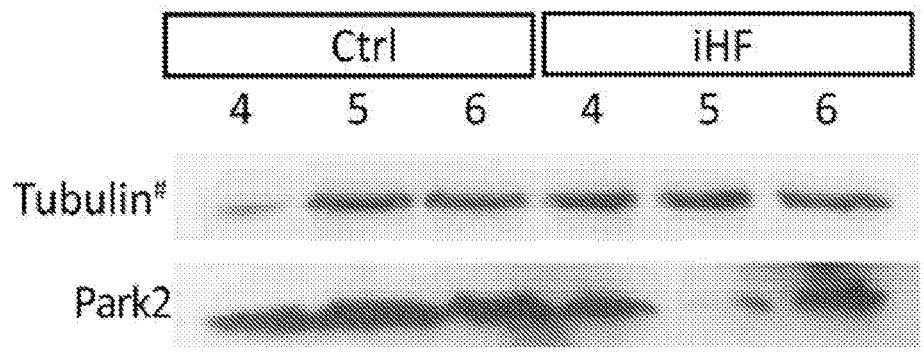

Ctrl (Park2 +/+)
Minimal Scar
Normal Function

Park2 (-/-)
Fibrotic Scar
Reduced Function

HIPPO PATHWAY DEFICIENCY REVERSES SYSTOLIC HEART FAILURE POST-INFARCTION

CROSS-REFERENCE TO RELATED APPLICATION

This application is a national phase application under 35 U.S.C. § 371 that claims priority to International Application No. PCT/US2018/049792 filed Sep. 6, 2018, which claims the benefit of U.S. Provisional Patent Application No. 62/554,627, filed Sep. 6, 2017, all of which are incorporated by reference herein in their entirety for all purposes.

STATEMENT REGARDING FEDERALLY SPONSORED RESEARCH OR DEVELOPMENT

This invention was made with government support under HL127717 and HL118761 awarded by the National Institutes of Health. The government has certain rights in the invention.

SEQUENCE LISTING

The instant application contains a Sequence Listing which has been filed electronically in ASCII format and is hereby incorporated by reference in its entirety. Said ASCII copy, created on Mar. 12, 2020, is named BAYM_P0240US_1001116313_SL.txt and is 14,137 bytes in size.

TECHNICAL FIELD

Embodiments of the disclosure concern at least the fields of cell biology, molecular biology, cardiology, physiology, biochemistry, and medicine.

BACKGROUND

Heart failure, the inability of the heart to pump blood, has no definitive treatment except heart transplantation or ventricular assist devices (Lopez et al., 2006). In heart failure, physiological compensatory mechanisms place strain on cardiomyocytes and promote cardiomyocyte loss and fibrosis in pathological remodelling (Lenneman and Birks, 2014; Braunwald, 2013; Birks, 2013). Hippo pathway activation, including the Mst and Lats kinases and Salv adaptor, results in phosphorylation and nuclear exclusion of transcriptional cofactors Yap and Taz that cooperatively bind DNA with Tead factors (Halder and Johnson, 2011; Halder et al., 2012). Concurrent Salv or Lats1 and Lats2 deletion with myocardial infarct improves heart function (Heallen et al., 2013; Morikawa et al., 2015; Tao et al., 2016). Yap target genes control proliferation, cytoskeletal remodelling, and protect the plasma membrane from contractile stress (Morikawa et al., 2015). Maladaptive activation of Hippo signalling occurs in human heart failure and mouse ischaemia reperfusion (Matsuda et al., 2016; Del Re et al., 2014).

The present disclosure provides solutions to long-felt needs in the art of providing effective therapy for cardiac conditions.

BRIEF SUMMARY

Embodiments of the disclosure encompass methods and compositions for treatment of a cardiac condition in an individual in need thereof. The cardiac condition may be of any kind and may or may not be congenital. The condition may be one that would benefit from having regeneration/renewal of cardiomyocytes. The individual may be of any kind, including mammals, such as humans, dogs, cats, horses, and so forth. The individual may be of any race or gender. In some cases, the individual is diagnosed as having a cardiac condition or is suspected of having a cardiac condition or is at risk for having a cardiac condition compared to the general population.

In particular embodiments, one or more compositions are provided to an individual for treatment of a cardiac condition or risk or susceptibility thereof. The composition may or may not be provided to the individual more than once. The composition may be nucleic acid or peptide or protein, in at least some cases.

In specific embodiments, there are methods of reversing damage (such as muscle loss and/or muscle damage) in an individual after a cardiac event, such as infarction, by promoting cardiomyocyte regeneration/renewal.

In particular embodiments, the methods and compositions comprise administering Park2 polynucleotide(s) and/or Park2 polypeptide(s) to an individual that has a cardiac condition or is suspected of having a cardiac condition or is at risk for having a cardiac condition.

In some embodiments, there is a method of treating an individual for a cardiac condition (cardiovascular disease, cardiomyopathy, heart failure, myocardial infarction, ischemia, necrosis, fibrosis, Duchenne muscular dystrophy, diabetic cardiomyopathy, age-related cardiomyopathy, and other degenerative conditions, for example), comprising the step of providing an effective amount of a Park2 nucleic acid composition and/or Park2 polypeptide composition to the individual. The cardiac condition in the individual causes the individual to be in need of cardiomyocyte renewal, in specific embodiments. The heart of the individual may have cardiomyocyte apoptosis, necrosis, and/or autophagy, in particular embodiments.

The composition may be provided to the individual once or more than once. The composition may be provided to the individual systemically, locally (including to the heart), or both.

In some embodiments the methods further comprise providing to the individual an effective amount of an agent that targets Salvador (Salv) nucleic acid or protein, such as a shRNA and/or an antibody. Any individual may be provided an additional therapy for the cardiac condition.

The foregoing has outlined rather broadly the features and technical advantages of the embodiments of the present disclosure in order that the detailed description that follows may be better understood. Additional features and advantages will be described hereinafter which form the subject of the claims herein. It should be appreciated by those skilled in the art that the conception and specific embodiments disclosed may be readily utilized as a basis for modifying or designing other structures for carrying out the same purposes of the present designs. It should also be realized by those skilled in the art that such equivalent constructions do not depart from the spirit and scope as set forth in the appended claims. The novel features which are believed to be characteristic of the designs disclosed herein, both as to the organization and method of operation, together with further objects and advantages will be better understood from the following description when considered in connection with the accompanying figures. It is to be expressly understood, however, that each of the figures is provided for

BRIEF DESCRIPTION OF THE DRAWINGS

For a more complete understanding of the present disclosure, reference is now made to the following descriptions taken in conjunction with the accompanying drawings.

FIGS. 3a-3m. SalvCKO mice activate reparative molecular response to heart failure. 3a, Total-RNA-seq diagram. 3b, Volcano plot total-RNA-seq: SalvCKO myocardial infarction, control myocardial infarction (n=3 per group). 3c, 3d, Gene ontology (GO) total-RNA-seq: SalvCKO MI, control myocardial infarction (n=3 per group). 3e, TRAP RNA-seq (TRAP-seq) diagram. 3f, Volcano plot TRAP-seq: SalvCKO MI, control myocardial infarction (n=3 per group). 3g, Sample distance matrix: total-RNA-seq, TRAP-seq (n=3 per group). 3h, Fold change TRAP/total RNA (n=3 per group) cardiomyocyte, non-cardiomyocyte-enriched genes (Gene Expression Omnibus accession number GSE49906), t-test, ***P<0.001. 3i, Cardiomyocyte transcripts TRAP-seq enriched; non-cardiomyocyte and non-coding RNA transcripts total-RNA-seq enriched (n=3 per group). 3j, PCA total and TRAP-seq (n=3 per group). 3k, 3l, GO TRAP-seq: SalvCKO myocardial infarction versus control myocardial infarction (n=3 per group). 3m, Normalized Park2 read counts, n=3 per group. Control: tamoxifen-injected αMHC-mcm; Rpl22$^{HA}$. SalvCKO: tamoxifen-injected αMHC-mcm; Rpl22$^{HA}$; Salv$^{fl/fl}$.

Figure 1A:
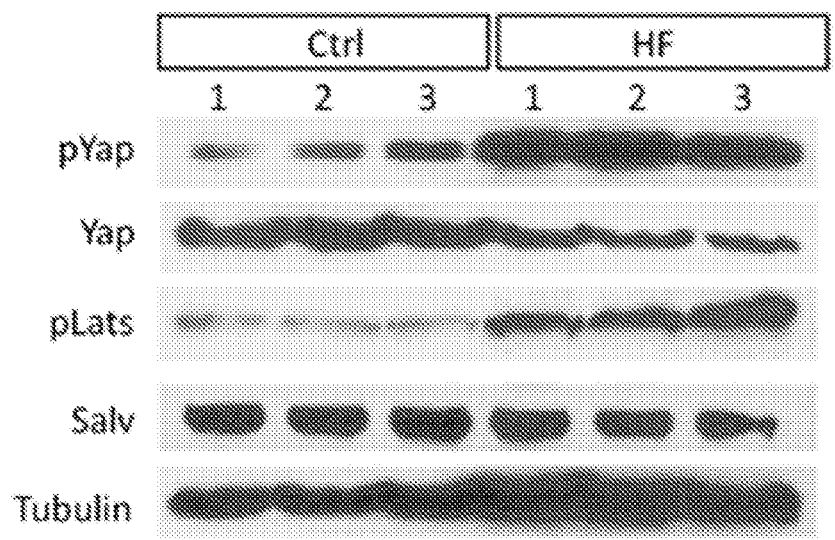
FIGS. 1a-1f. Activated Hippo signalling in human heart failure. 1a, 1b, Western blots of human heart samples. Ctrl: non-failing, non-transplantable, n=6; HF: non-ischaemic idiopathic end-stage cardiomyopathy, n=6; iHF: ischaemic end-stage heart failure, n=6. Additional samples FIG. 5. 1c-1f, Quantification Yap (1c), pYap (1d), pLats (1e), Salv (1f). Mann-Whitney U-test. Data are mean±s.e.m., P>0.05 non-significant (NS), *P<0.05, P<0.01, *P<0.001.
Figure 1B:
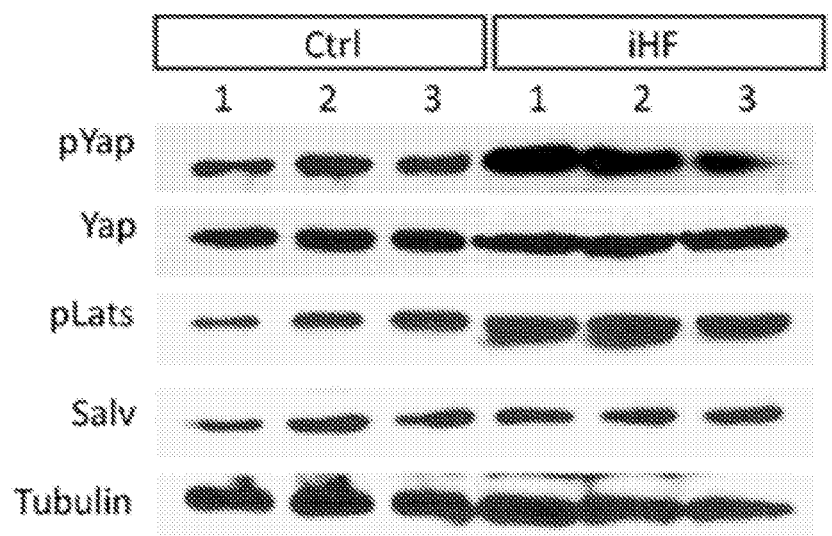
Figure 1C:
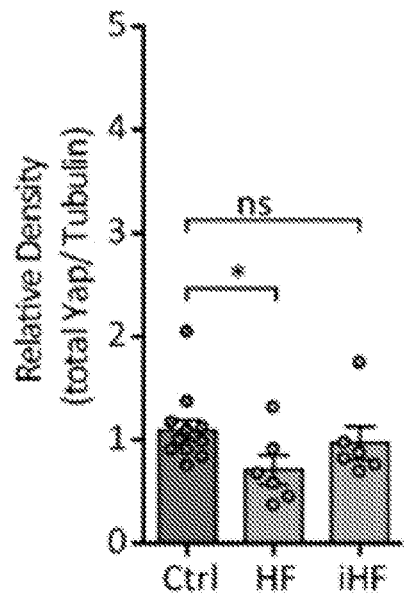
Figure 1D:
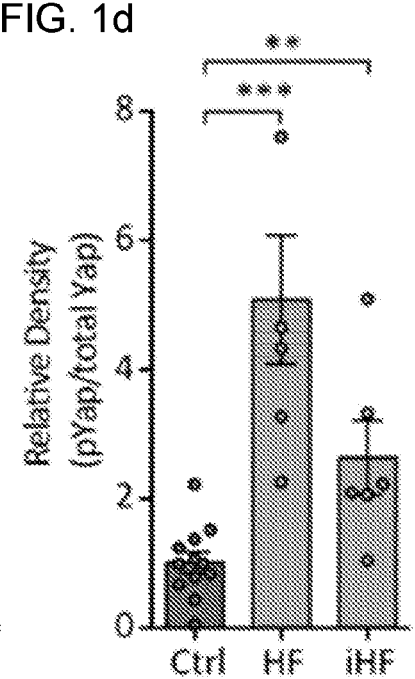
Figure 1E:
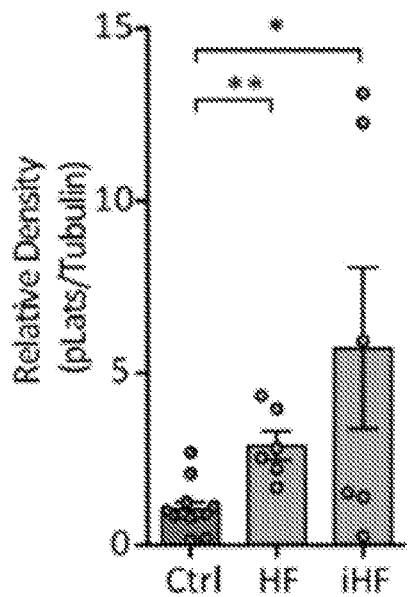
Figure 1F:
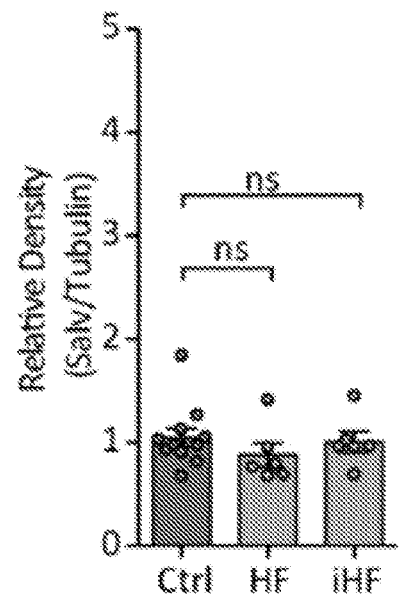

FIGS. 10a-10f. Vessel growth in the border zone of Hippo-deficient mouse hearts. 10a, qPCR of known markers of heart failure at 6 weeks after myocardial infarction; myosin heavy chain 6 (Myh6), myosin heavy chain 7 (Myh7), natriuretic peptide A (Nppa), natriuretic peptide B (Nppb), n=3 per group; ANOVA, Bonferroni's post-hoc test. 10b, Masson's trichrome (scale bar, 100 µm) and immunofluorescence staining for isolectin B4 (scale bar, 25 µm) and CD31 (scale bar, 25 µm), control (n=3) SalvCKO (n=5). 10c-10e, Quantification 9 weeks after myocardial infarction in the border zone for capillary density (c), isolectin+vessels (10d), and CD31+ cells (10e), control (n=3) SalvCKO (n=5), Mann-Whitney U-test. 10f, qPCR of angiogenic growth factors, cardiomyocyte-specific TRAP RNA, 6 weeks after myocardial infarction, Angiopoietin 1 (Angpt1) and 2 (Angpt2), fibroblast growth factor 14 (Fgf14) and 18 (Fgf18), vascular endothelial growth factor B (Vegfb) and C (Vegfc), n=3 per group; ANOVA, Bonferroni's post-hoc test. Data are mean±s.e.m., P>0.05 non-significant (NS), *P<0.05, P<0.01,*P<0.001.

FIGS. 11a-11d. TRAP RNA sequencing reproducibility. 11a, Reproducibility correlation matrices of the RNA-seq read count, linear regression, n=3 per group. 11b, 11c, Plot of the per-gene s.d. across samples, against the rank (mean) and read count, variance stabilizing transformation, total-RNA-seq (11b), and Trap RNA-seq (11c). 11d, $\log_2$(fold change) between Trap and total-RNA-seq for control myocardial infarction and SalvCKO myocardial infarction was highly correlated.

FIGS. 12a-12g. A reparative molecular response to heart failure in Hippo-deficient hearts. 12a, Gene lists of the top 10 genes with the highest fold change in each GO category for total RNA: SalvCKO myocardial infarction versus control myocardial infarction. 12b, Boxplot of the normalized read count for Tnnt2, Cdh5, and Malat1. Error bars, s.e.m. c, Volcano plot TRAP-seq: control myocardial infarction versus control sham. 12d, 12e, GO upregulated (12d) and downregulated (12e) genes. 12f, 12g, Gene lists of the top ten genes with the highest fold change in each GO category for Trap RNA: control myocardial infarction versus control sham (12f); Trap RNA: SalvCKO myocardial infarction versus control myocardial infarction (12g).

FIGS. 13a-13i. Requirement of Park2 in the regenerating mouse heart. 13a-13c, Human heart western blots; quantification presented in FIG. 4, tubulin blot is repeated from FIG. 5. 13d, Scar size 21 days after myocardial infarction in P1 Park2 wild-type (+/+) and null (−/−) mice; Mann-Whitney U-test. 13e, 13f, Echocardiography: ejection fraction (EF) (13e), and fractional shortening (FS) (13f); ANOVA, Bonferroni's post-hoc test. 13g, Cardiomyocyte cell size measured by cross-sectional area, mean (red dashed line), t-test. 13h, Masson's trichrome, 21 days after myocardial infarction in P1 Park2 wild type (+/+) (n=8) and null (−/−) (n=4) mice; scale bar, 2 mm. 13i, Summary of results indicating Park2 is necessary for cardiac regeneration. Data are mean±s.e.m., P>0.05 non-significant (NS), *P<0.05, P<0.01, *P<0.001.

FIGS. 14a-14g. Requirement of Park2 in the P8 Hippo-deficient regenerating mouse heart. 14a, Mitochondrial DNA content 4 days after myocardial infarction in P8 control and SalvCKO (n=3 per group). 14b, Park2 protein levels in border zone (BZ) and distal zone (DZ) myocardium at 4 days after myocardial infarction in P8 control and SalvCKO (n=3 per group). 14c, Scar size 21 days after myocardial infarction in P8 Park2 wild type (+/+) and mutant (mut; −/− or +/−) mice, in combination with Salv CKO; ANOVA, Bonferroni's post-hoc test. 14d, 14e, Echocardiography: ejection fraction (EF) (14d) and fractional shortening (FS) (e); ANOVA, Bonferroni's post-hoc test. 14f, Masson's trichrome, 21 days after myocardial infarction in P8 Park2 mutant (n=20) and Salv CKO; Park2 double-mutant mice (n=15); scale bar, 2 mm. 14g, Summary of results indicating Park2 is necessary for regeneration. Data are mean±s.e.m., P>0.05 non-significant (NS), *P<0.05, P<0.01, *P<0.001.

DETAILED DESCRIPTION

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

As used herein, the term "nucleotide sequence" refers to a polymer of DNA or RNA which can be single-stranded or double-stranded, optionally containing synthetic, non-natural or altered nucleotide bases capable of incorporation into DNA or RNA polymers. The term "polynucleotide" is used interchangeably with the term "oligonucleotide." The term "nucleotide sequence" is interchangeable with "nucleic acid sequence" unless otherwise clearly stated. "Nucleotide sequence" and "nucleic acid sequence" are terms referring to a sequence of nucleotides in a polynucleotide molecule.

As used herein, the term "operably-linked" refers to the association of nucleic acid sequences on a polynucleotide so that the function of one of the sequences is affected by another. For example, a regulatory DNA sequence is said to be "operably linked to" a DNA sequence that codes for an RNA ("an RNA coding sequence" or "shRNA encoding sequence") or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation. An RNA coding sequence refers to a nucleic acid that can serve as a template for synthesis of an RNA molecule such as an siRNA and an shRNA. Preferably, the RNA coding region is a DNA sequence.

As used herein, the term "pharmaceutically acceptable" is a carrier, diluent, excipient, and/or salt that is compatible with the other ingredients of the formulation, and not deleterious to the recipient thereof. The active ingredient for administration may be present as a powder or as granules; as a solution, a suspension or an emulsion or as described elsewhere throughout the specification.

As used herein, the term "promoter" refers to a nucleotide sequence, usually upstream (5') to its coding sequence, which directs and/or controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence that stimulates promoter activity and may be an innate element of the promoter or a heterologous element inserted to enhance the level or tissue specificity of a promoter. It is capable of operating in both orientations (sense or antisense), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions. Any promoter known in the art which regulates the expression of the shRNA or RNA coding sequence is envisioned in the practice of methods encompassed by the disclosure. In specific embodiments, the promoter is tissue-specific promoter, such as one that is effective in the heart muscle. Examples of cardiac-specific promoters include Cardiac Troponin T promoter (Iannello and Ordahl, 1991), for example.

As used herein, the term "treating" refers to ameliorating at least one symptom of, curing and/or preventing the development of a disease or disorder such as for example, but not limited to, ischemic heart disease, heart failure, cardiomyopathy, etc.

As used herein, the term "vector" refers to any viral or non-viral vector, as well as any plasmid, cosmid, phage or binary vector in double or single stranded linear or circular form that may or may not be self-transmissible or mobilizable, and that can transform prokaryotic or eukaryotic host cells either by integration into the cellular genome or which can exist extrachromosomally (e.g., autonomous replicating plasmid with an origin of replication). Any vector known in the art is envisioned for use in the practice of this disclosure. Examples of viral vectors include retroviral, lentiviral, adenoviral, adeno-associated viral, and so forth.

I. General Embodiments

Mammalian organs vary widely in regenerative capacity. Poorly regenerative organs, such as the heart, are particularly vulnerable to organ failure. Once established, heart failure commonly results in mortality (Loehr et al., 2008). The Hippo pathway, a kinase cascade that prevents adult cardiomyocyte proliferation and regeneration (Halder and Johnson, 2011) is upregulated in human heart failure. The present disclosure shows that deletion of the Hippo pathway component Salvador (Salv) in mouse hearts with established ischaemic heart failure after myocardial infarction induces a reparative genetic program with increased scar border vascularity, reduced fibrosis, and recovery of pumping function compared with controls. Using translating ribosomal affinity purification, the inventors isolated cardiomyocyte-specific translating messenger RNA. Hippo-deficient cardiomyocytes have increased expression of proliferative genes and stress response genes, such as the mitochondrial quality control gene, Park2. Genetic studies indicate that Park2 is useful for heart repair, indicating at least in certain embodiments benefit for mitochondrial quality control in regenerating myocardium. It was established that gene therapy with a virus encoding Salv short hairpin RNA improves heart function when delivered at the time of infarct or after ischaemic heart failure following myocardial infarction. The findings indicate that the failing heart has a previously unrecognized reparative capacity involving more than cardiomyocyte renewal/regeneration.

In some embodiments, the methods and compositions encompass Park2 polynucleotides and/or polypeptides for heart repair at the time of a cardiac event (such as infarct) and/or after the event. In certain embodiments, delivery of one or more Park2 polynucleotides and/or polypeptides to an individual prior to a cardiac event delays its onset, reduces its severity, ameliorates one or more symptoms associated with the event, prevents mortality of the individual, and so forth.

II. Compositions

Embodiments of the disclosure encompass one or more compositions suitable for an individual with a cardiac condition of any kind. The compositions may be formulated for use for treatment of the cardiac condition(s). In specific embodiments the compositions are comprised of nucleic acid(s) or polypeptide(s). Embodiments of the disclosure encompass mixtures of compositions, including mixtures of compositions of the disclosure with one or more other compositions not described herein.

In particular embodiments, the composition(s) of the disclosure encompass Park2 polynucleotides and/or Park2 polypeptides. The skilled artisan recognizes that other names for the encoded gene product or the gene includes PRKN, parkin RBR E3 ubiquitin protein ligase, AR-JP, LPRS2, PDJ, and PARK2. The Park2 composition(s) may be mammalian polynucleotides and/or polypeptides, for example, including human or murine or from rat, in at least some cases.

In particular embodiments, there are one or more nucleic acids that express Park2 such that upon delivery to an individual the levels of Park2 polynucleotides and/or polypeptides at the site of delivery are detectably increased compared to in the absence of providing of the nucleic acids. The nucleic acids may be DNA or RNA, for example. Upon administration of Park2 polypeptide(s) to an individual, the level of Park2 polypeptides may detectably increase at the site of delivery.

Examples of Park2 polynucleotides and polypeptides are known in the art. However, one example of a Park2 polypeptide is of the following sequence, obtained from National Center for Biotechnology Information's (NCBI) GenBank® database, Accession No. AAH22014:

```
                                                              (SEQ ID NO: 25)
  1 mivfvrfnss hgfpvevdsd tsifqlkevv akrqgvpadq lrvifagkel rndwtvqncd 61 ldqqsivhiv qrpwrkgqem natggddprn aaggcerepq sltrvdlsss vlpgdsvgla 121 vilhtdsrkd sppagspagr siynsfyvyc kgpcqrvqpg klrvqcstcr qatltltqgp 181 scwddvlipn rmsgecqsph cpgtsaefff kcgahptsdk etsvalhlia tnsrnitcit 241 ctdvrspvlv fqcnsrhvic ldcfhlycvt rlndrqfvhd pqlgyslpcv gtgdtvvlrg 301 alggfrrgva gcpnslikel hhfrilgeeq ynryqqygae ecvlqmggvl cprpgcgagl 361 lpepdqrkvt ceggnglgcg ygqrrtk
```

One example of a Park2 polynucleotide is of the following sequence, obtained from NCBI GenBank database, Accession No. BC022014.

```
                                                              (SEQ ID NO: 26)
   1 gggatttaac ccaggagagc cgctggtggg aggcgcggct ggcgccgctg cgcgcatggg 61 cctgttcctg gcccgcagcc gccacctacc cagtgaccat gatagtgttt gtcaggttca 121 actccagcca tggtttccca gtggaggtcg attctgacac cagcatcttc cagctcaagg 181 aggtggttgc taagcgacag ggggttccgg ctgaccagtt gcgtgtgatt ttcgcaggga 241 aggagctgag gaatgactgg actgtgcaga attgtgacct ggatcagcag agcattgttc 301 acattgtgca gagaccgtgg agaaaaggtc aagaaatgaa tgcaactgga ggcgacgacc 361 ccagaaacgc ggcgggaggc tgtgagcggg agccccagag cttgactcgg gtggacctca 421 gcagctcagt cctcccagga gactctgtgg ggctggctgt cattctgcac actgacagca 481 ggaaggactc accaccagct ggaagtccag caggtagatc aatctacaac agcttttatg 541 tgtattgtaa aggcccctgt caaagagtgc agccggggaa actcagggta cagtgcagca 601 cctgcaggca ggcaacgctc accttgaccc agggtccatc ttgctgggat gatgttttaa 661 ttccaaaccg gatgagtggt gaatgccaat ccccacactg ccctgggact agtgcagaat 721 ttttctttaa atgtggagca caccccacct ctgacaagga aacatcagta gctttgcacc 781 tgatcgcaac aaatagtcgg aacatcactt gcattacgtg cacagacgtc aggagccccg 841 tcctggtttt ccagtgcaac tcccgccacg tgatttgctt agactgtttc cacttatact 901 gtgtgacaag actcaatgat cggcagtttg ttcacgaccc tcaacttggc tactccctgc 961 cttgtgtggg aactggagac acagtggtgc ttagaggagc tctgggggga ttcaggagag 1021 gagtcgctgg ctgtcccaac tccttgatta agagctcca tcacttcagg attctgggag 1081 aagagcagta caaccggtac cagcagtatg gtgcagagga gtgtgtcctg cagatggggg 1141 gcgtgttatg ccccgccct ggctgtggag cggggctgct gccggagcct gaccagagga 1201 aagtcacctg cgaaggggc aatggcctgg gctgtgggta tggacaacga agaacaaaat 1261 aagctgcctc agggagaagt gagtgcctca ttcaatacat cgttcaagga aaagtcattg 1321 gtagcaaagc tatagaagaa ttacagagtt ccagatgtgg aaaaagccct agacgtcatt 1381 aactccagtg attatcagga tgtggttcac agatttattg taagatgcct gtgaattcac 1441 ccgtgcttaa ttttttttttc cctcaattat caagatagaa aaagtacaac tcttaccatg 1501 tgggtatgca agaaatgtta gctgttacaa aaaaaatcgc gtataaaaaa gttgaaaacc 1561 aaataaaaaa aaaaa
```

Embodiments of Park2 polypeptides and Park2 polynucleotides include functional derivatives or functional fragments thereof, and the derivative or fragment may be considered functional if it has the ability to improve at least one symptom (or has the ability to regenerate cardiomyocytes when provided in an effective amount, for example. Such an activity may be measured by any suitable means. In particular embodiments, one can assess functional activity by assaying for reduction in the severity of a symptom, for example. In specific embodiments, the Park2 or functional fragment or functional derivative is soluble. The Park2 or functional fragment or functional derivative may be comprised in a fusion protein, for example with a tag or label.

Park2 proteinaceous compositions may be made by any technique known to those of skill in the art, including, for example, the expression of proteins, polypeptides or peptides through standard molecular biological techniques, the isolation of proteinaceous compounds from natural sources, or the chemical synthesis of proteinaceous materials. A Park2 coding region may be amplified and/or expressed using the techniques disclosed herein or as would be known to those of ordinary skill in the art. Alternatively, various commercial preparations of proteins, polypeptides and peptides are known to those of skill in the art.

In certain embodiments a Park2 (or fragment or derivative thereof) proteinaceous compound may be purified. Generally, "purified" will refer to a specific protein, polypeptide, or peptide composition that has been subjected to fractionation to remove various other proteins, polypeptides, or peptides, and which composition substantially retains its activity, as may be assessed, for example, by the protein assays, as would be known to one of ordinary skill in the art for the specific or desired protein, polypeptide or peptide. Biological functional equivalents of Park2, including such derivatives and fragments, may be employed. As modifications and/or changes may be made in the structure of Park2 polynucleotides and and/or proteins according to the present disclosure, while obtaining molecules having similar or improved characteristics, such biologically functional equivalents are also encompassed within embodiments of the present disclosure.

A Park2 functional derivative or fragment thereof may comprise 1, 2, 3, 4, 5, 6, 7, 8, 9, 10, 11, 12, 13, 14, 15, 16, 17, 18, 19, or 20 or more amino acid alterations compared to SEQ ID NO:25. The Park2 functional derivative or fragment thereof may comprise an N-terminal truncation of SEQ ID NO:25, for example wherein the truncation is no more than 1, 2, 3, 4, 5, 6, 7, 8, 9, 10, 12, 15, 20, 25, 30, 35, 40, 45, 50, 55, 60, 65, 70, 75, 80, 85, 90, 95, or 100 amino acids or wherein the truncation is at least 1, 2, 3, 4, 5, 6, 7, 8, 9, 10, 12, 15, 20, 25, 30, 35, 40, 45, 50, 55, 60, 65, 70, 75, 80, 85, 90, 95, or 100 amino acids. The Park2 functional derivative or fragment thereof may comprise a C-terminal truncation of SEQ ID NO: 25, such as wherein the truncation is no more than 1, 2, 3, 4, 5, 6, 7, 8, 9, 10, 12, 15, 20, 25, 30, 35, 40, 45, 50, 55, 60, 65, 70, 75, 80, 85, 90, 95, or 100 amino acids or is at least 1, 2, 3, 4, 5, 6, 7, 8, 9, 10, 12, 15, 20, 25, 30, 35, 40, 45, 50, 55, 60, 65, 70, 75, 80, 85, 90, 95, or 100 amino acids. The Park2 functional derivative or fragment thereof may comprise an internal deletion in SEQ ID NO: 25, such as wherein the internal deletion is no more than 1, 2, 3, 4, 5, 6, 7, 8, 9, 10, 12, 15, 20, 25, 30, 35, 40, 45, 50, 55, 60, 65, 70, 75, 80, 85, 90, 95, or 100 amino acids or is at least 1, 2, 3, 4, 5, 6, 7, 8, 9, 10, 12, 15, 20, 25, 30, 35, 40, 45, 50, 55, 60, 65, 70, 75, 80, 85, 90, 95, or 100 amino acids. In specific embodiments, a Park2 functional derivative or fragment thereof may comprise sequence that is at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% identical to SEQ ID NO:25.

In one embodiment, there is a recombinant Park2 polypeptide or a functional derivative or functional fragment thereof. In a specific embodiment, the Park2 polypeptide comprises the sequence of SEQ ID NO:25. In particular embodiments, the polypeptide is comprised in a pharmaceutically acceptable carrier. In specific embodiments, the functional derivative or fragment thereof comprises 1, 2, 3, 4, 5, 6, 7, 8, 9, 10, 11, 12, 13, 14, 15, 16, 17, 18, 19, or 20 or more amino acid alterations compared to SEQ ID NO:25. The functional derivative or functional fragment thereof may comprise an N-terminal truncation of SEQ ID NO:25, in certain embodiments, and the truncation may be no more than 1, 2, 3, 4, 5, 6, 7, 8, 9, 10, 12, 15, 20, 25, 30, 35, 40, 45, 50, 55, 60, 65, 70, 75, 80, 85, 90, 95, or 100 amino acids or wherein the truncation is at least 1, 2, 3, 4, 5, 6, 7, 8, 9, 10, 12, 15, 20, 25, 30, 35, 40, 45, 50, 55, 60, 65, 70, 75, 80, 85, 90, 95, or 100 amino acids, in particular embodiments. In certain embodiments, the functional derivative or functional fragment thereof comprises a C-terminal truncation of SEQ ID NO:25, such as wherein the truncation is no more than 1, 2, 3, 4, 5, 6, 7, 8, 9, 10, 12, 15, 20, 25, 30, 35, 40, 45, 50, 55, 60, 65, 70, 75, 80, 85, 90, 95, or 100 amino acids or is at least 1, 2, 3, 4, 5, 6, 7, 8, 9, 10, 12, 15, 20, 25, 30, 35, 40, 45, 50, 55, 60, 65, 70, 75, 80, 85, 90, 95, or 100 amino acids, for example. In some embodiments, the functional derivative or functional fragment thereof comprises an internal deletion in SEQ ID NO:25, such as an internal deletion that is no more than 1, 2, 3, 4, 5, 6, 7, 8, 9, 10, 12, 15, 20, 25, 30, 35, 40, 45, 50, 55, 60, 65, 70, 75, 80, 85, 90, 95, or 100 amino acids or is at least 1, 2, 3, 4, 5, 6, 7, 8, 9, 10, 12, 15, 20, 25, 30, 35, 40, 45, 50, 55, 60, 65, 70, 75, 80, 85, 90, 95, or 100 amino acids, for example. In some cases, the Park2 functional derivative or fragment thereof may comprise sequence that is at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% identical to SEQ ID NO:25. In specific embodiments, the polypeptide is labeled.

A biological functional equivalent of Park2 may be produced from a polynucleotide that has been engineered to contain distinct sequences while at the same time retaining the capacity to encode the "wild-type" or standard protein. This can be accomplished to the degeneracy of the genetic code, i.e., the presence of multiple codons, which encode for the same amino acids. In one example, one of skill in the art may wish to introduce a restriction enzyme recognition sequence into a polynucleotide while not disturbing the ability of that polynucleotide to encode a protein.

In another example, a Park2 polynucleotide made be (and encode) a biological functional equivalent with more significant changes. Certain amino acids may be substituted for other amino acids in a protein structure without appreciable loss of interactive binding capacity with structures such as, for example, antigen-binding regions of antibodies, binding sites on substrate molecules, receptors, and so forth. So-called "conservative" changes do not disrupt the biological activity of the protein, as the structural change is not one that impinges on the protein's ability to carry out its designed function. It is thus contemplated by the inventors that various changes may be made in the sequence of genes and proteins disclosed herein, while still fulfilling the goals of the embodiments of the present disclosure.

In terms of functional equivalents, it is well understood by the skilled artisan that, inherent in the definition of a "biologically functional equivalent" protein and/or polynucleotide, is the concept that there is a limit to the number of changes that may be made within a defined portion of the molecule while retaining a molecule with an acceptable level of equivalent biological activity. Biologically functional equivalents are thus defined herein as those proteins (and polynucleotides) in selected amino acids (or codons) that may be substituted.

In general, the shorter the length of the molecule, the fewer changes that can be made within the molecule while retaining function. Longer domains may have an intermediate number of changes. The full-length protein will have the most tolerance for a larger number of changes. However, it must be appreciated that certain molecules or domains that are highly dependent upon their structure may tolerate little or no modification.

Amino acid substitutions are generally based on the relative similarity of the amino acid side-chain substituents, for example, their hydrophobicity, hydrophilicity, charge, size, and/or the like. An analysis of the size, shape and/or type of the amino acid side-chain substituents reveals that arginine, lysine and/or histidine are all positively charged residues; that alanine, glycine and/or serine are all a similar size; and/or that phenylalanine, tryptophan and/or tyrosine all have a generally similar shape. Therefore, based upon these considerations, arginine, lysine and/or histidine; alanine, glycine and/or serine; and/or phenylalanine, tryptophan and/or tyrosine; are defined herein as biologically functional equivalents.

To effect more quantitative changes, the hydropathic index of amino acids may be considered. Each amino acid has been assigned a hydropathy index on the basis of their hydrophobicity and/or charge characteristics, and these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (-0.9); tyrosine (−1.3); proline (−1.6); histidine (−3.2); glutamate (−3.5); glutamine (−3.5); aspartate (−3.5); asparagine (−3.5); lysine (−3.9); and/or arginine (−4.5).

The importance of the hydropathy amino acid index in conferring interactive biological function on a protein is generally understood in the art (Kyte & Doolittle, 1982, incorporated herein by reference). It is known that certain amino acids may be substituted for other amino acids having a similar hydropathy index and/or score and/or still retain a similar biological activity. In making changes based upon the hydropathy index, the substitution of amino acids whose hydropathy indices are within ±2 is preferred, those which are within ±1 are particularly preferred, and/or those within ±0.5 are even more particularly preferred.

It also is understood in the art that the substitution of like amino acids can be made effectively on the basis of hydrophilicity, particularly where the biological functional equivalent protein and/or peptide thereby created is intended for use in immunological embodiments, as in certain embodiments of the present invention. U.S. Pat. No. 4,554,101, incorporated herein by reference, states that the greatest local average hydrophilicity of a protein, as governed by the hydrophilicity of its adjacent amino acids, correlates with its immunogenicity and/or antigenicity, i.e., with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). In making changes based upon similar hydrophilicity values, the substitution of amino acids whose hydrophilicity values are within ±2 is preferred, those which are within ±1 are particularly preferred, and/or those within ±0.5 are even more particularly preferred.

The present invention, in many aspects, relies on the synthesis of peptides and polypeptides in cyto, via transcription and translation of appropriate polynucleotides. These peptides and polypeptides will include the twenty "natural" amino acids, and post-translational modifications thereof. However, in vitro peptide synthesis permits the use of modified and/or unusual amino acids. Exemplary, but not limiting, modified and/or unusual amino acids are known in the art.

In addition to the biological functional equivalents discussed above, the present inventors also contemplate that structurally or functionally similar compounds may be formulated to mimic the key portions of peptide or polypeptides of the present invention. Such compounds, which may be termed peptidomimetics, may be used in the same manner as the peptides of the invention and, hence, also are functional equivalents.

Certain mimetics that mimic elements of protein secondary and tertiary structure are described in Johnson et al. (1993). The underlying rationale behind the use of peptide mimetics is that the peptide backbone of proteins exists chiefly to orient amino acid side chains in such a way as to facilitate molecular interactions, such as those of antibody and/or antigen. A peptide mimetic is thus designed to permit molecular interactions similar to the natural molecule. Such peptidomimetics include compounds that do not incorporate any natural amino acids or amino acid side chains, but are instead designed based on a Park2 peptide sequence and have the ability to functionally replace Park2.

In some respects, a particular Park2 polynucleotide is utilized in compositions and methods of the embodiments of the disclosure. In some cases, the Park2 polynucleotide comprises, consists of, or consists essentially of part or all of a sequence of SEQ ID NO:26. The Park2 polynucleotide may comprise, consists of, or consist essentially of SEQ ID NO:26.

The nucleotide sequence has at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% identity to the sequence of SEQ ID NO. 26. The Park2 polynucleotide sequence may be at least about 1560, 1550, 1540, 1530, 1520, 1510, 1500, 1490, 1450, 1425, 1400, 1375, 1350, 1325, 1300, 1275, 1250, 1225, 1200, 1175, 1150, 1125, 1100, 1075, 1050, 1025, 1000, 975, 950, 925, 900, 875, 850, 825, 800, 775, 750, 725, 700, 675, 650, 625, 600, 575, 550, 525, 500, 475, 450, 425, 400, 375, 350, 325, 300, 275, 250, 225, 200, 175, 150, 125, 100, 75, 50, or 25 nucleotides of SEQ ID NO:26, including contiguous nucleotides of SEQ ID NO:26. Any effective fragment of SEQ ID NO:26 may be utilized. In specific embodiments, any region of SEQ ID NO:26 that imparts ligase activity to an encoded product may be included in the polynucleotide to be given to the

III. Methods of Use

Methods of embodiments of the disclosure encompass treatment or prophylactic activity for a cardiac condition. The methods may treat, delay onset of at least one symptom, and/or reduce severity of at least one symptom related to a cardiac condition. The methods may treat or reduce the severity or delay the onset of one or more cardiac conditions, and the methods may reduce the chance of mortality with a cardiac condition. The cardiac condition may be, for example, coronary heart disease, heart failure, hypertensive heart disease, inflammatory heart disease, rheumatic heart disease, coronary heart disease, and so forth.

In some embodiments of the disclosure, methods of treating an individual with a cardiac condition (or susceptible to or at risk for a cardiac condition) using one or more nucleic acids that express part or all of a Park2 polynucleotide are disclosed and described. In specific embodiments, the cardiac condition includes cardiomyocytes that are in need of renewal/regeneration either because of disease (contracted or genetic, for example) or because of trauma, for example. In specific embodiments, there is diseased heart in the individual. The individual may have cardiomyocytes that are in need of renewal/regeneration for any reason. Cardiomyocytes in the individual may be apoptotic, autophagic, or the tissue may be necrotic, for example. The individual may have damaged heart because of a prior or current event, such as, for example, an infarct or ischemia.

In specific embodiments, the individual may have, for example, heart failure, fibrosis of the heart, cardiomyopathy, ischemic cardiomyopathy, myocardial necrosis, dilated cardiomyopathy, degeneration of skeletal and/or cardiac muscle fibers, diabetic cardiomyopathy, age-related cardiomyopathy, and so forth. In specific embodiments, methods of the disclosure allow for the ability of cardiomyocytes to re-enter the cell cycle. The individual may be in need of improved cardiac function for any reason, including, for example, because of age, disease, trauma, a combination thereof, and so forth.

The individual may be of any age, race, gender, and so forth. The individual may be in need of preventing or delaying onset of a cardiac condition because of personal or family history and/or because of one or more risk factors.

In particular embodiments, the individual is provided a therapeutically effective amount of nucleic acid that expresses Park2 and/or Park2 polypeptides such that existing cardiomyocytes in the individual are able to renew/regenerate. In other embodiments, an individual is provided nucleic acids that express Park2 wherein the nucleic acids are already present in any kind of cell at the time of delivery of the cells, including a cardiomyocyte or stem cell, for example. An individual may be provided an effective amount of one or more Park2 polypeptides in lieu of or in addition to gene therapy with one or more Park2 polynucleotides.

The nucleic acid compositions of the embodiments of the disclosure may be provided to the individual once or more than once. The delivery may occur upon the diagnosis of a need for cardiomyocyte renewal/regeneration or upon diagnosis of a cardiac condition. Delivery may occur to an individual who is susceptible to a cardiac condition, such as, for example, an individual having a personal or family history of cardiac condition(s), being overweight, having high cholesterol, and/or a smoker. The delivery may cease or continue once it is determined that a cardiac symptom is improved and/or that cardiomyocytes are being renewed/regenerated.

IV. Pharmaceutical Preparations

Pharmaceutical compositions of embodiments of the present disclosure comprise a therapeutically effective amount of one or more of Park2 (or functional fragment or functional derivative) polynucleotide or polypeptide compositions dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least one Park2 (or functional fragment or functional derivative) will be known to those of skill in the art in light of the present disclosure, as exemplified by Remington: The Science and Practice of Pharmacy, 21st Ed. Lippincott Williams and Wilkins, 2005, incorporated herein by reference. Moreover, for animal (e.g., human) administration, it will be understood that preparations should meet sterility, pyrogenicity, general safety and purity standards as required by U.S. FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, and like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The Park2 (or functional fragment or functional derivative thereof) polynucleotide and/or polypeptide may comprise one or more hydrogels of any kind, including at least collagen, gelatine, hyaluronic acid, alginate, agarose, chitosan, keratin, polyacrylic acid, poly(ethylene oxide), polyvinyl alcohol, polyphosphazene, polypeptide chains, or combinations thereof.

The Park2 (or functional fragment or functional derivative thereof) polynucleotide and/or polypeptide may comprise different types of carriers depending on whether it is to be administered in solid, liquid or aerosol form, and whether it need to be sterile for such routes of administration as injection. The presently disclosed compositions can be administered locally or systemically, including, for example, intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), or through injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The Park2 (or functional fragment or functional derivative) polynucleotide and/or polypeptide may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acids. Salts formed with the free carboxyl groups can also be derived from inorganic bases such as for example, sodium, potassium, ammonium, calcium or ferric hydroxides; or organic bases such as isopropylamine, trimethylamine, histidine or procaine. Upon formulation, solutions will be administered in a manner compatible with the dosage formulation and in such amounts as are therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with embodiments of the present disclosure, the composition of the present disclosure suitable for administration are provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of a composition contained therein, its use in administrable composition for use in practicing the methods of embodiments of the present disclosure is appropriate. Examples of carriers or diluents include fats, oils, water, saline solutions, lipids, liposomes, resins, binders, fillers and the like, or combinations thereof. The compositions may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present disclosure, the compositions are combined with the carrier in any convenient and practical manner, i.e., by solution, suspension, emulsification, admixture, encapsulation, absorption and the like. Such procedures are routine for those skilled in the art.

In a specific embodiment of the present disclosure, the compositions are combined or mixed thoroughly with a semi-solid or solid carrier. The mixing can be carried out in any convenient manner such as grinding. Stabilizing agents can be also added in the mixing process in order to protect the compositions from loss of therapeutic activity, i.e., denaturation in the stomach. Examples of stabilizers for use in the compositions include buffers, amino acids such as glycine and lysine, carbohydrates such as dextrose, mannose, galactose, fructose, lactose, sucrose, maltose, sorbitol, mannitol, etc.

In further embodiments, the present disclosure may concern the use of pharmaceutical lipid vehicle compositions that include Park2 (or functional fragment or functional derivative) polynucleotides and/or polypeptides, one or more lipids, and an aqueous solvent. As used herein, the term "lipid" will be defined to include any of a broad range of substances that are characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man) However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of embodiments the present disclosure.

One of ordinary skill in the art would be familiar with the range of techniques that can be employed for dispersing a composition in a lipid vehicle. For example, the Park2 composition (or functional fragment or functional derivative) polynucleotide(s) and/or polypeptide(s) may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present disclosure administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or a therapeutically effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

A. Alimentary Compositions and Formulations

In preferred embodiments of the present invention, the Park2 composition (or functional fragment or functional derivative) polynucleotide(s) and/or polypeptide(s) are formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792,451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For example, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629,001, which is incorporated herein by reference in its entirety. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration the compositions of the present disclosure may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

Additional formulations which are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Parenteral Compositions and Formulations

In further embodiments, Park2 composition (or functional fragment or functional derivative) polynucleotide(s) and/or polypeptide(s) may be administered via a parenteral route. As used herein, the term "parenteral" includes routes that bypass the alimentary tract. Specifically, the pharmaceutical compositions disclosed herein may be administered for example, including but not limited to intravenously, intradermally, intramuscularly, intraarterially, intrathecally, subcutaneous, or intraperitoneally U.S. Pat. Nos. 6,7537,514, 6,613,308, 5,466,468, 5,543,158; 5,641,515; and 5,399,363 (each specifically incorporated herein by reference in its entirety).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in isotonic NaCl solution and either added hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

Miscellaneous Pharmaceutical Compositions and Formulations

In other embodiments of the disclosure, the active compound Park2 composition (or functional fragment or functional derivative) polynucleotide(s) and/or polypeptide(s) may be formulated for administration via various miscellaneous routes, for example, topical (i.e., transdermal) administration, mucosal administration (intranasal, vaginal, etc.) and/or inhalation.

Pharmaceutical compositions for topical administration may include the active compound formulated for a medicated application such as an ointment, paste, cream or powder. Ointments include all oleaginous, adsorption, emulsion and water-solubly based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of embodiments of the present disclosure may also comprise the use of a "patch". For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

The term aerosol refers to a colloidal system of finely divided solid and liquid particles dispersed in a liquefied or pressurized gas propellant. The typical aerosol for embodiments of the present disclosure for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

V. Combination Therapy

In some embodiments of the disclosure, one or more compositions of the present disclosure are provided in a therapeutically effective amount with one or more other therapies (and/or preventative compositions) for cardiac conditions. Other therapies include, for example, proper diet including healthy foods, exercise, blood pressure control, cholesterol-lowering drug(s), surgery, stents, pacemakers, defibrillators, heart transplant, ACE inhibitors, angiotension II receptor blockers, antiarrhythmics, antiplatelet drugs, aspirin, beta blockers, calcium channel blockers, clot busters, diuretics, nitrates, warfarin, or a combination thereof.

In addition to these combinatorial therapies, the methods and compositions of embodiments the present disclosure may also (or in lieu of) include one or more other therapies. One example is an agent that targets the Hippo pathway member Salvador (salvador family WW domain containing protein 1) (the gene may be referred to as salvador homolog 1, Salv, SAV1, SAV, WW45, or WWP4). Examples of such agents include shRNA or siRNA that target Savl1. As used herein, the terms "small interfering" or "short interfering RNA" or "siRNA" refer to an RNA duplex of nucleotides that is targeted to a desired gene and is capable of inhibiting the expression of a gene with which it shares homology. The RNA duplex comprises two complementary single-stranded RNAs of 15, 16, 17, 18, 19, 20, 21, 22, 23, 24, or 25 nucleotides that form 15, 16, 17, 18, 19, 20, 21, 22, 23, 24, or 25 base pairs and possess 3' overhangs of two nucleotides. The RNA duplex is formed by the complementary pairing between two regions of an RNA molecule. siRNA is "targeted" to a gene in that the nucleotide sequence of the duplex portion of the siRNA is complementary to a nucleotide sequence of the targeted gene. In some embodiments, the length of the duplex of siRNAs is less than 30 nucleotides. The duplex can be, for example, 29, 28, 27, 26, 25, 24, 23, 22, 21, 20, 19, 18, 17, 16, 15, 14, 13, 12, 11 or 10 nucleotides in length. The length of the duplex can be, for example, 17-25 nucleotides in length. The duplex RNA can be expressed in a cell from a single construct.

As used herein, the term "shRNA" (small hairpin RNA) refers to an RNA duplex wherein a portion of the siRNA is part of a hairpin structure (shRNA). In addition to the duplex portion, the hairpin structure may contain a loop portion positioned between the two sequences that form the duplex. The loop can vary in length. In some embodiments the loop is, for example, 5, 6, 7, 8, 9, 10, 11, 12 or 13 nucleotides in length. The hairpin structure can also contain 3' or 5' overhang portions. In some aspects, the overhang is a 3' or a 5' overhang and 0, 1, 2, 3, 4 or 5 nucleotides in length. In one aspect of this invention, a nucleotide sequence in the vector serves as a template for the expression of a small hairpin RNA, comprising a sense region, a loop region and an antisense region. Following expression, the sense and antisense regions form a duplex. It is this duplex, forming the shRNA, which hybridizes to, for example, the Sav1 mRNA and reduces expression of Sav1.

A representative nucleic acid is provided at GenBank® Accession No. CR457297.1, and a representative protein sequence is provided at GenBank® Accession No. Q9H4B6. Examples of particular agents that target the Sav1 mRNA include at least the following:

```
                                          (SEQ ID NO: 27)
aagtacgtga agaaggagac g;

(SEQ ID NO: 28)
aagatttacc ccttcctcct g;

(SEQ ID NO: 29)
attcctgact ggcttcaggt;

(SEQ ID NO: 30)
aagtacgtga agaaggagac g;

(SEQ ID NO: 31)
aagatttacc ccttcctcct g;

(SEQ ID NO: 32)
attcctgact ggcttcaggt;

(SEQ ID NO: 33)
aagtacgtga agaaggagac g;

(SEQ ID NO: 34)
aagatttacc ccttcctcct g;

(SEQ ID NO: 35)
attcctgact ggcttcaggt.
```

VI. Kits of the Disclosure

Any of the compositions described herein may be comprised in a kit. In a non-limiting example, Park2 compositions (or functional fragment or functional derivative), whether they be polynucleotides or polypeptides or a combination thereof, may be comprised in a kit. The kits will thus comprise, in suitable container means, Park2 composition(s) (or functional fragment or functional derivative).

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the Park2 compositions (or functional fragment or functional derivative) in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred. The Park2 compositions (or functional fragment or functional derivative) may also be formulated into a syringeable composition. In which case, the container means may itself be a syringe, pipette, and/or other such like apparatus, from which the formulation may be applied to an infected area of the body, injected into an animal, and/or even applied to and/or mixed with the other components of the kit.

However, the components of the kit may be provided as dried powder(s). When reagents and/or components are provided as a dry powder, the powder can be reconstituted by the addition of a suitable solvent. It is envisioned that the solvent may also be provided in another container means.

The kits of the present disclosure will also typically include a means for containing the vials in close confinement for commercial sale, such as, e.g., injection and/or blow-molded plastic containers into which the desired vials are retained.

The kit may comprise Park2 composition(s) (or functional fragment or functional derivative) formulated as a cardiac therapy.

EXAMPLES

The following examples are included to demonstrate certain non-limiting aspects of the invention. It should be appreciated by those of skill in the art that the techniques disclosed in the examples that follow represent techniques discovered by the inventors to function well in the practice of the disclosed subject matter. However, those of skill in the art should, in light of the present disclosure, appreciate that many changes can be made in the specific embodiments that are disclosed and still obtain a like or similar result without departing from the spirit and scope of the disclosed and described subject matter.

Example 1

Hippo Pathway Deficiency Reverses Systolic Heart Failure After Infarction

Figure 2A:
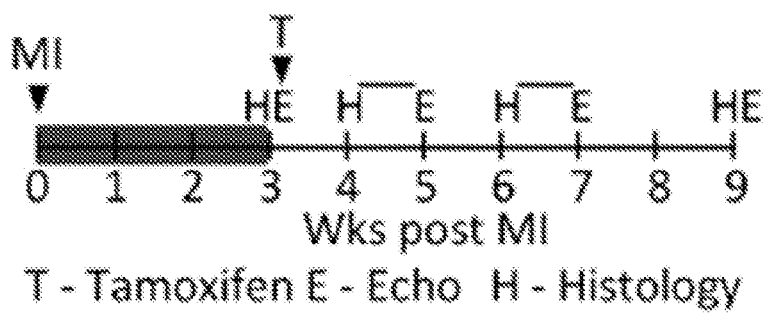
FIGS. 2a-2q. Reversal of heart failure and cardiomyocyte renewal in SalvCKO mice. 2a, Experimental timeline. Numbers per group analysed by echocardiography. MI, myocardial infarction. T, tamoxifen; E, echo; H, histology. 2b, 2c, Fractional shortening (FS) (2b) and ejection fraction (EF) (2c); analysis of variance (ANOVA), Tukey's pairwise post-hoc test. 2d, 2e, Masson's trichrome serial sections 9 weeks after myocardial infarction, n=7 per group. Scar boundaries (open arrows); ischaemic region (solid arrows). Scar categories I, II, III. Scale bar, 2 mm 2f, Left ventricle scar size, n=7 per group, Mann-Whitney U-test. 2g, Fibrosis and function: second-order polynomial fit. 2h, Cardiac regions. 2i, 2j, PCM-1 immunofluorescence (2i); scale bar, 100 µm; quantification (2j), n=3 per group, Mann-Whitney U-test. k, l, EdU-labelled cardiomyocytes (arrow) (2k) scale bar, 25 µm; quantification (l), SalvCKO myocardial infarction: 3 weeks (n=4), 9 weeks (n=5), others (n=3); ANOVA, Bonferroni's post-hoc test. 2m, 2n, pH H3 immunofluorescence (arrow) (2m), scale bar, 25 µm; quantification (2n), n=3 per group, Mann-Whitney U-test. 2o, 2p, Border zone lineage labelling (2o); scale bar, 25 µm; quantification (2p), n=3 per group; ANOVA, Bonferroni's post-hoc test. 2q, Cardiomyocyte cross-sectional area of whole heart (WH) and border zone 9 weeks after myocardial infarction, control myocardial infarction (n=3) SalvCKO myocardial infarction (n=5); ANOVA, Bonferroni's post-hoc test. Control: tamoxifen-injected αMHC-mcm; ROSA$^{mT/mG}$. SalvCKO; tamoxifen-injected αMHC-mcm; ROSA$^{mT/mG}$, Salv$^{fl/fl}$. Data are mean±s.e.m., P>0.05 non-significant (NS), *P<0.05, P<0.01, *P<0.001.
Figure 2B:
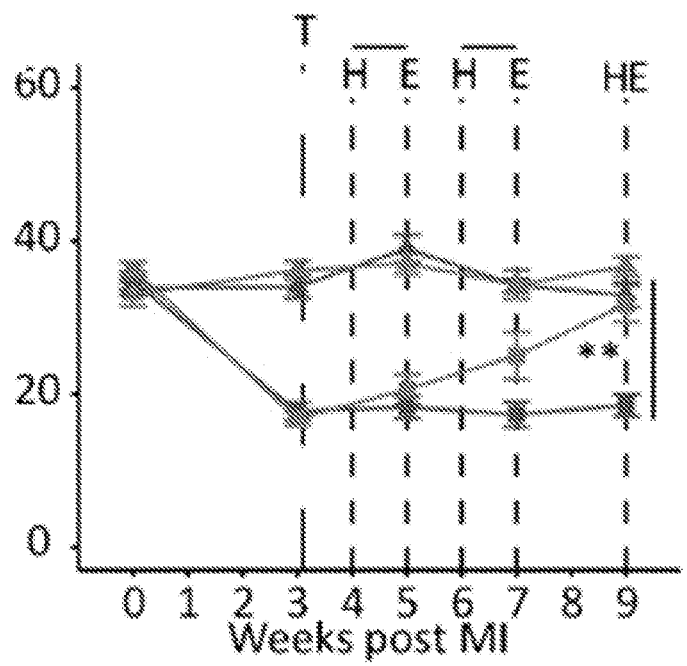
Figure 2C:
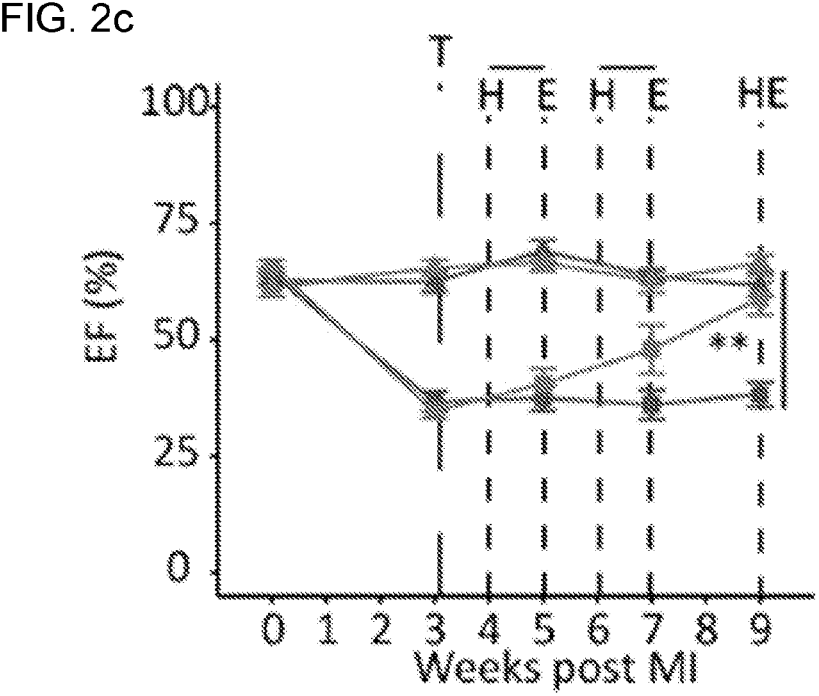
Figure 5A:
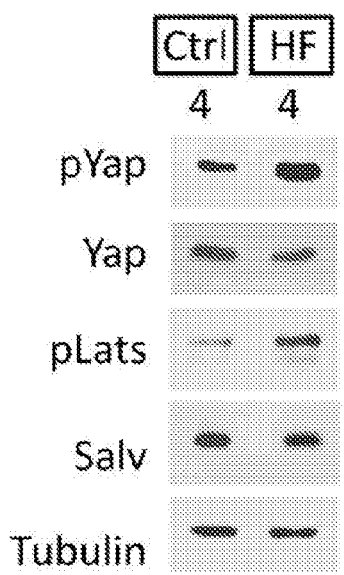
FIGS. 5a-5c. Activated Hippo signalling in human heart failure. 5a-5c, Western blots human heart samples. Ctrl: non-failing non-transplantable, n=6 (5a-5c). HF: non-ischaemic idiopathic cardiomyopathy in end-stage heart failure, n=6 (5a, 5b). iHF: ischaemic heart in end-stage heart failure, n=6 (5c). Quantification presented in FIG. 1.
Figure 5B:
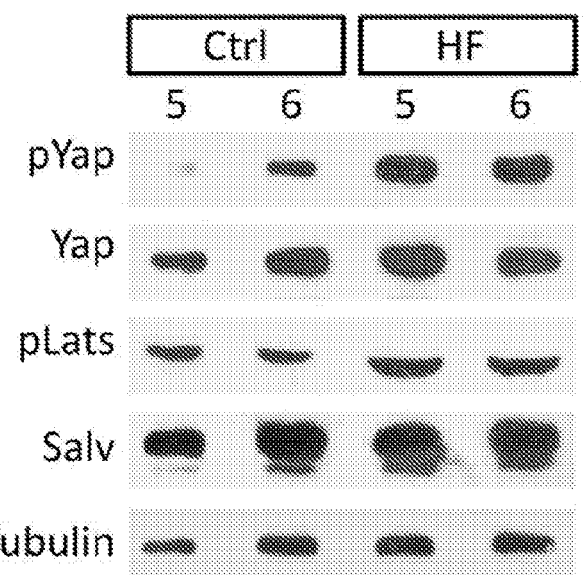
Figure 5C:
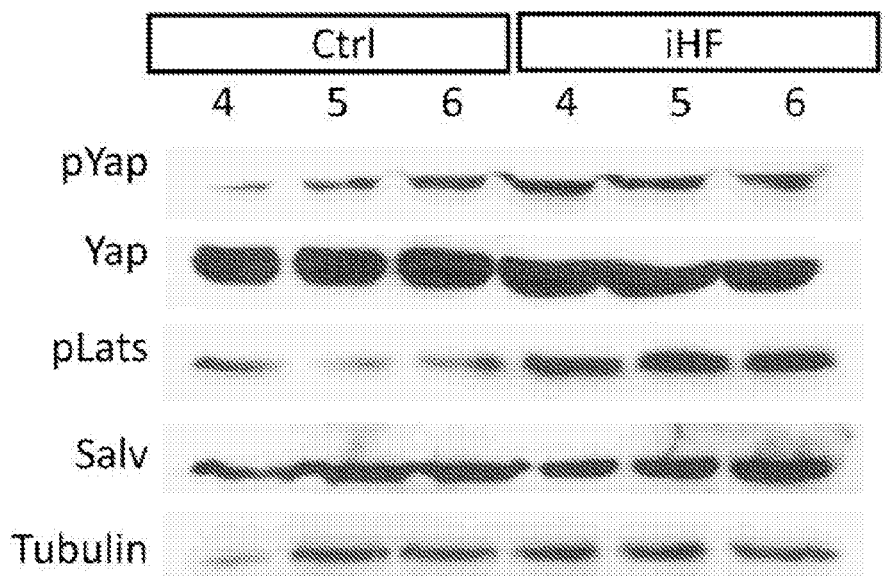
Figure 6A:
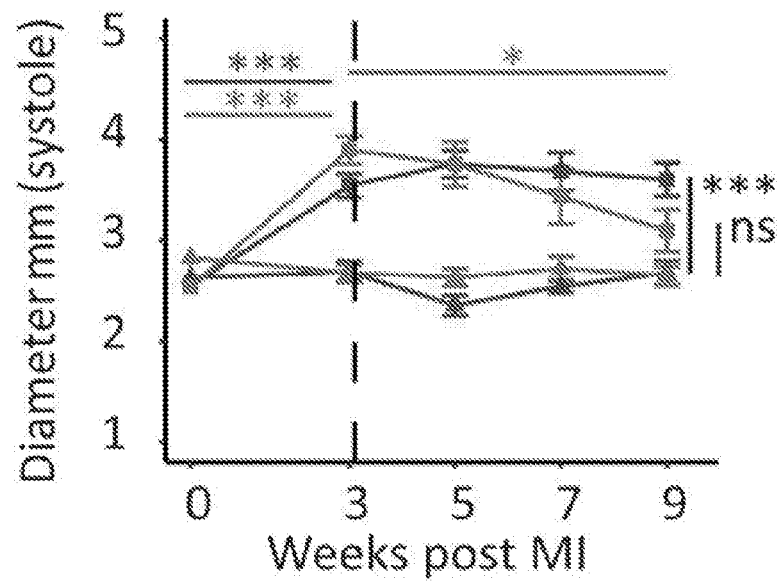
FIGS. 6a-6l. Mouse model of systolic heart failure. 6a-6d, Systolic diameter (6a), diastolic diameter (6b), systolic volume (6c), and diastolic volume (6d); n values indicated in FIG. 1a; ANOVA, Tukey's pairwise post-hoc test. 6e, 6f, Haematoxylin and eosin oedema liquid (pink transudate fluid) in lung tissue 3 weeks after myocardial infarction, sham (n=3) (6e) and myocardial infarction (n=5) (6f); scale bar, 50 µm. 6g, 6h, Prussian blue haemosiderin (blue) in lung tissue 3 weeks after myocardial infarction, sham (n=3) (6g) and myocardial infarction (n=5) (6h); scale bar, 50 µm. 6i, Natriuretic peptide B (BNP) in blood serum 3 weeks after myocardial infarction, Mann-Whitney U-test (6i). 6j, Weight gain 3 weeks after myocardial infarction (6j), t-test. 6k, 6l, Longitudinal echocardiography beginning 3 weeks after myocardial infarction; data are a subset of FIG. 2c. Control sham and control myocardial infarction samples were split by Cre genotype or by injection type, indicated in parenthesis (6k). No significant effect of Cre or tamoxifen (Tam) was observed; ANOVA, Tukey's pairwise post-hoc test (6k). Data are mean±s.e.m., P>0.05 non-significant (NS), *P<0.05, P<0.01, *P<0.001.
Figure 6B:
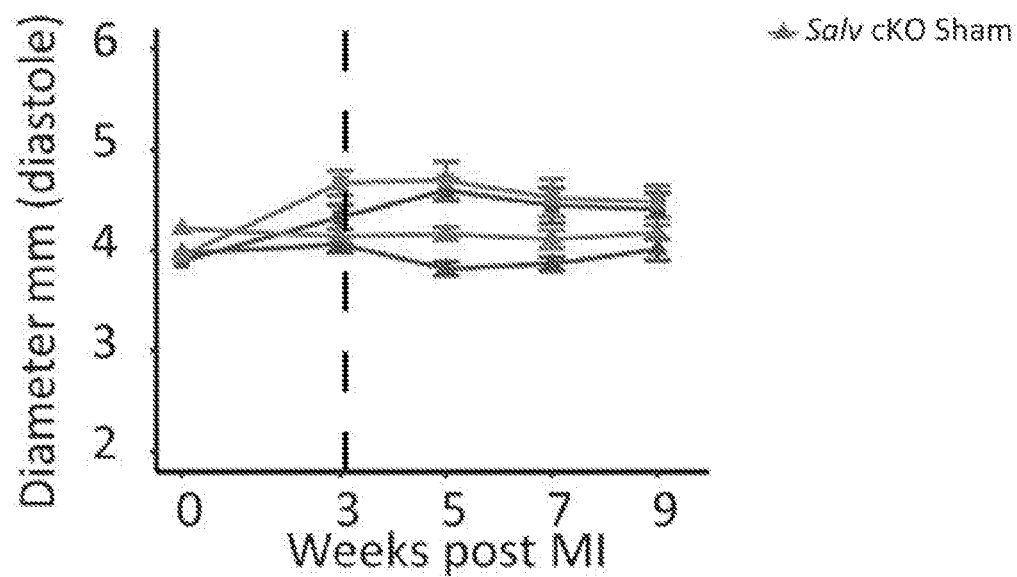
Figure 6C:
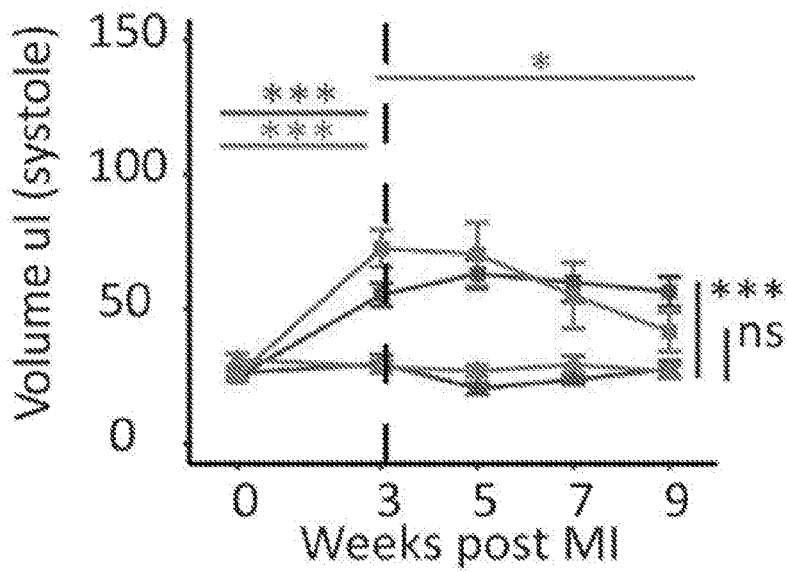
Figure 6D:
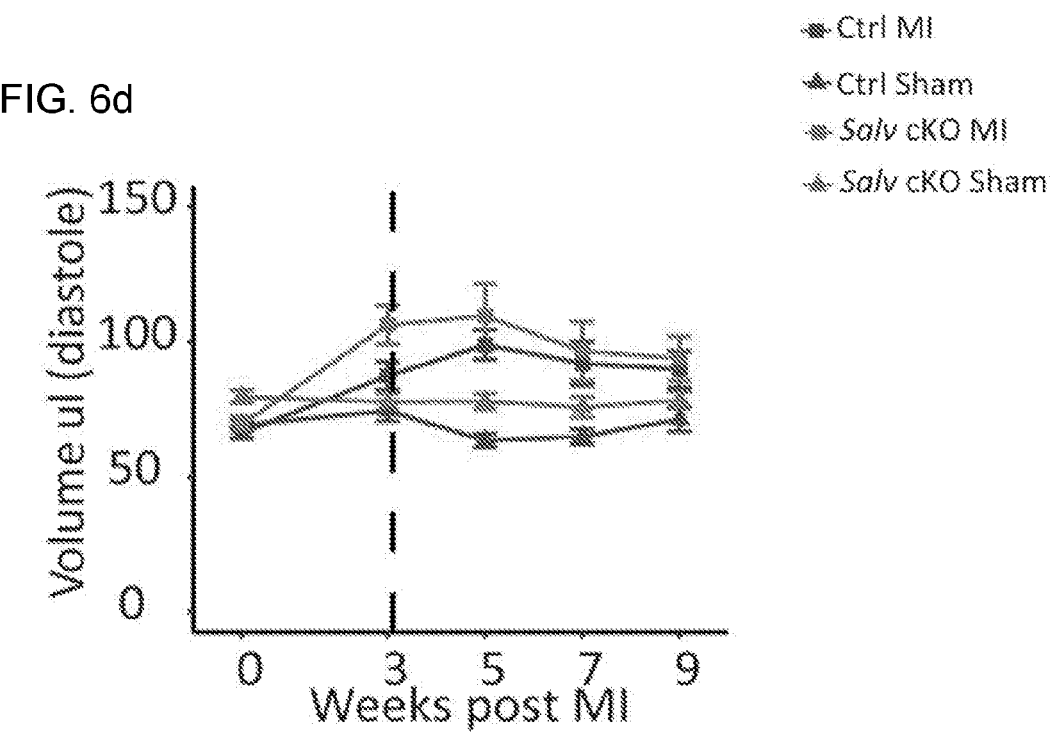
Figure 6E:
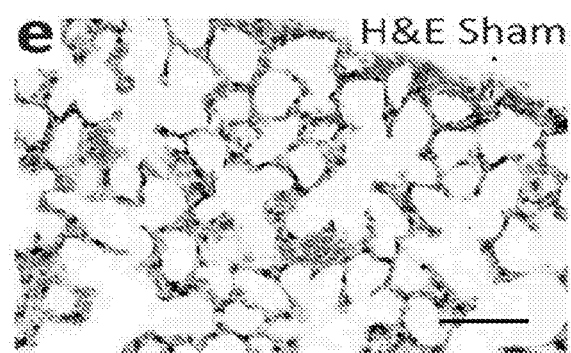
Figure 6F:
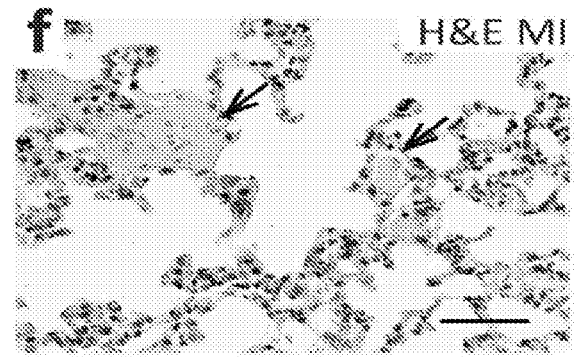
Figure 6G:
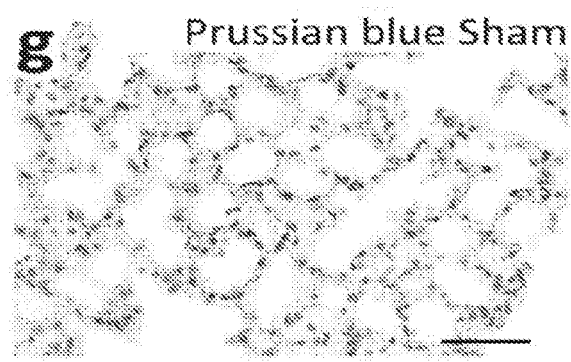
Figure 6H:
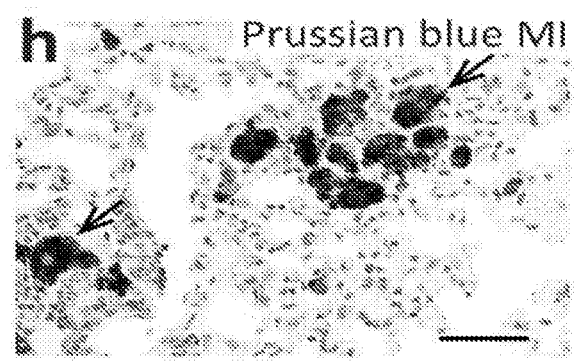
Figure 6I:
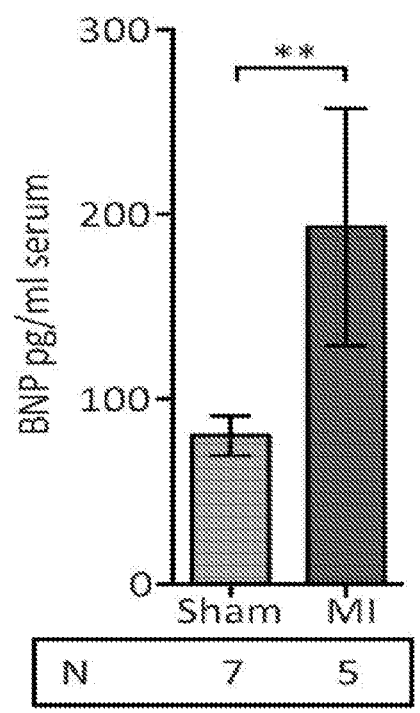
Figure 6J:
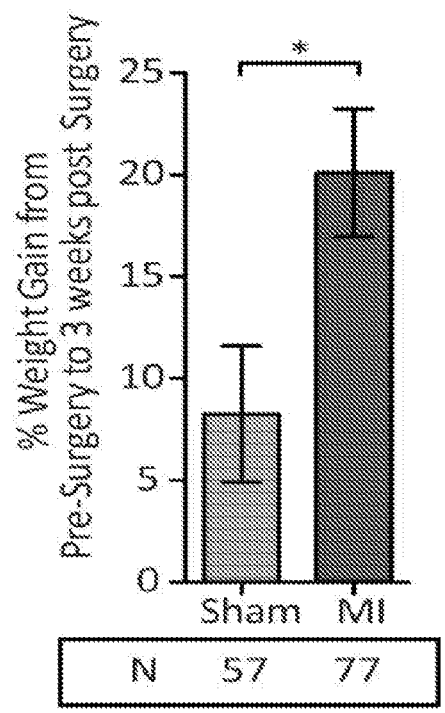
Figure 6K:
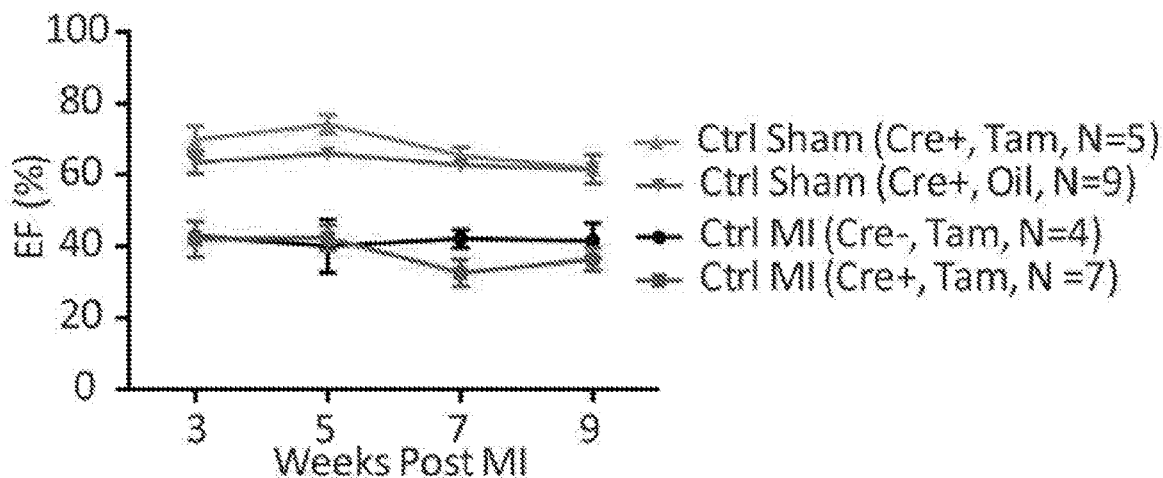
Figure 6L:
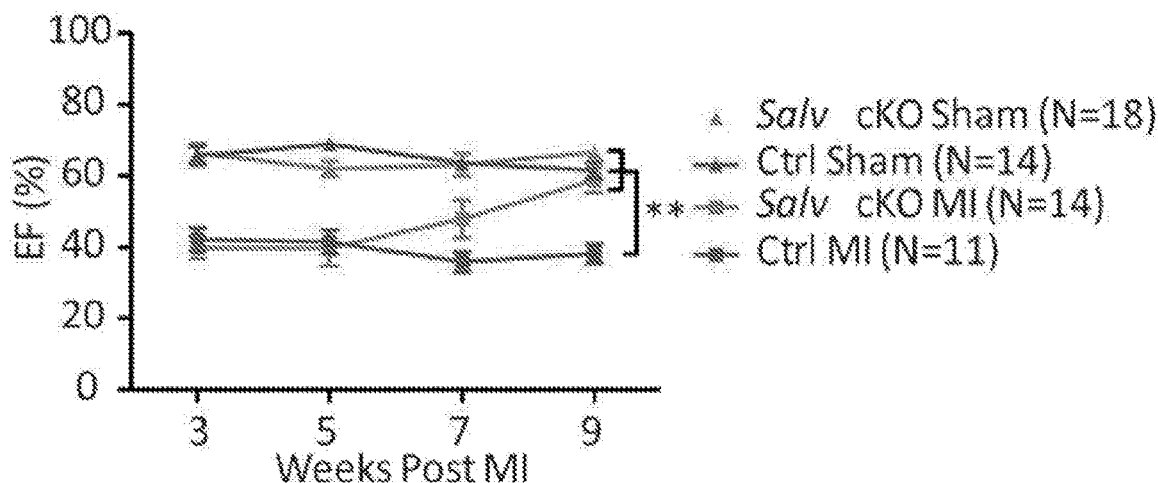

Western blots on human samples of ischaemic and non-ischaemic heart failure revealed that pYap and pLats serine 909 levels were higher and Salv levels unchanged in both types of samples than in the controls (FIGS. 1a-1f and FIGS. 5a-5c). The inventors generated αMHC-mcm;Salv$^{f/f}$ (SalvCKO) mice with ischaemic heart failure after myocardial infarction (FIG. 2a). Echocardiography 3 weeks after myocardial infarction and before treatment with tamoxifen revealed shams had an average ejection fraction of 64±12% and fractional shortening of 35±8% (FIGS. 2a-c). After myocardial infarction, mice had an average ejection fraction of 36±11% and fractional shortening of 18±6% (FIGS. 2a-c) (Gao et al., 2000). End-systolic variables showed increased systolic left ventricle chamber diameters (sham 2.7±0.6 mm, myocardial infarction 4.1±0.5 mm) and volumes (sham 29±18 μl, myocardial infarction 76±23 μl) (FIGS. 6a-6d). Diastolic indices were unchanged, indicating ischaemic heart failure was a result of systolic dysfunction (FIGS. 6b, 6d). Other ischaemic heart failure signs included pulmonary fluid build-up, haemosiderin-laden macrophages, increased natriuretic peptide B (BNP) serum levels, and increased body weights (FIGS. 6e-6j).

Three weeks after myocardial infarction, the inventors deleted Salv in cardiomyocytes and performed echocardiography every 2 weeks until 9 weeks after myocardial infarction (6 weeks after tamoxifen injection) (FIGS. 2a-c and FIGS. 6a-6d, 6k, 6l). At 9 weeks after myocardial infarction, SalvCKO had improved function (ejection fraction: SalvCKO myocardial infarction 59%±13%, control myocardial infarction 38±9%, P=0.001) similar to sham controls (ejection fraction: SalvCKO myocardial infarction 59%±13%, control and SalvCKO sham 65%±8%, P=1) (FIG. 2c).

Figure 2D:
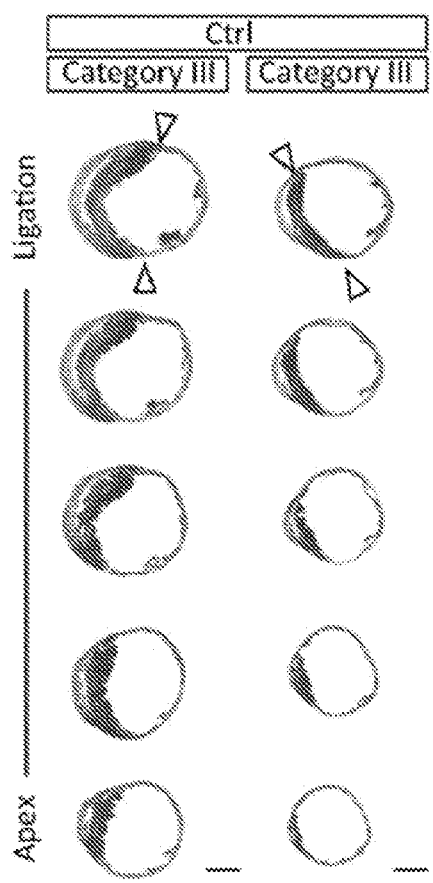
Figure 2E:
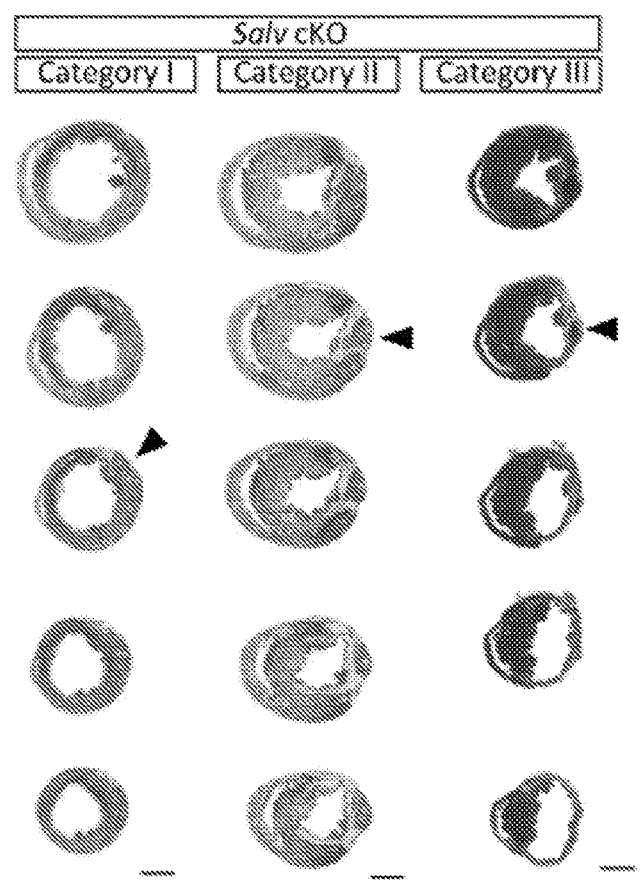
Figure 2F:
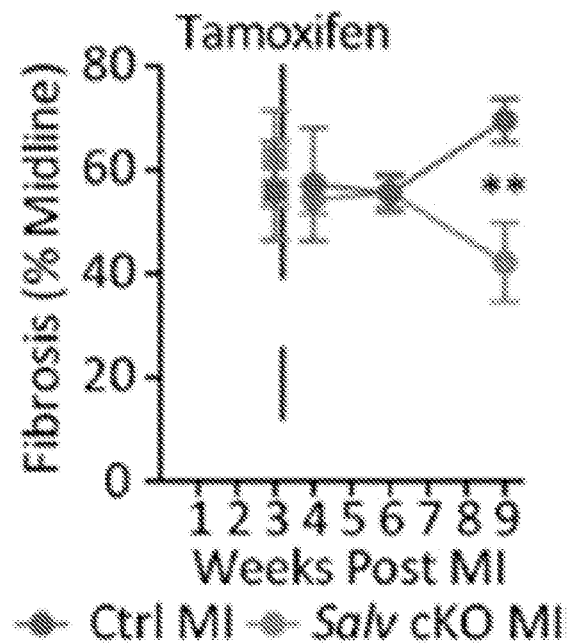
Figure 2G:
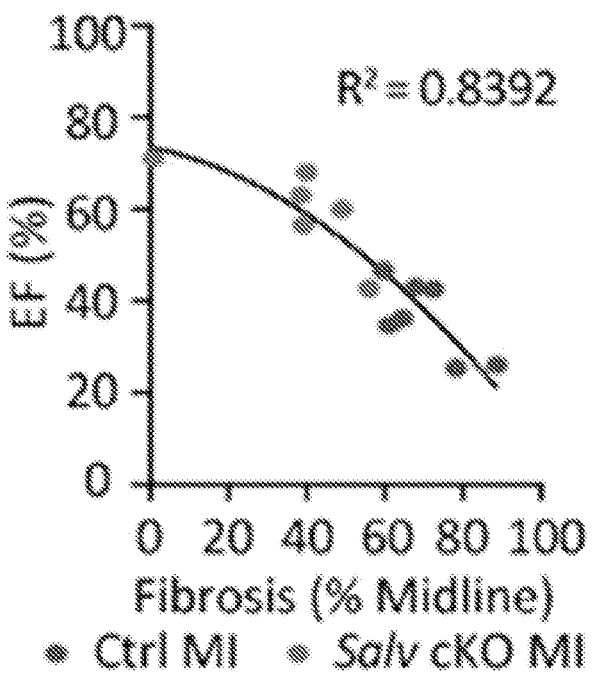
Figure 2H:
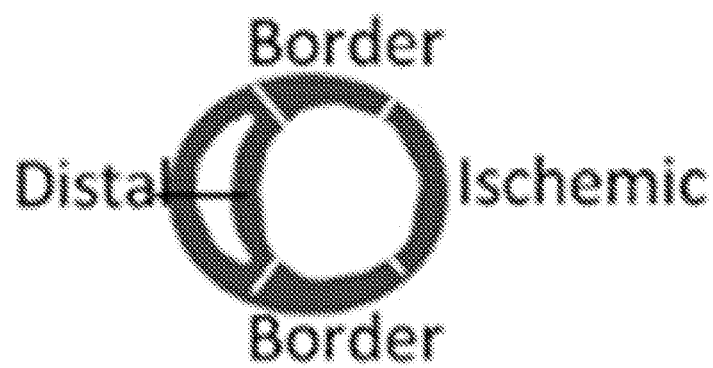
Figure 2I:
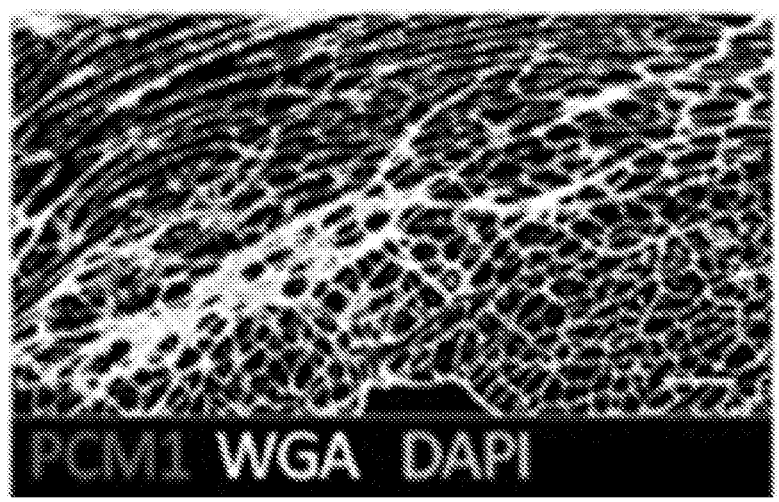
Figure 2J:
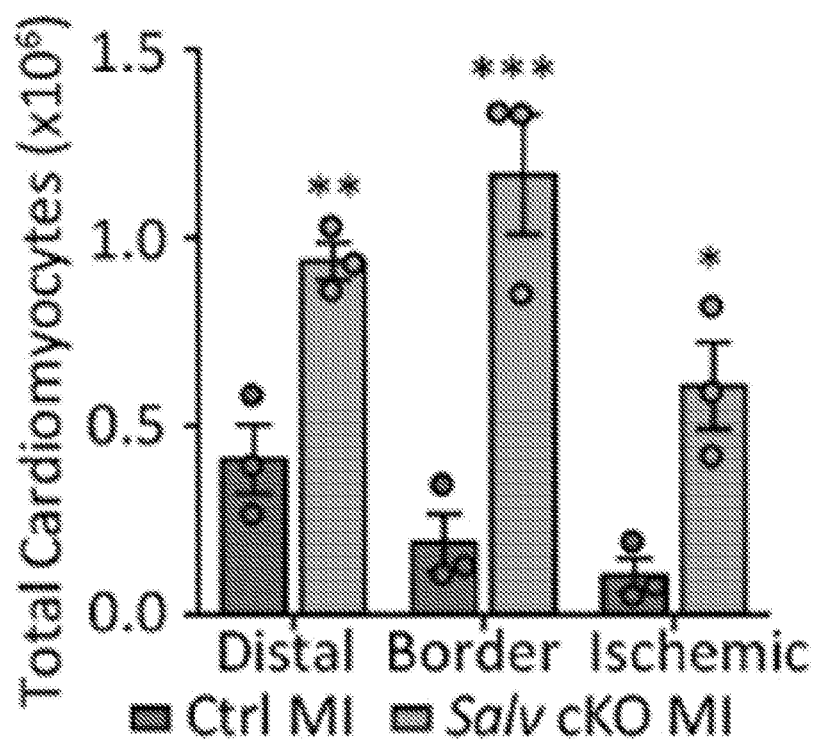

Control hearts 9 weeks after myocardial infarction had remodelled scars whereas SalvCKO hearts showed less fibrosis and more left ventricle cardiomyocytes (fibrosis: control 56±12%, SalvCKO 36±15%; cardiomyocyte number: control $1\times10^5\pm8\times10^4$, SalvCKO $6\times10^5\pm2\times10^5$) (FIGS. 2d-2j). We defined three qualitative categories of damage in SalvCKO hearts after myocardial infarction (FIGS. 2d, 2e). Category I, observed in 10% of SalvCKO cohort (N=1 of 10), recovered most left ventricle cardiomyocytes. Category II, observed in 80% of SalvCKO hearts (N=8 of 10), had an equal amount of fibrotic and cardiomyocyte area in the left ventricle. Category III, observed in 10% of SalvCKO hearts (N=1 of 10), had few left ventricle cardiomyocytes with a remodelled scar (FIGS. 2d-2f). The relationship between fibrosis and function was described by a second-order polynomial, suggesting that fibrosis is tolerated to maintain cardiac function (FIG. 2g).

Figure 7:
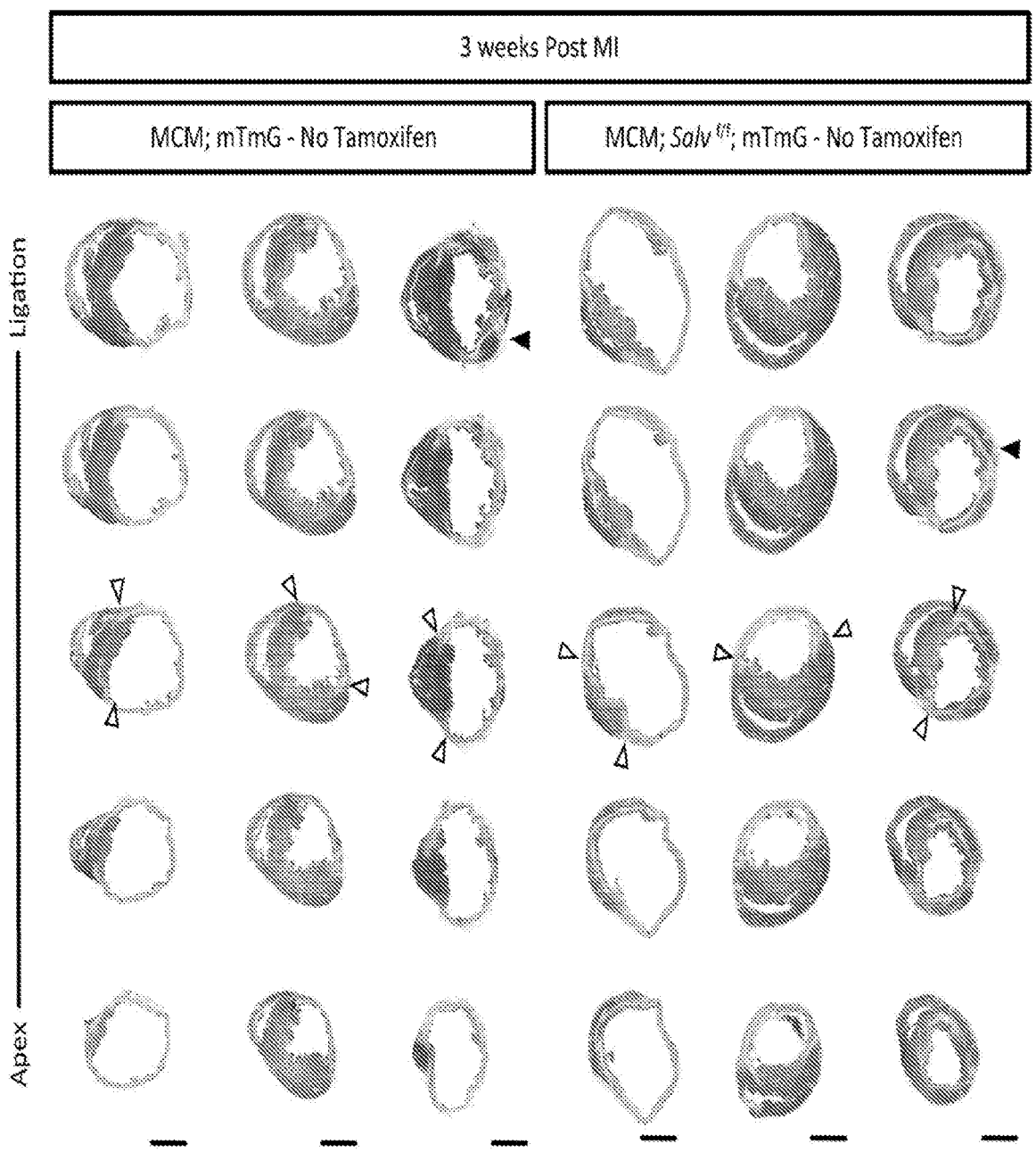
FIG. 7. Histological analysis at 3 weeks after myocardial infarction. Masson's trichrome of serial sagittal sections 3 weeks after myocardial infarction, no tamoxifen was delivered; genotype is indicated, n=3 per group, scar boundaries (open arrows), cardiomyocytes in the ischaemic region (solid arrows); scale bar, 2 mm.
Figure 8:
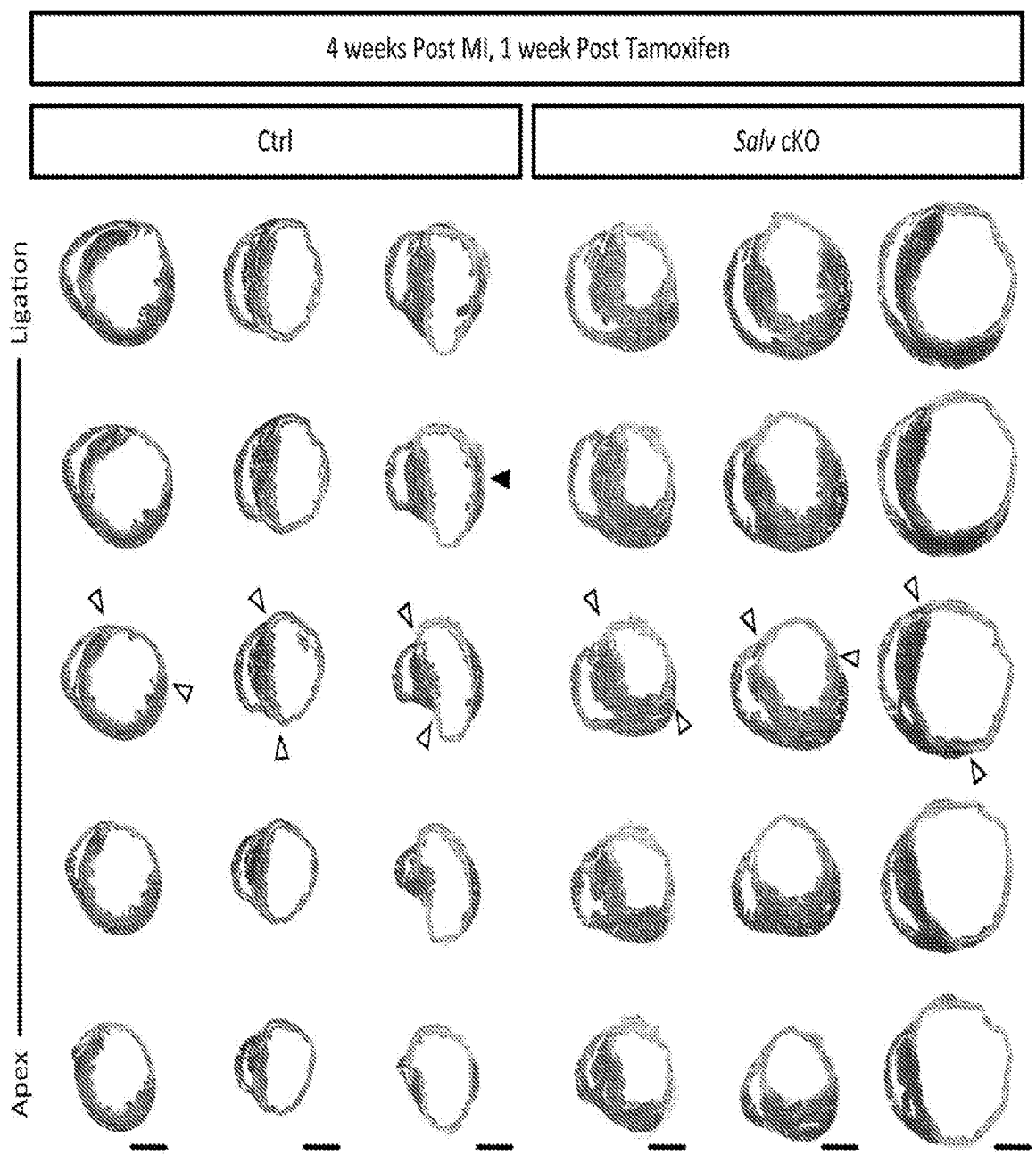
FIG. 8. Histological analysis at 4 weeks after myocardial infarction. Masson's trichrome of serial sagittal sections 4 weeks after myocardial infarction, 1 week after tamoxifen; control (αMHC-mcm; mTmG) and SalvCKO (αMHC-mcm; mTmG; Salv$^{fl/fl}$), n=3 per group, scar boundaries (open arrows), cardiomyocytes in the ischaemic region (solid arrows); scale bar, 2 mm.
Figure 9:
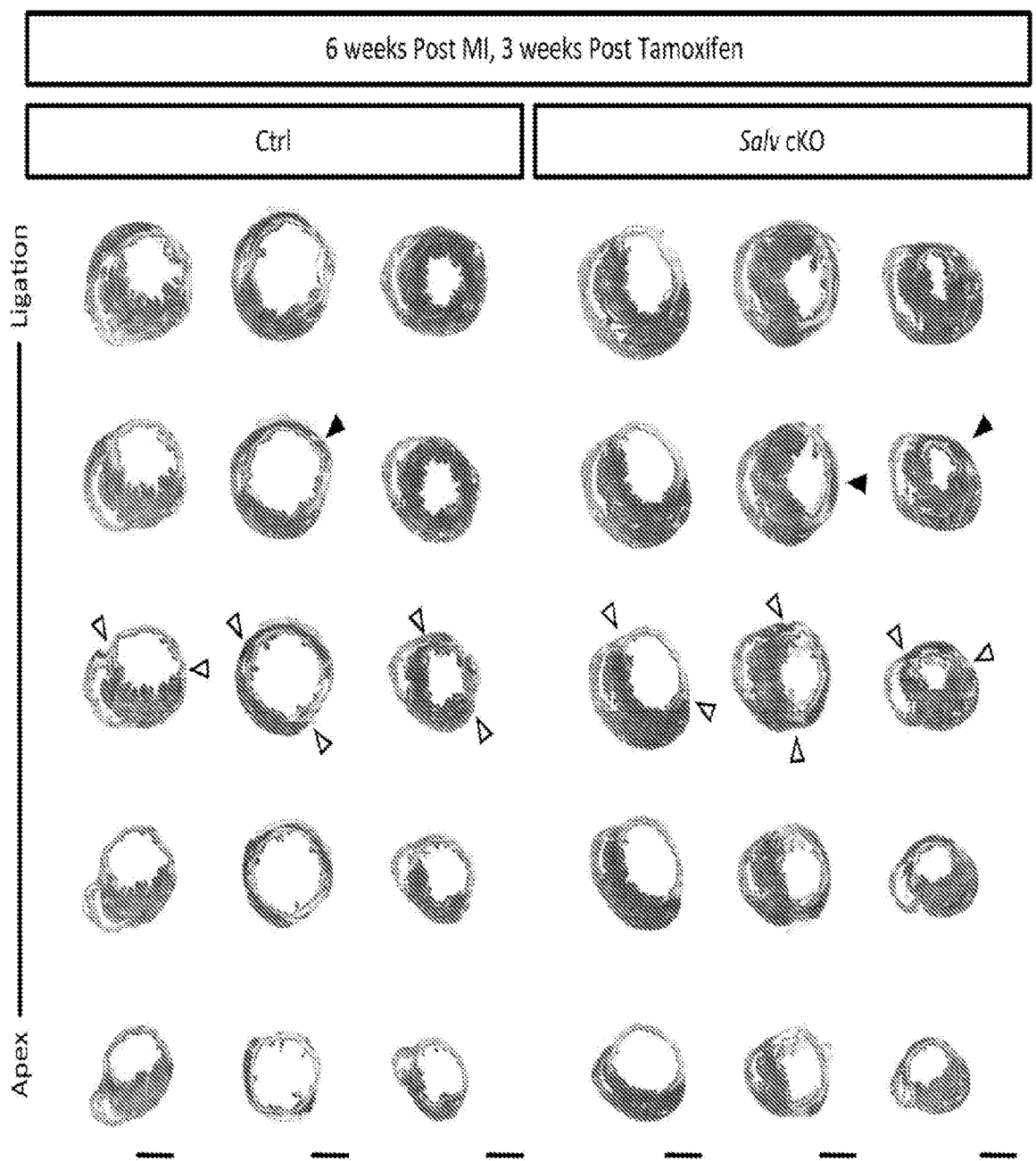
FIG. 9. Histological analysis at 6 weeks after myocardial infarction. Masson's trichrome of serial sagittal sections 6 weeks after myocardial infarction, 3 weeks after tamoxifen; control (αMHC-mcm; mTmG) and SalvCKO (αMHC-mcm; mTmG; Salve), n=3 per group, scar boundaries (open arrows), cardiomyocytes in the ischaemic region (solid arrows); scale bar, 2 mm.
Figure 10A:
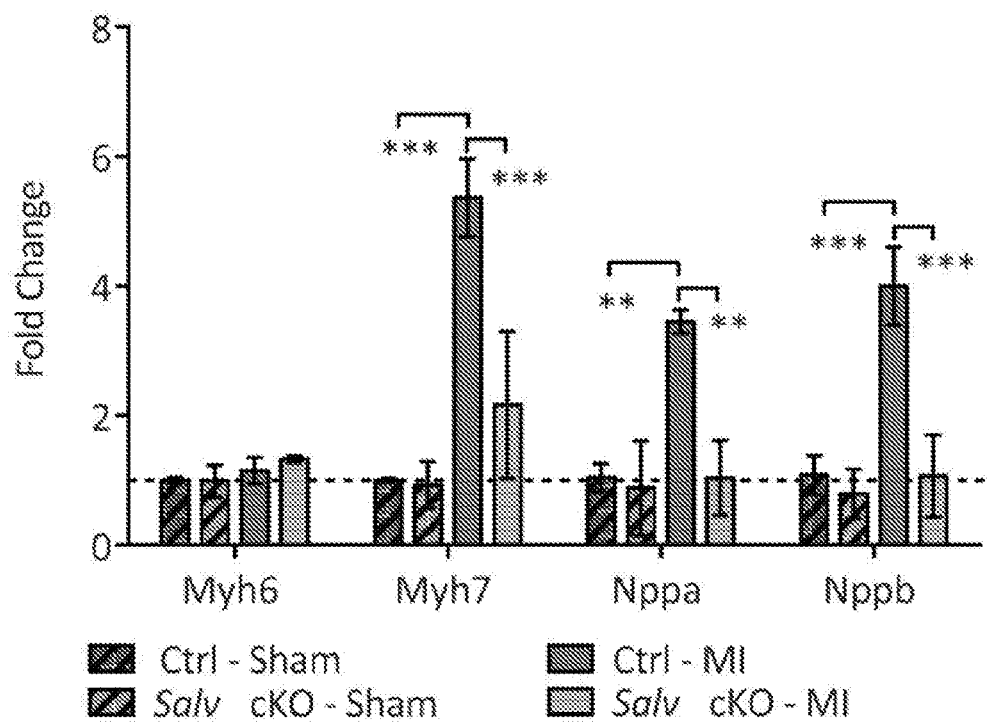
Figure 10B:
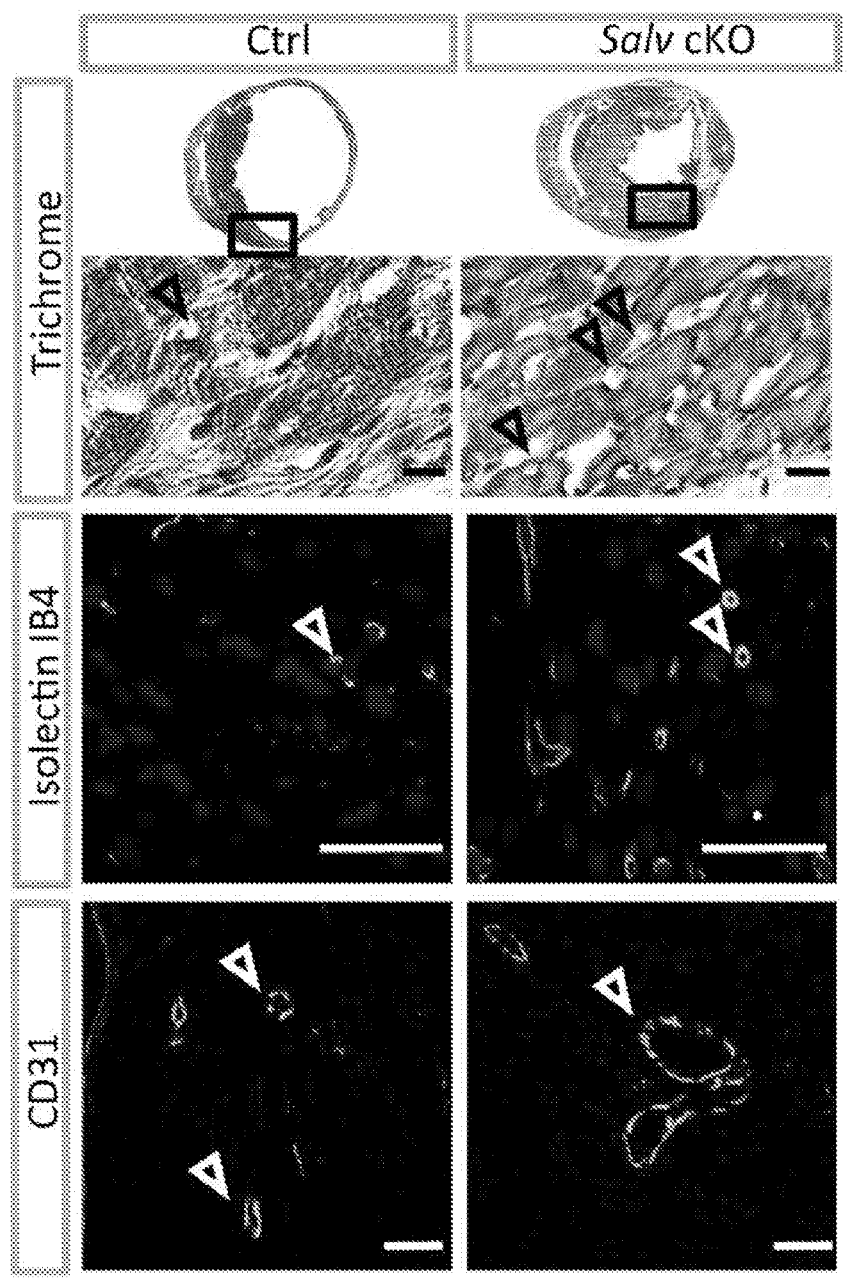
Figure 10C:
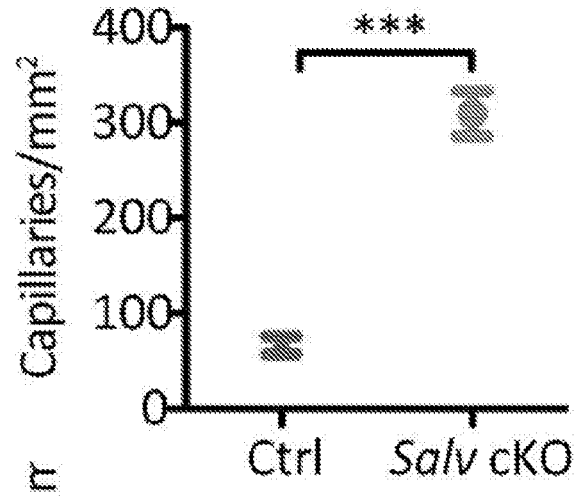
Figure 10D:
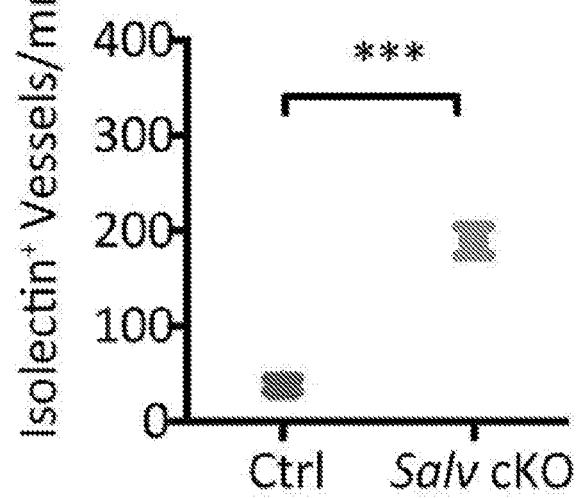
Figure 10E:
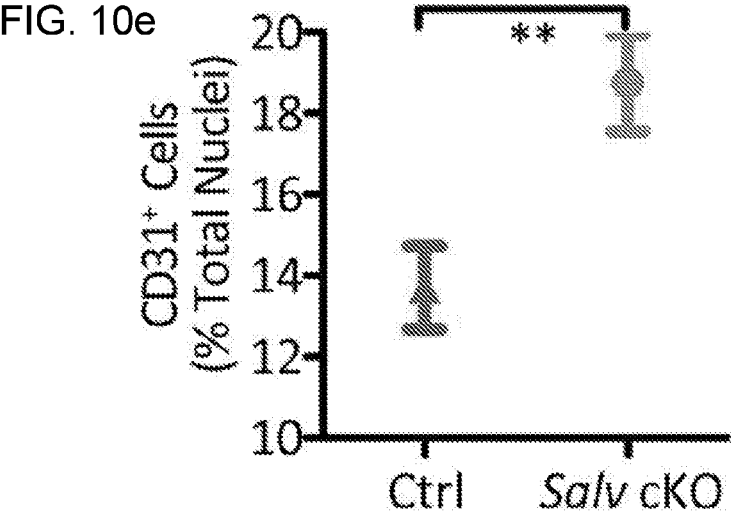

Three weeks after myocardial infarction, all hearts had left ventricle infarcts (FIG. 7). At two time points, hearts were collected 1 week before echocardiography for histopathology. The inventors discuss those time points as a 2 week range (that is, 4-5 and 6-7 weeks after myocardial infarction). There were no differences between the groups at 4-5 weeks and 6-7 weeks after myocardial infarction (FIGS. 2b, 2c, 2f and FIGS. 8 and 9). At 6 weeks after myocardial infarction, Myh7, Nppa, and Nppb, associated with adult cardiomyocyte remodelling, were upregulated in control ischaemic heart failure but not SalvCKO (FIG. 10a).

Figure 10F:
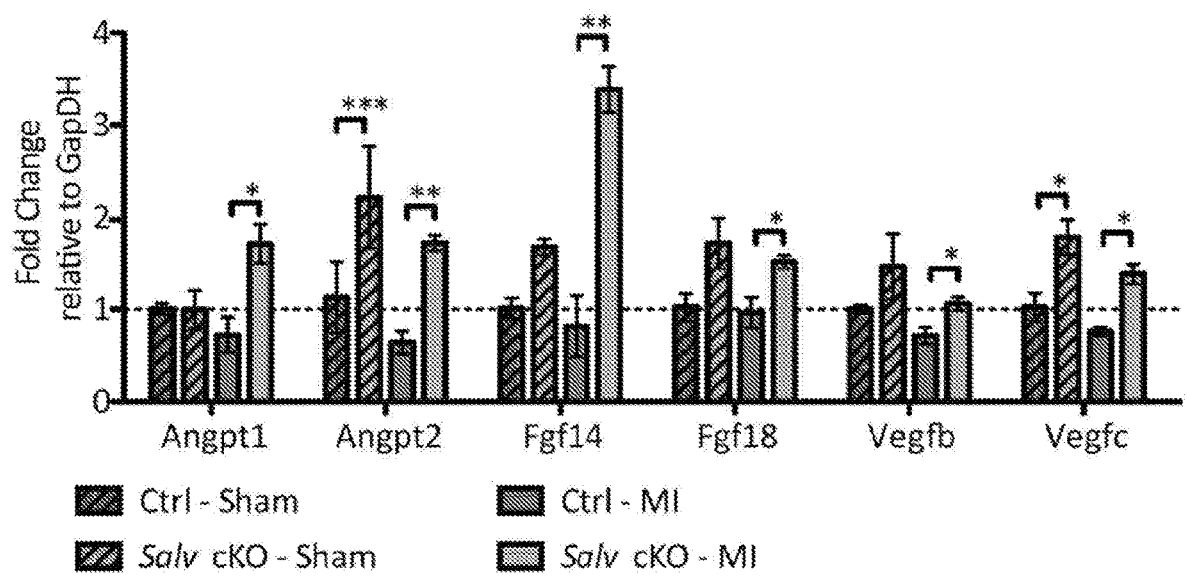
Figure 11A:
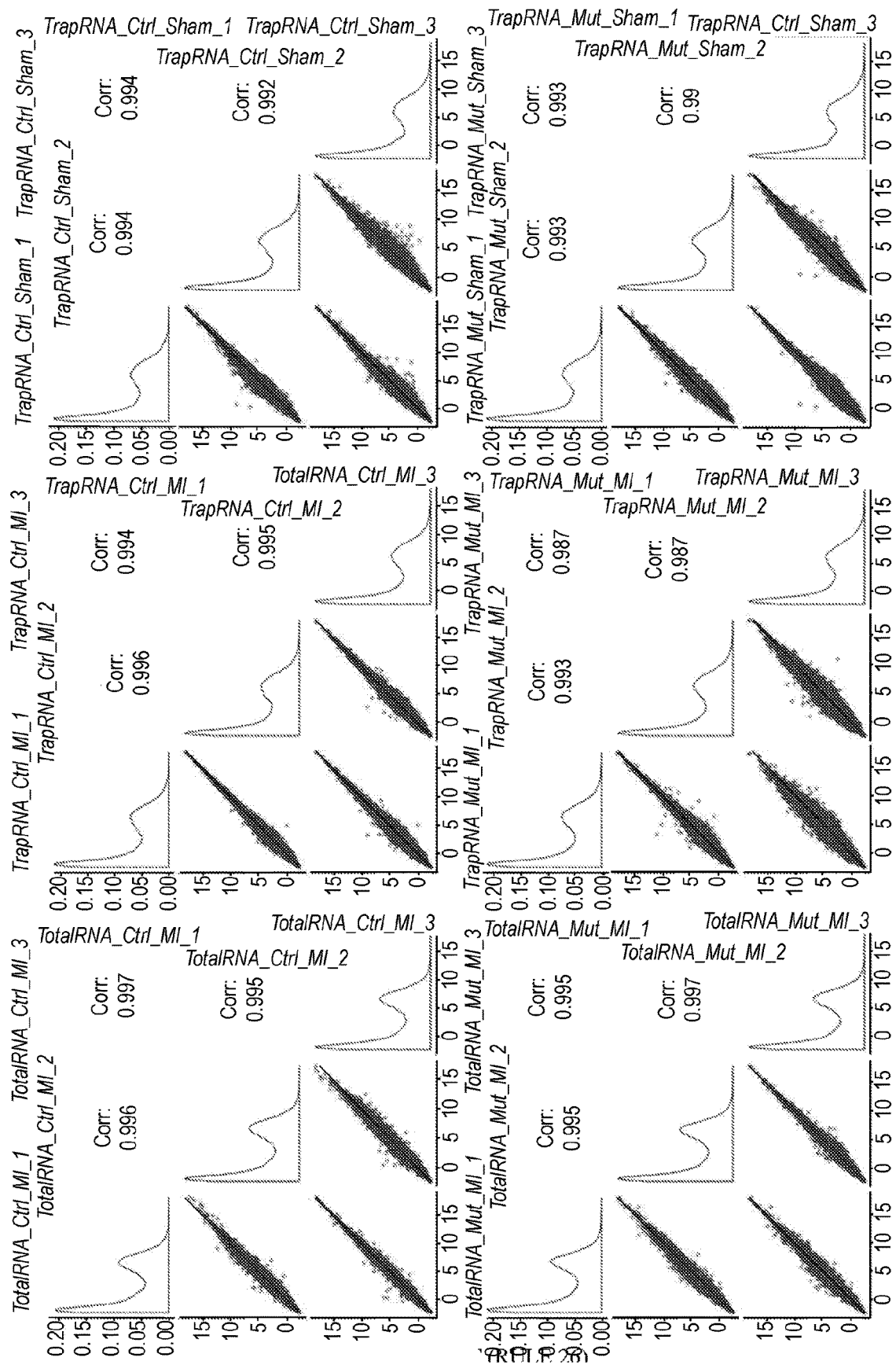
Figure 11B:
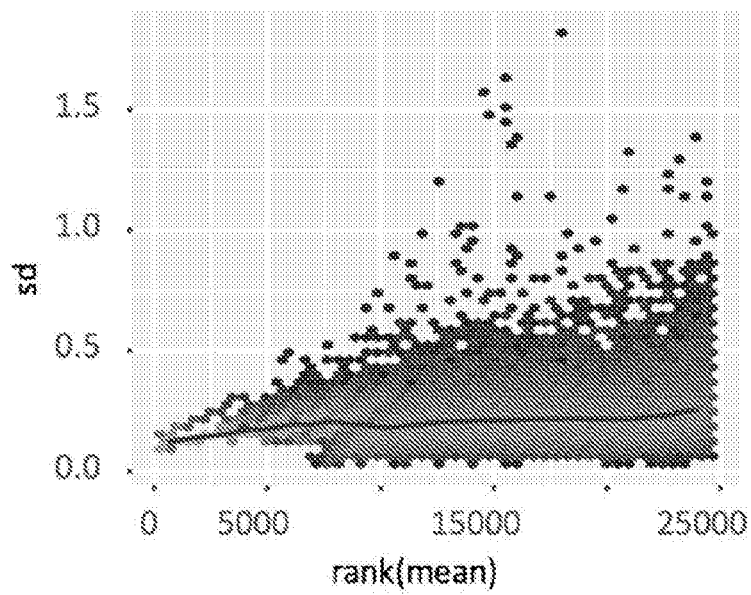
Figure 11C:
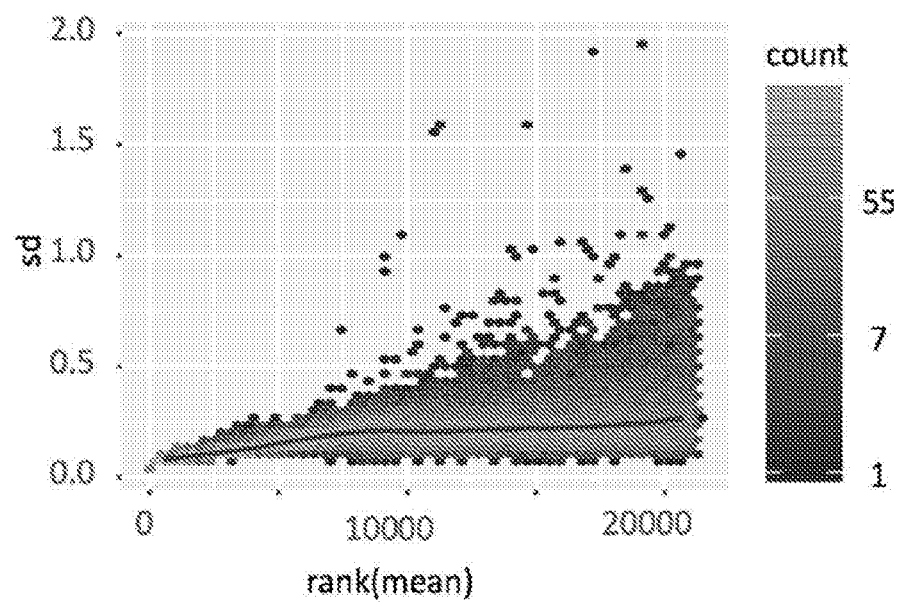
Figure 11D:
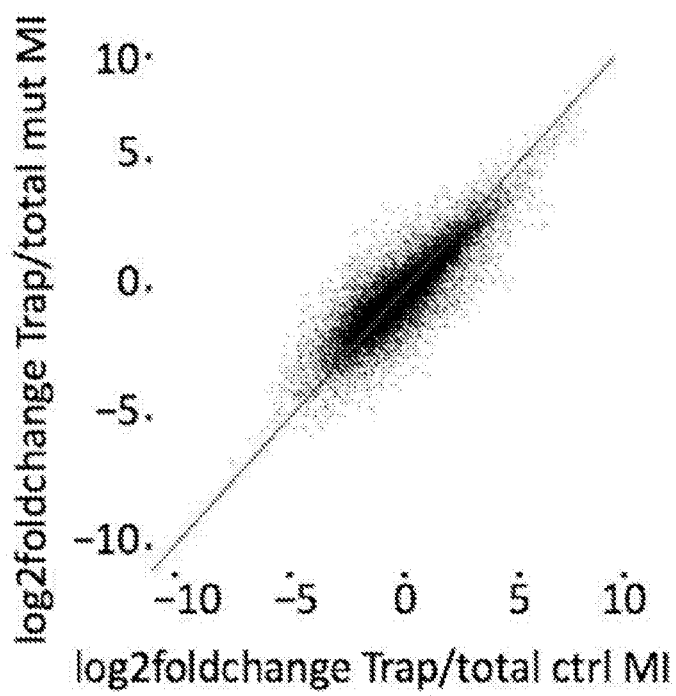

SalvCKO hearts at 6 weeks after myocardial infarction had a threefold increase in border zone capillary density and increased endothelial markers isolectin B4 and CD-31 compared with controls (FIGS. 10b-10e). Cardiomyocyte-enriched translating ribosomal affinity purification (TRAP) RNA revealed increased vasculogenesis genes encoding angiopoietins, fibroblast growth factors, and vascular endothelial growth factors in cardiomyocytes of SalvCKO hearts with myocardial infarction (FIG. 10f).

Figure 2K:
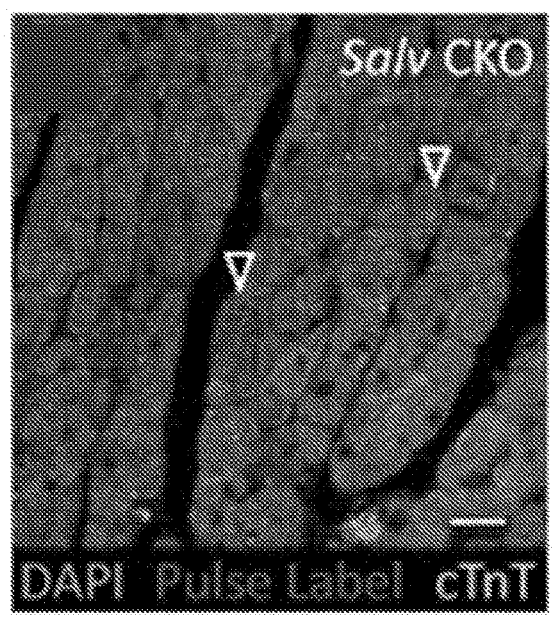
Figure 2L:
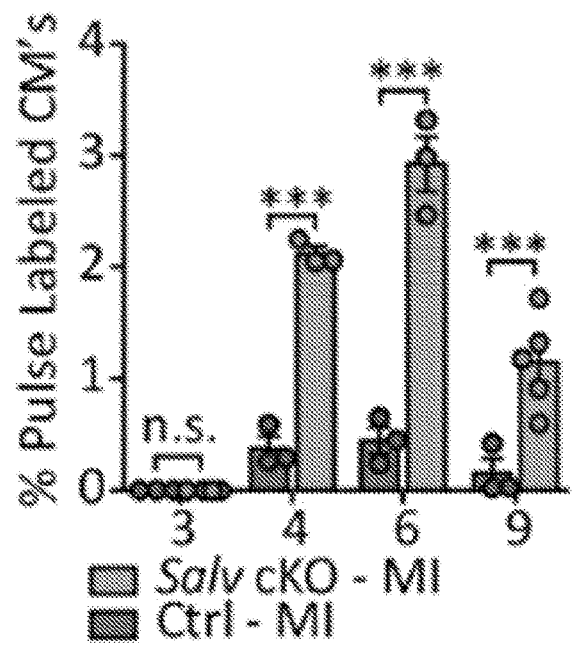
Figure 2M:
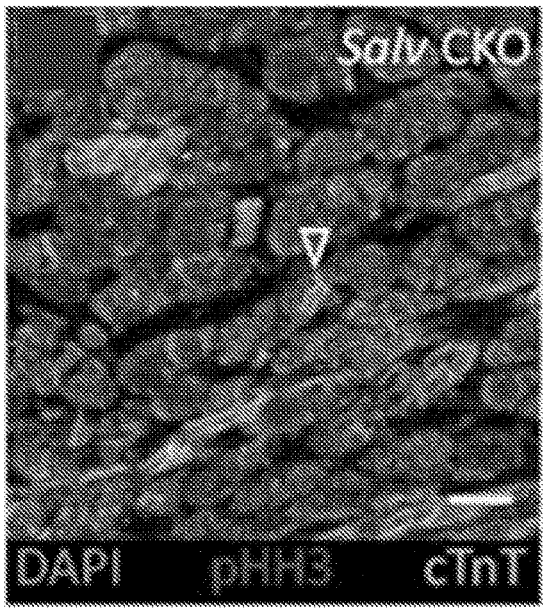
Figure 2N:
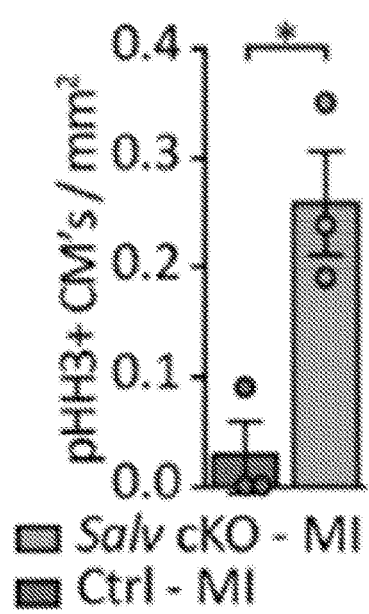

The inventors found SalvCKO hearts had 2-3% cardiomyocyte 5-ethynyl-2'-deoxyuridine (EdU) incorporation at 4 and 6 weeks after myocardial infarction and approximately 1% at 9 weeks after myocardial infarction (FIGS. 2k, 2l). Phospho-histone H3 immunofluorescence revealed M-phase cardiomyocytes 9 weeks after myocardial infarction in SalvCKO mice with myocardial infarction (FIGS. 2m, 2n). Hence, cardiomyocyte cell-cycle entry was diminished in SalvCKO mouse hearts at 9 weeks after myocardial infarction as cardiomyocytes repaired the tissue defect.

Figure 2O:
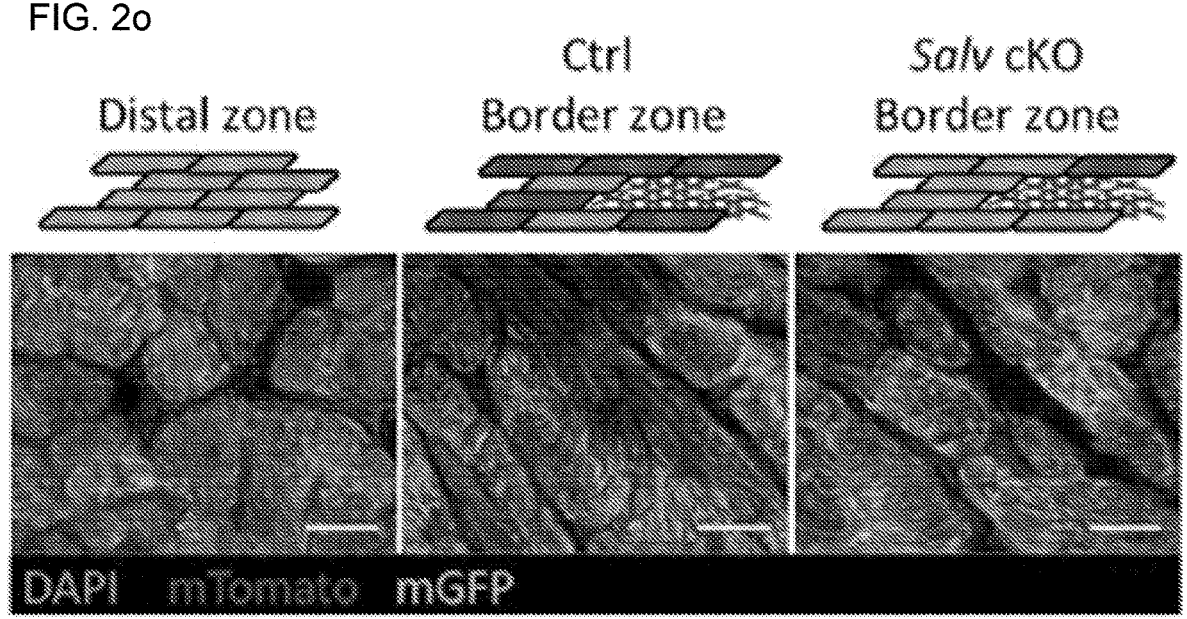
Figure 2P:
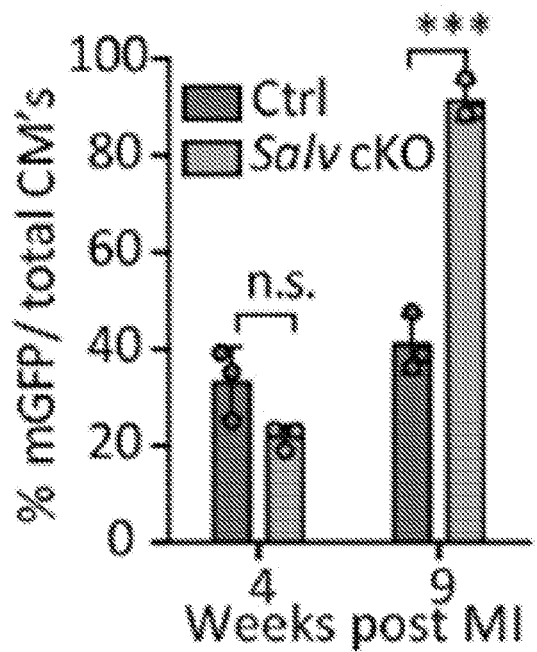
Figure 2Q:
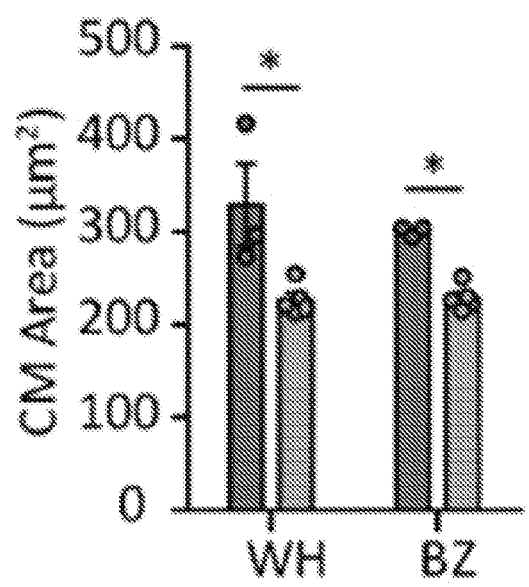
Figure 3A:
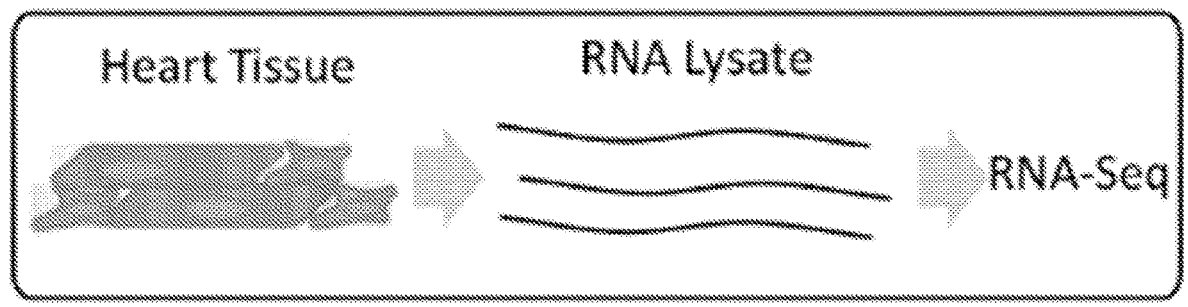
Figure 3B:
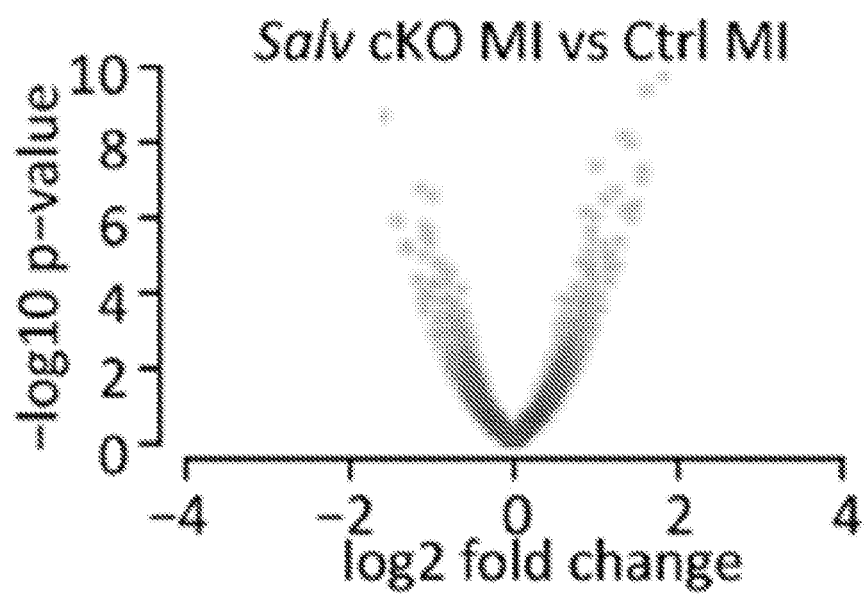
Figure 3C:
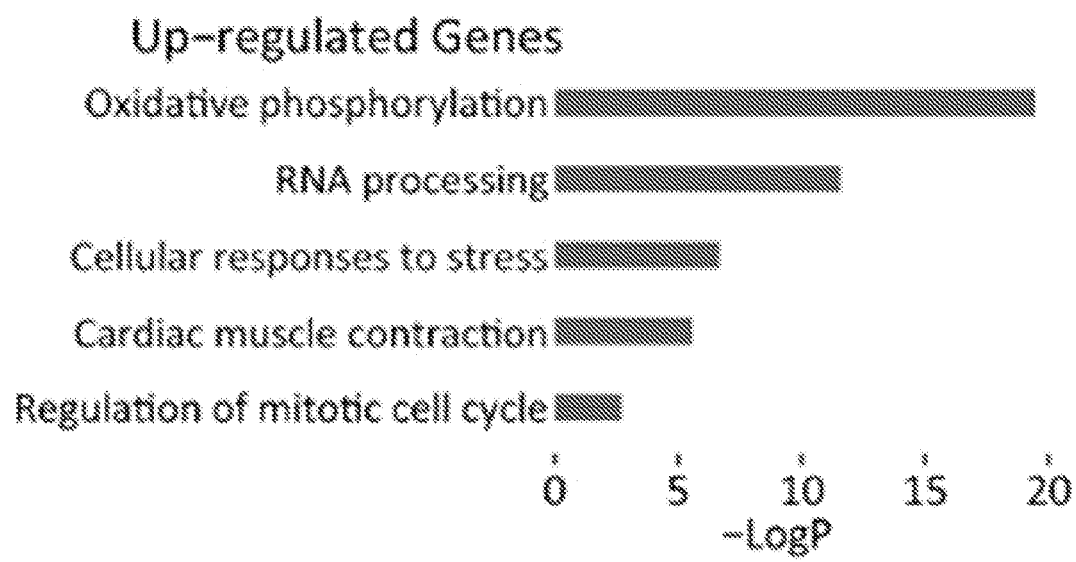

Lineage tracing by αMHC-mcm transgene revealed mosaic labelling of border zone cardiomyocytes (FIG. 2o). At 4 weeks after myocardial infarction, the border zone had equivalent numbers of GFP-positive cardiomyocytes in controls (33%±7%) and SalvCKO (22%±2%) (FIGS. 2o, 2p). At 9 weeks after myocardial infarction, GFP-positive border zone cardiomyocytes were enriched in SalvCKO (control myocardial infarction 41%±6%, SalvCKO myocardial infarction 91%±4%) (FIGS. 3o, 3p), indicating that most new, reparative border zone cardiomyocytes are derived from pre-existing cardiomyocytes rather than Myh6-negative cardiac stem cells that would be GFP-negative. Cardiomyocyte cross-sectional area was reduced, suggesting a more primitive phenotype, in SalvCKO mice at 9 weeks after myocardial infarction (Doupe et al., 2012) (FIG. 2q).

Figure 3D:
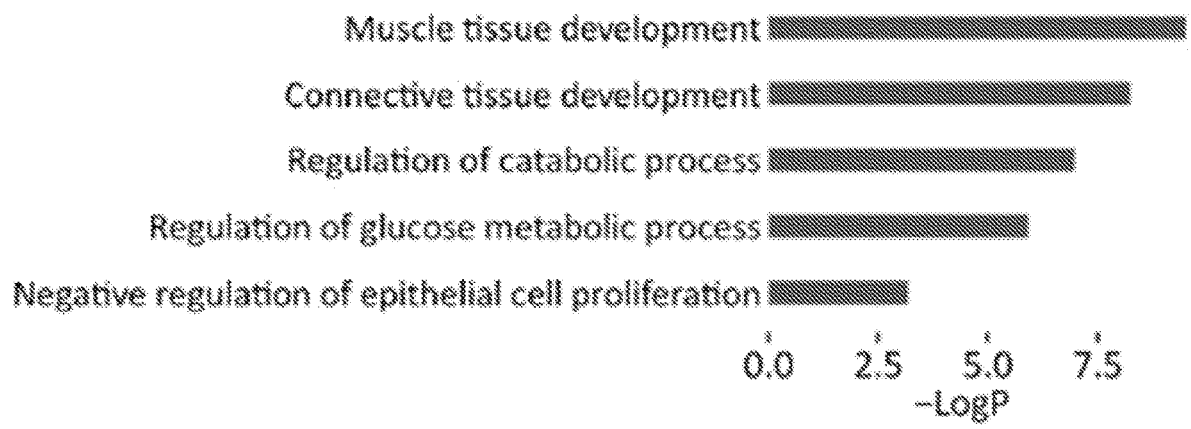

The inventors sequenced total-RNA and TRAP RNA from border zone 6 weeks after myocardial infarction (FIGS. 11a-11d). Total-RNA revealed upregulated genes (N=932) in SalvCKO border zone were involved in oxidative phosphorylation, RNA processing, stress response, cell cycle, and muscle contraction (FIGS. 3a-3c and FIG. 4a). SalvCKO border zone downregulated genes (N=792) included developmental genes, glycolytic metabolism genes, and connective tissue genes including pro-fibrotic genes such as Tgfbr1, Ctgf, and Pdgfrδ(FIG. 3d and FIG. 12a) (Leask, 2015; Ponten et al,. 2005).

Figure 3E:
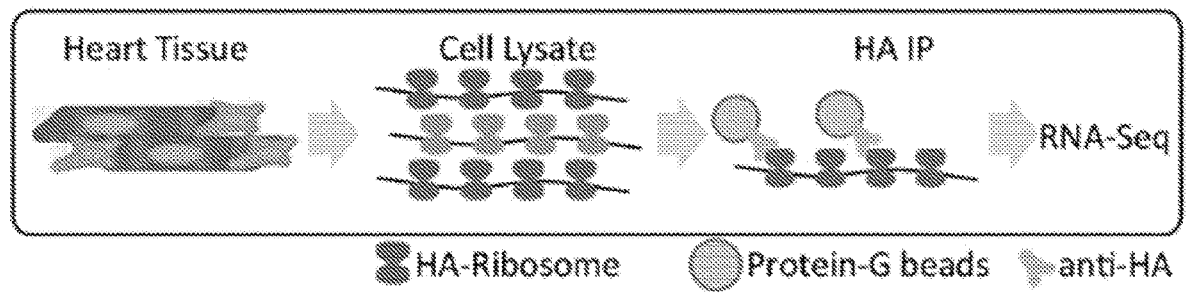
Figure 12A:
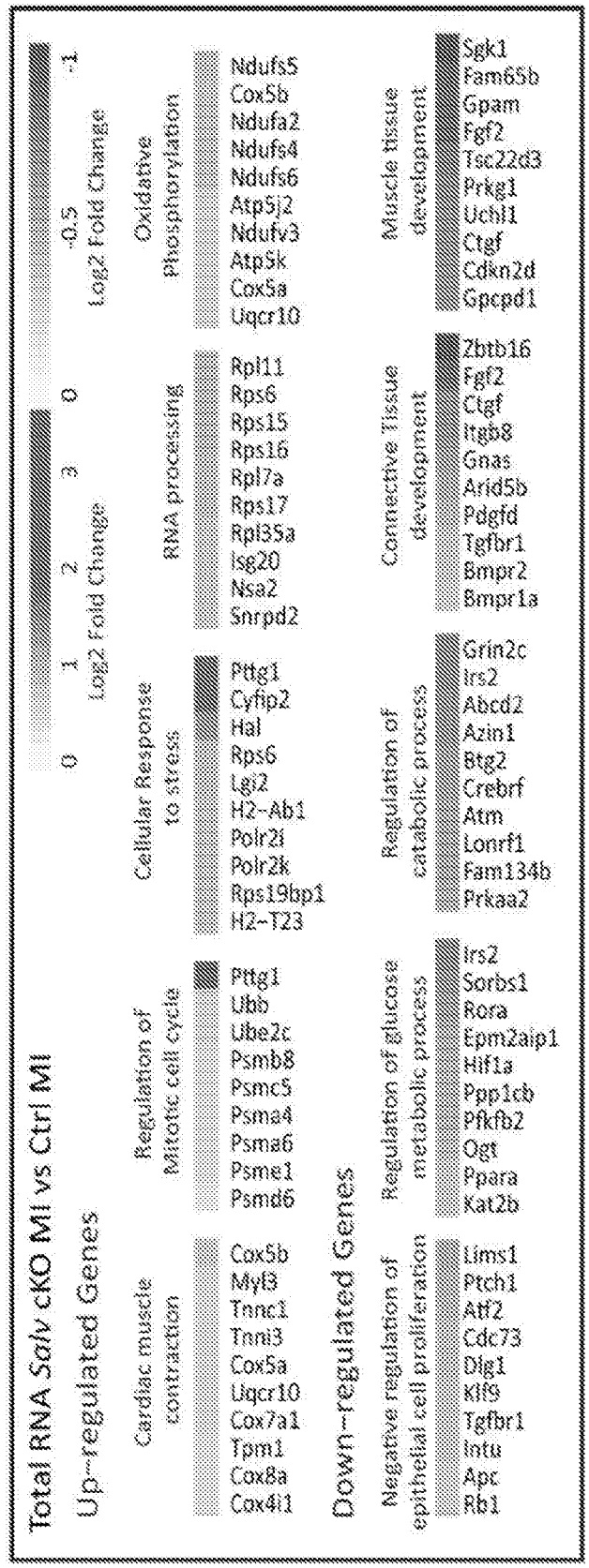
Figure 12B:
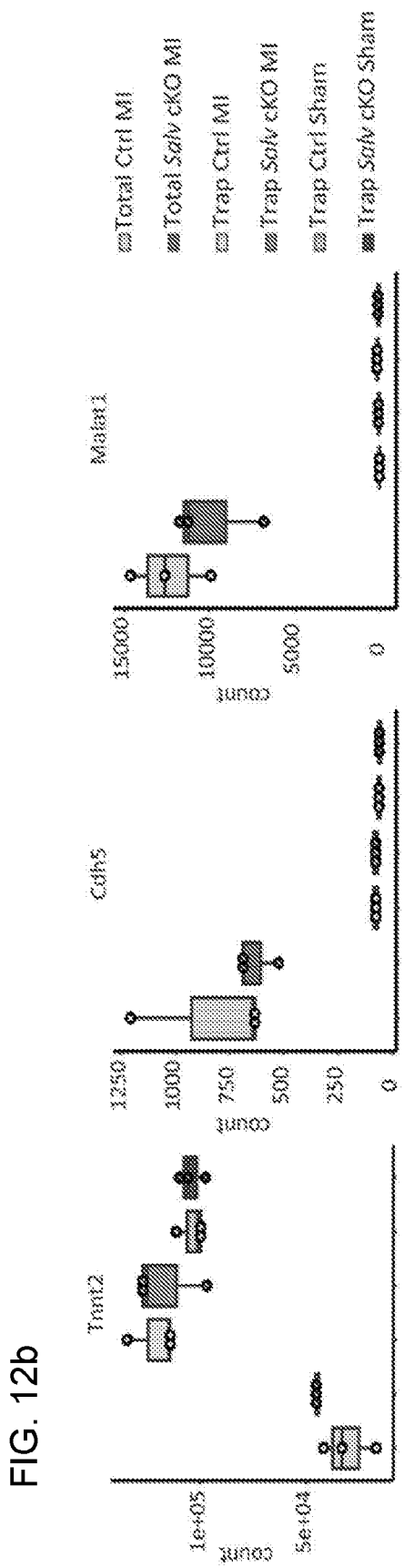
Figure 12C:
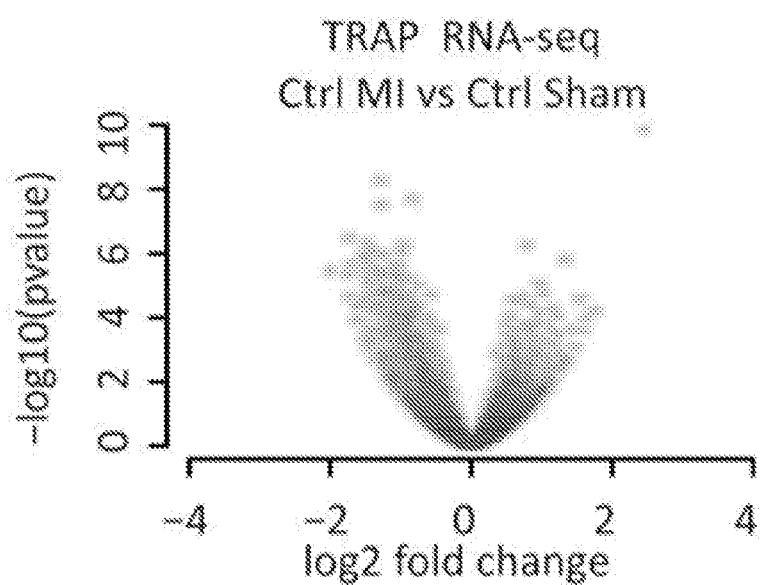

Comparison of TRAP sequencing (TRAP-seq), enriched for cardiomyocyte translating RNA (FIGS. 3e, 3f), with total-RNA-seq revealed that TRAP-seq was enriched for cardiomyocyte genes and depleted of non-cardiomyocyte genes (FIGS. 3g-3i and FIG. 12b). Non-translated LncRNAs were depleted from TRAP-seq (FIG. 4i and FIG. 12b). Comparison of total-RNA-seq with TRAP-seq revealed total RNA and TRAP-seq groups clustered separately (FIG. 3j). SalvCKO myocardial infarction TRAP-seq clustered closely to control sham TRAP-seq data, revealing that Hippo-deficient cardiomyocytes expressed a genetic program similar to control shams (FIG. 3j).

Figure 12D:
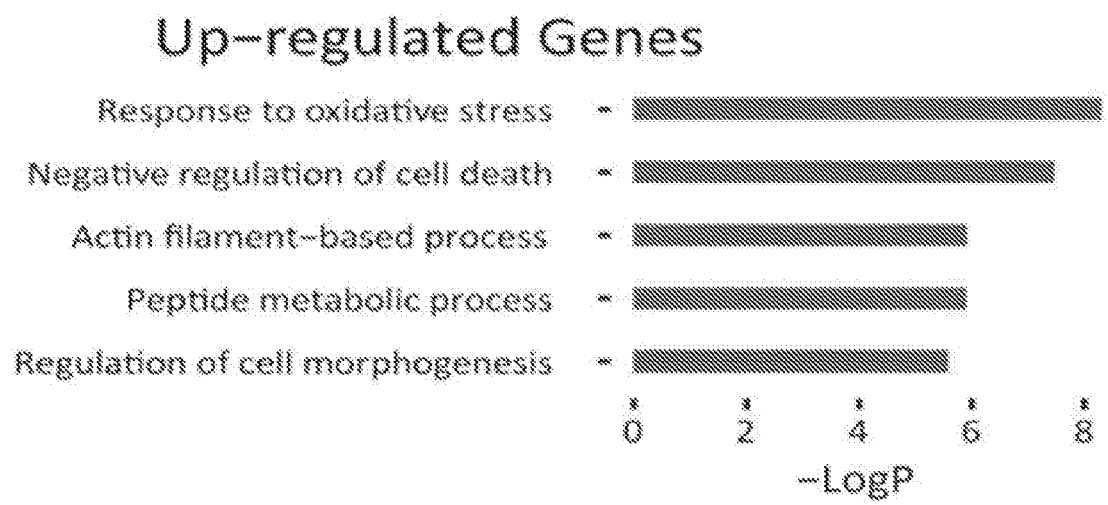
Figure 12E:
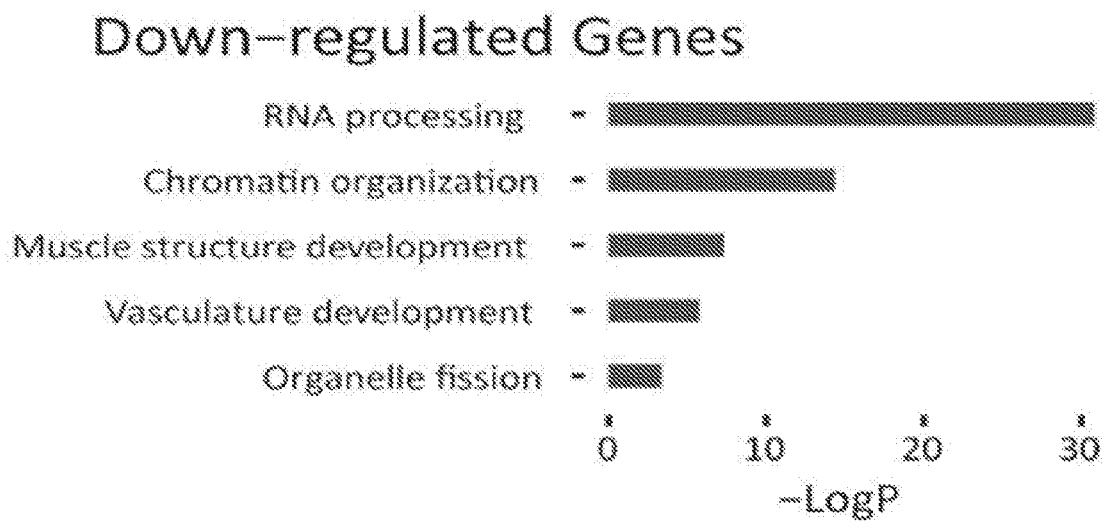
Figure 12F:
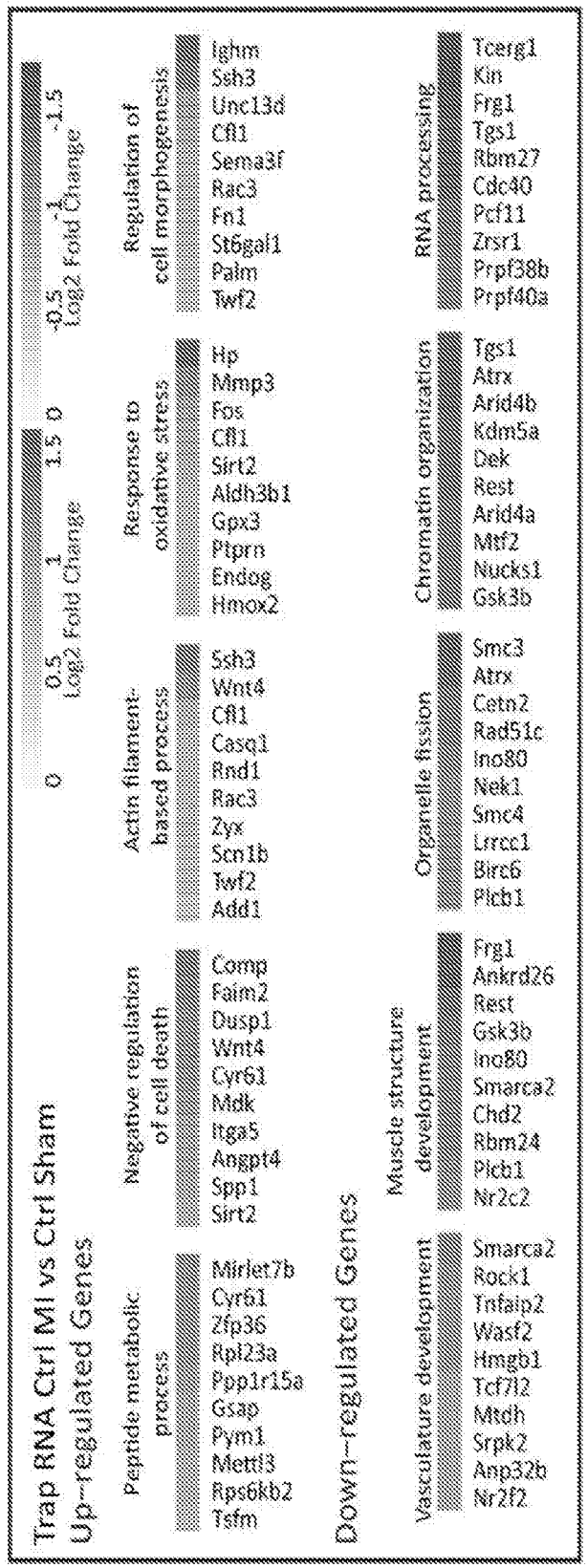
Figure 12G:
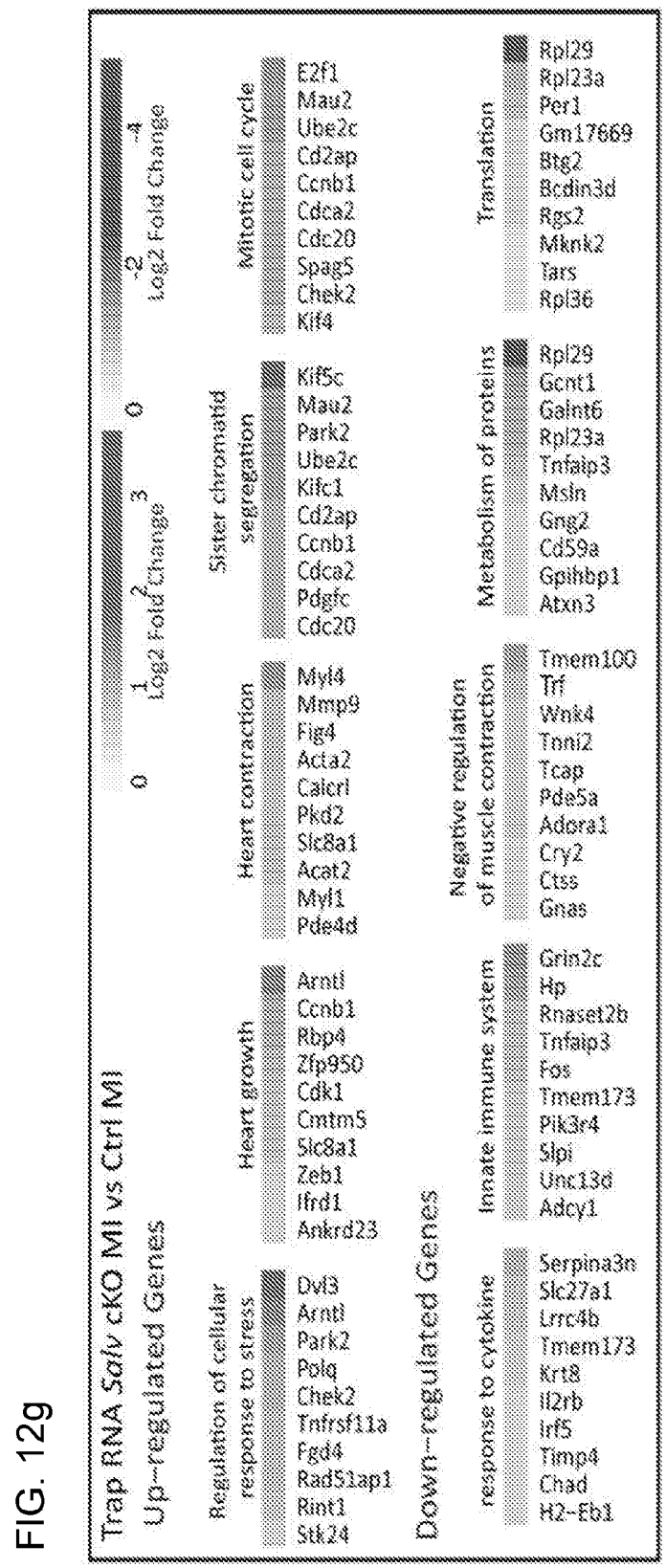
Figure 13D:
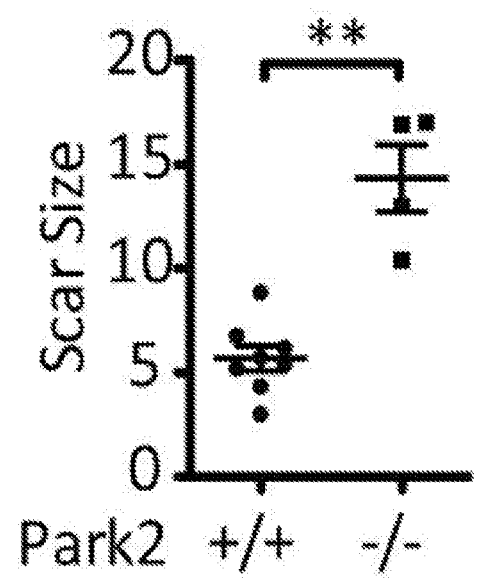
Figure 13E:
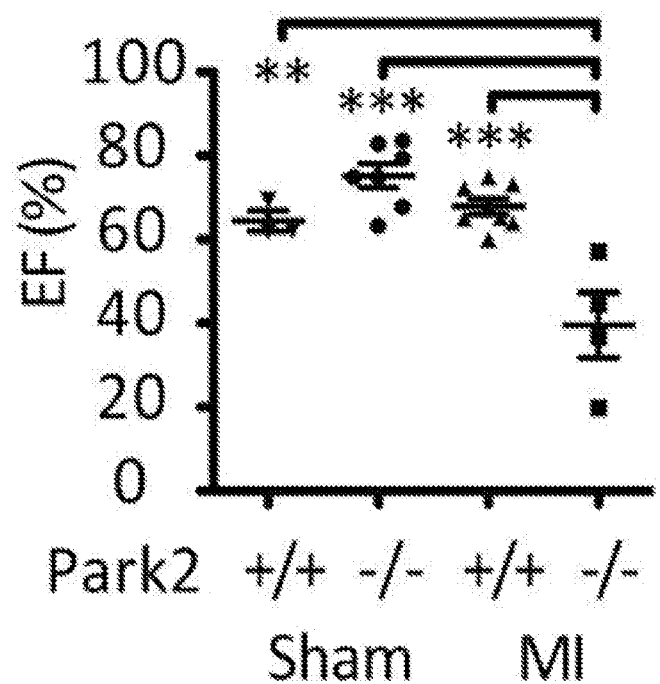
Figure 13F:
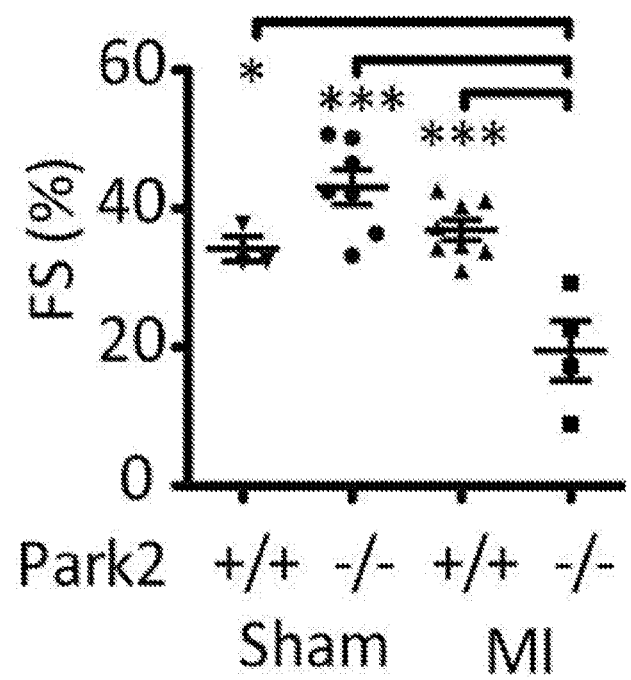
Figure 13G:
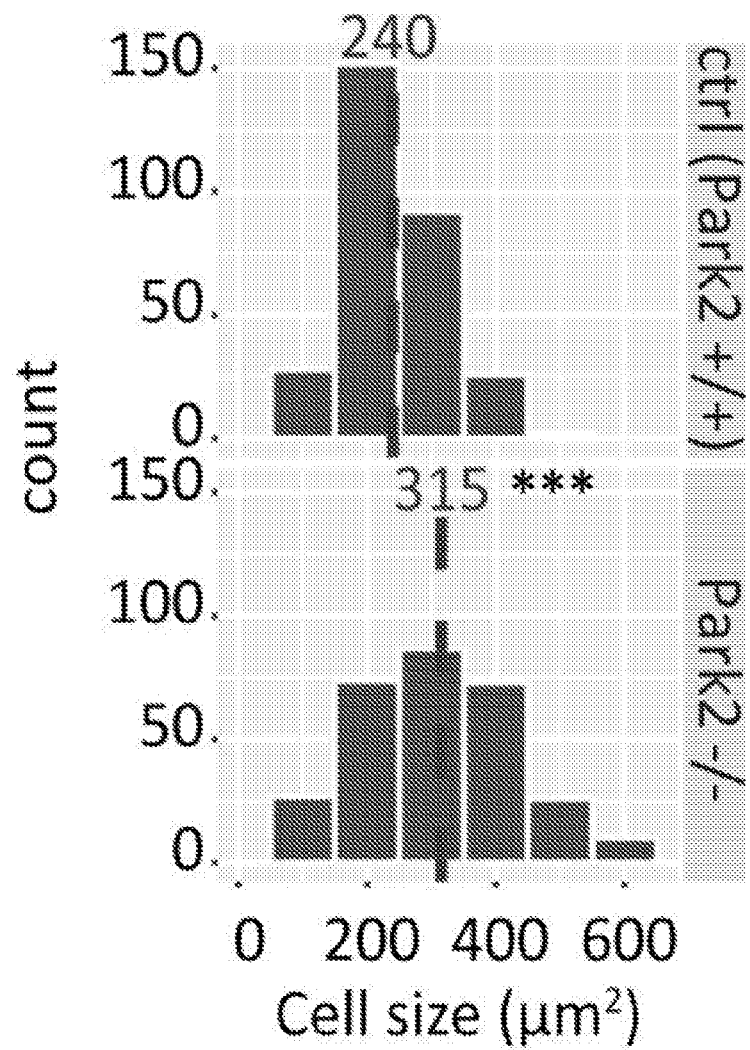
Figure 13H:
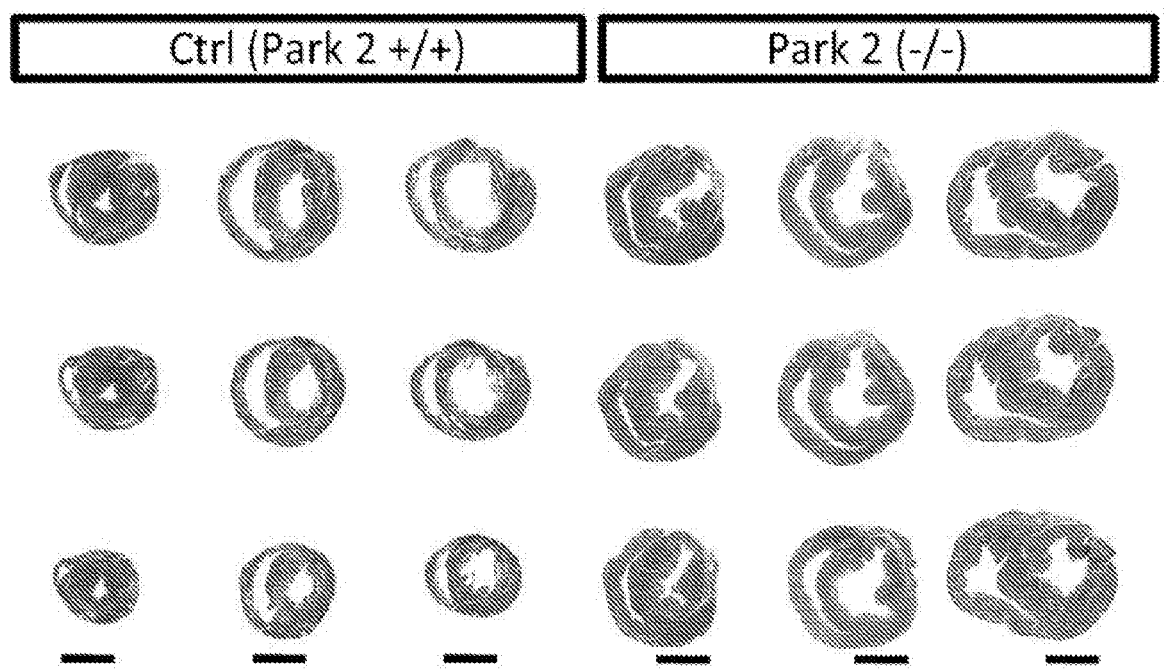
Figure 13I:
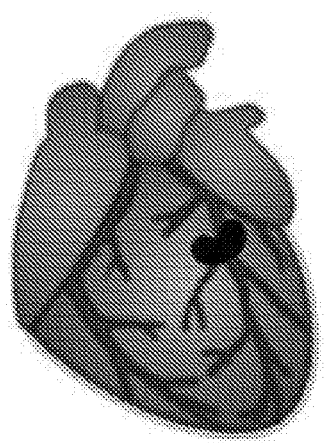
Figure 13I:
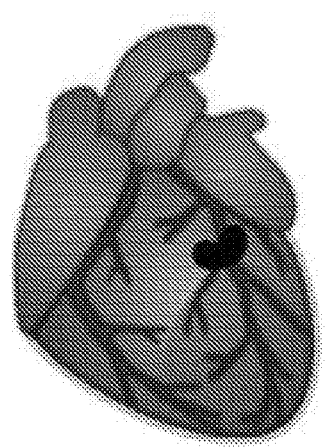

The inventors compared TRAP-seq of control after myocardial infarction and control sham to determine changes in cardiomyocyte gene expression during ischaemic heart failure after myocardial infarction (FIGS. 12c-12f). One upregulated category was peptide metabolic processes including Akt1, which exacerbates heart failure when chronically expressed (Heineke et al., 2006) (FIGS. 12d, 12f). Genes that respond to reactive oxygen species, such as GstP1 and Gpx3, were upregulated as was Clusterin, known to be upregulated in human heart failure (Meredith et al., 2016). Another upregulated gene category, actin-filament-based process, is consistent with observations that cytoskeletal components are upregulated in human heart failure (Kostin et al., 2000). Downregulated gene categories included chromatin organization and blood vessel development, consistent with known gene expression changes in heart failure (Kim et al., 2016; Jesup and Brozena, 2003 (FIGS. 12e, 12f). Genes involved in organelle fission, such as mitochondrial fission, were downregulated. Disruption of mitochondrial fission and fusion can lead to heart failure (Marin-Garcia and Akhmedov, 2016) (FIG. 12e, 12f).

Figure 3F:
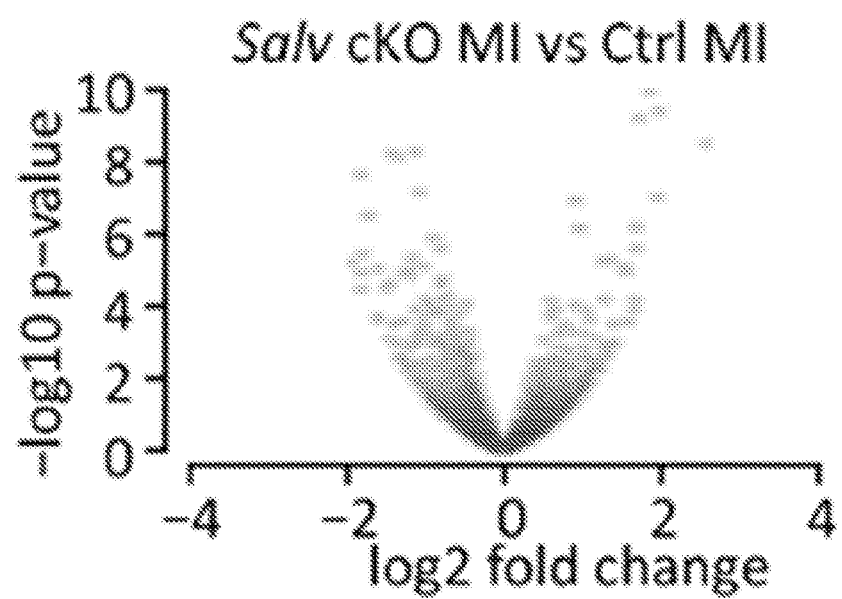
Figure 3G:
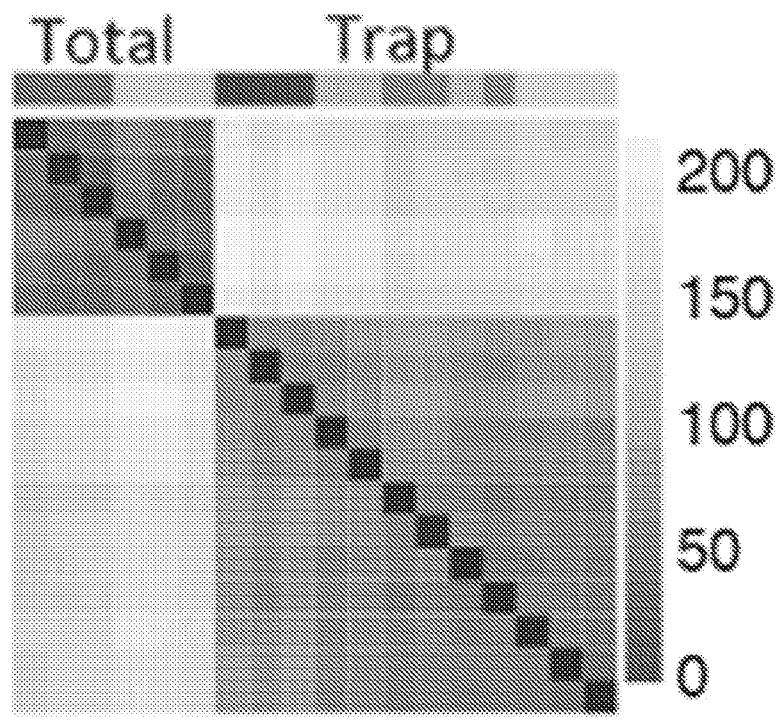
Figure 3H:
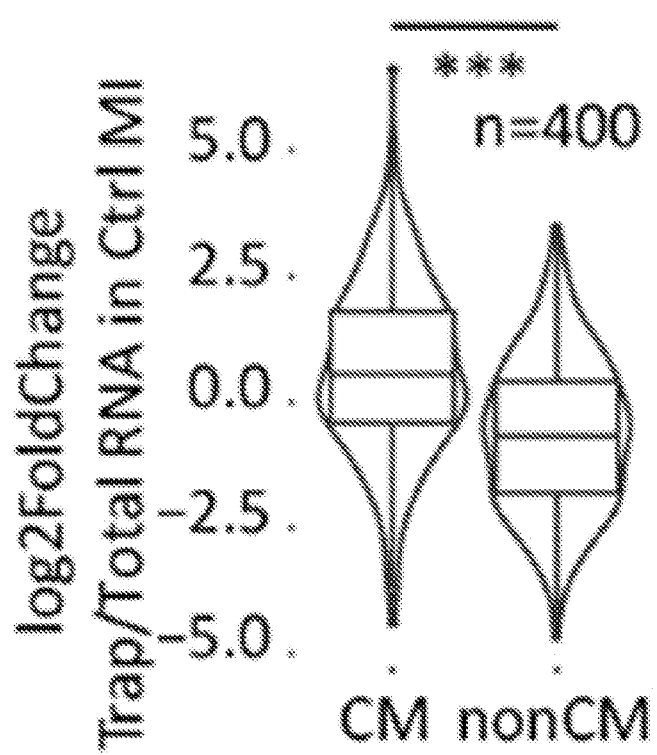
Figure 3I:
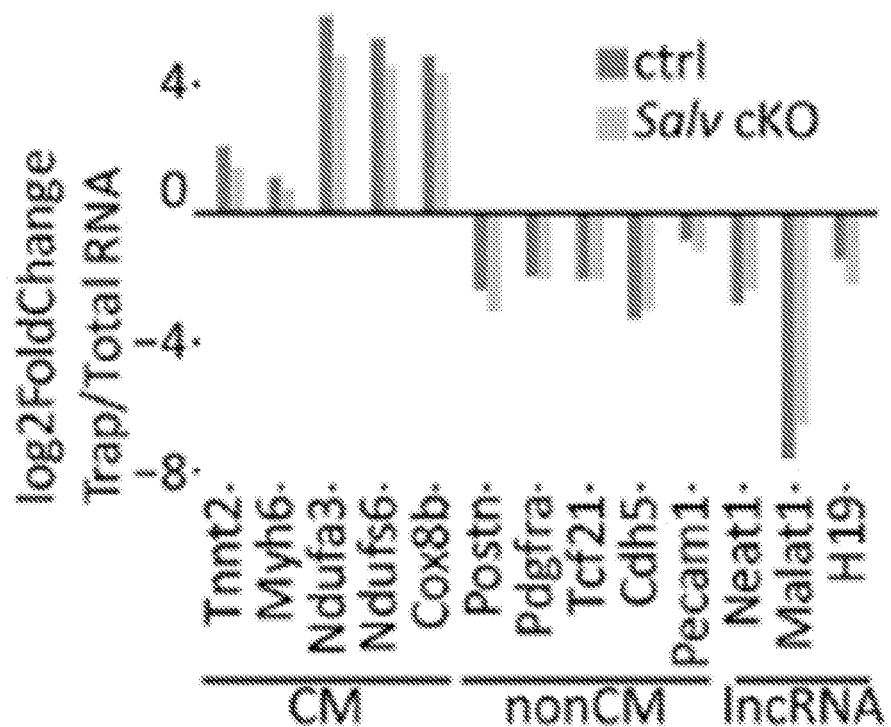
Figure 3J:
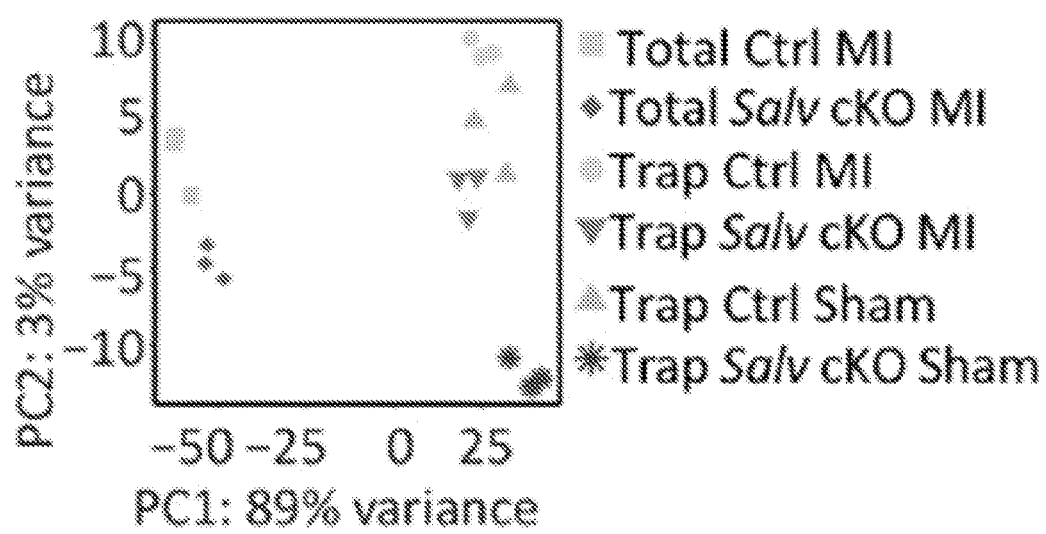
Figure 3K:
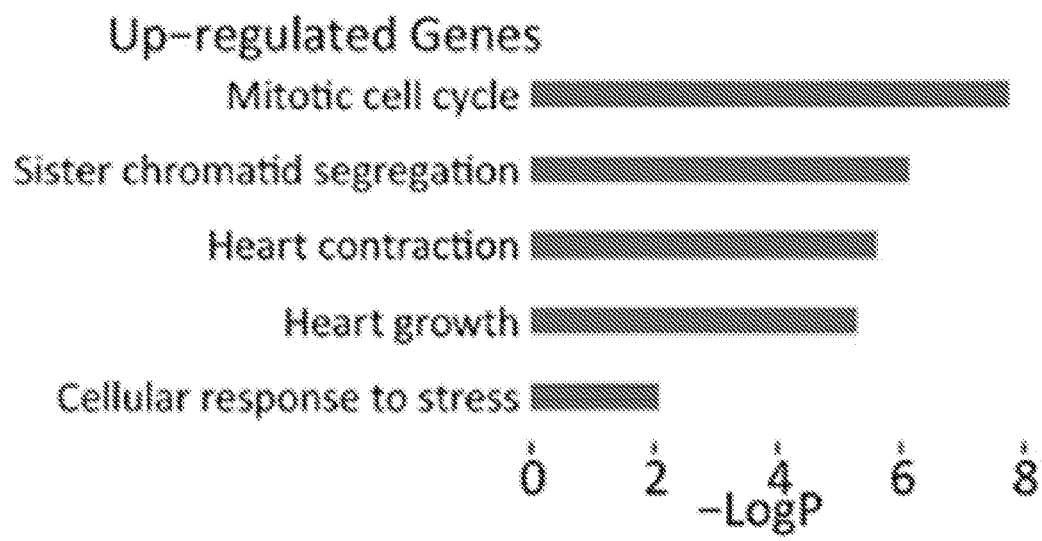
Figure 3I:
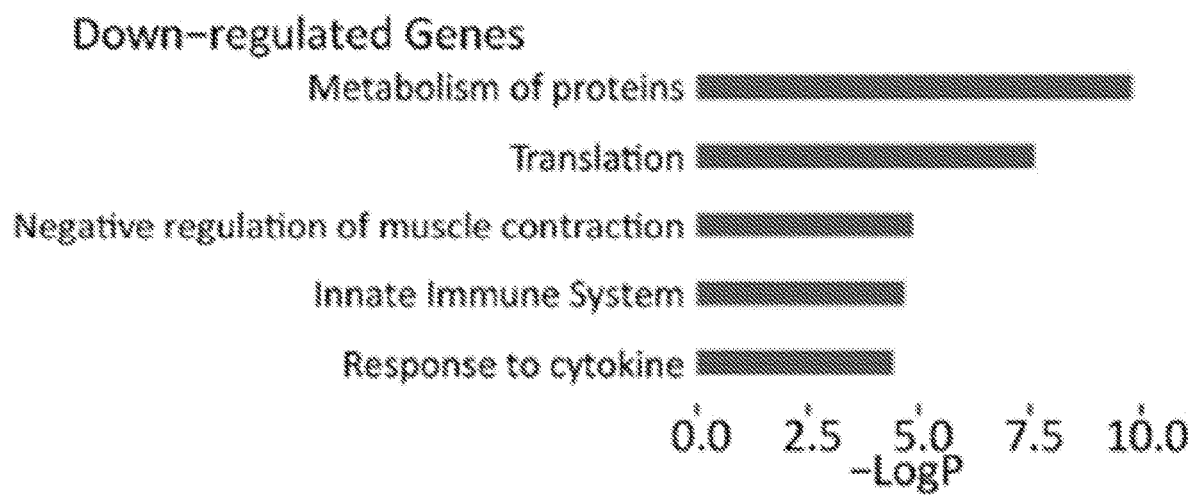

The inventors compared TRAP-seq between SalvCKO and control hearts after myocardial infarction (FIG. 3f). Upregulated genes (N=365) included cell cycle genes, consistent with previous studies (FIG. 3k and FIG. 12g) (Heallen et al., 2013; Morikawa et al., 2015). Other upregulated genes included genes involved in heart contraction, heart growth, and cellular response to stress, suggesting that SalvCKO cardiomyocytes were recovering the mature cardiomyocyte phenotype with an effective stress response. Downregulated genes (N=261) in SalvCKO cardiomyocytes after myocardial infarction included translation, protein metabolism including the ubiquitin-proteosome pathway, and inflammation (FIG. 3l and FIG. 12g), indicating that inflammation and misfolded protein response were more effectively resolved in SalvCKO myocardial infarction.

Figure 3M:
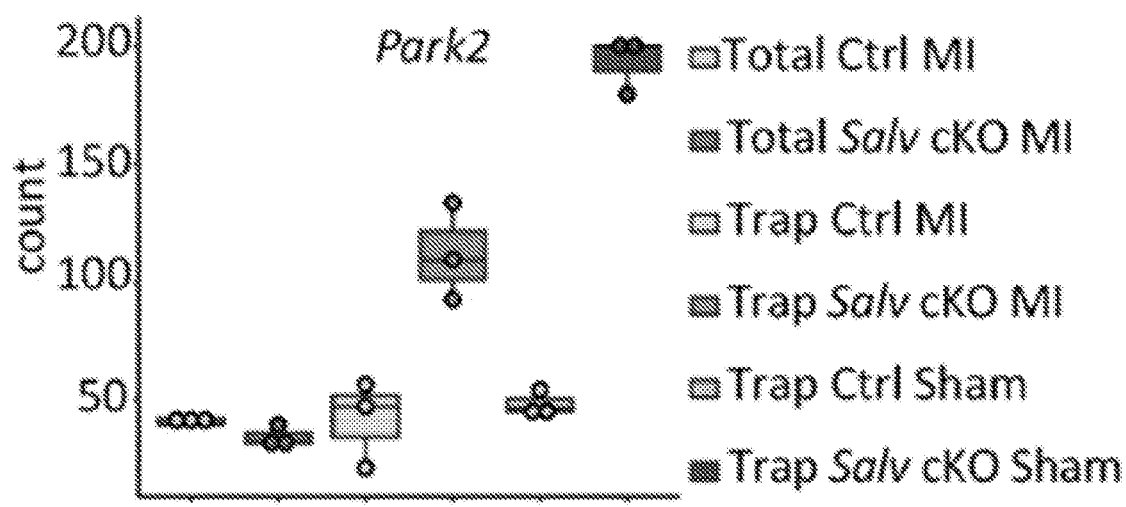

Park2, a Yap target gene, was upregulated in SalvCKO TRAP-seq (FIG. 3m) (Morikawa et al., 2015). Park2 encodes a ubiquitin ligase involved in mitochondrial quality control, a surveillance mechanism to recycle damaged mitochondria (Dorn, 2016). Park2 is recruited to damaged mitochondria to direct mitochondria into mitophagy pathway that salvages damaged mitochondria. Park2 protein levels are reduced in human heart failure (FIGS. 4a, 4b and FIGS. 13a-13c). Moreover, Park2 deletion in adult mice results in dilated cardiomyopathy after myocardial infarction (Kubli et al., 2013). Similar to Yap, Park2 is required for cardiac regeneration at postnatal day 1 (P1) (FIGS. 13d-13i) (Xin et al., 2013).

Figure 14A:
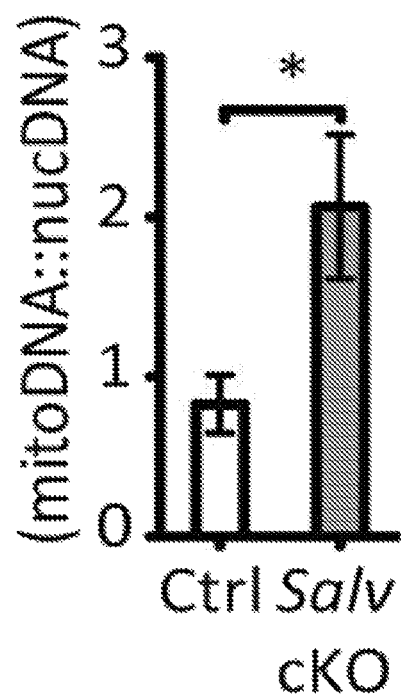
Figure 14B:
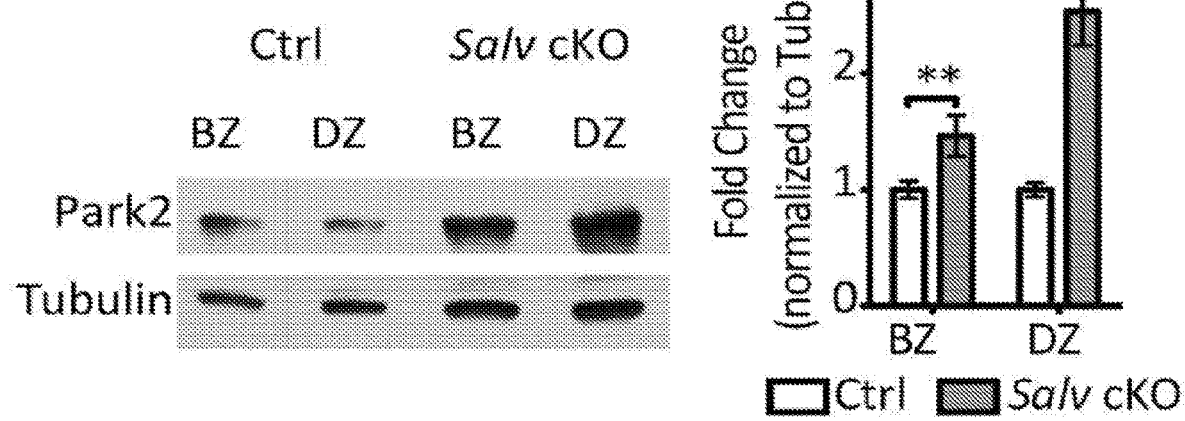
Figure 14C:
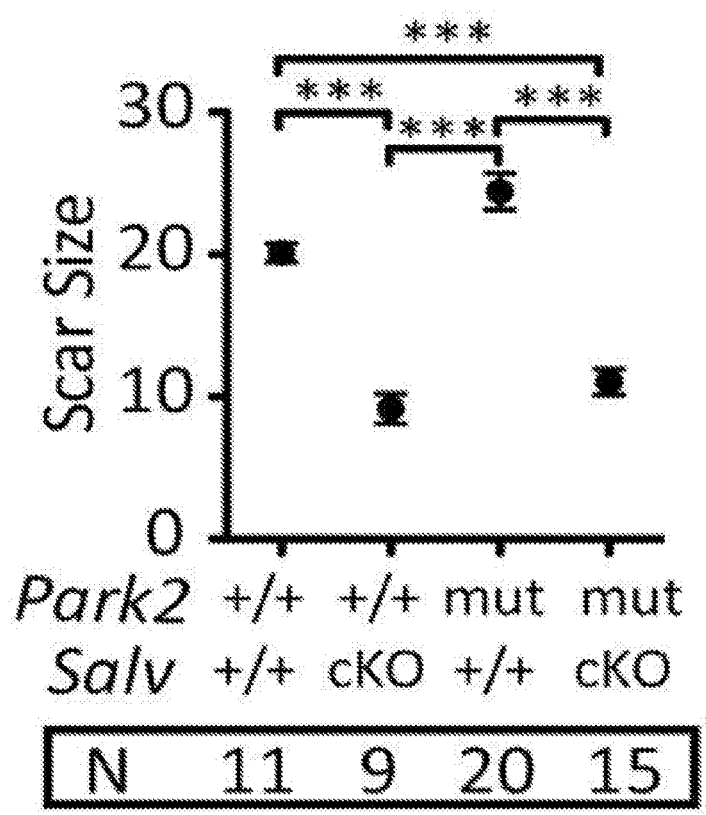
Figure 14D:
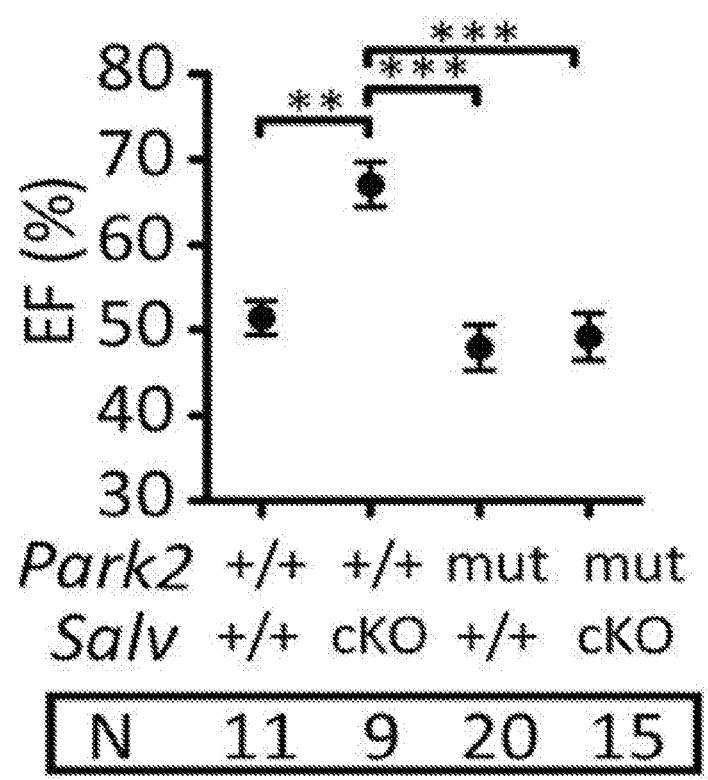
Figure 14E:
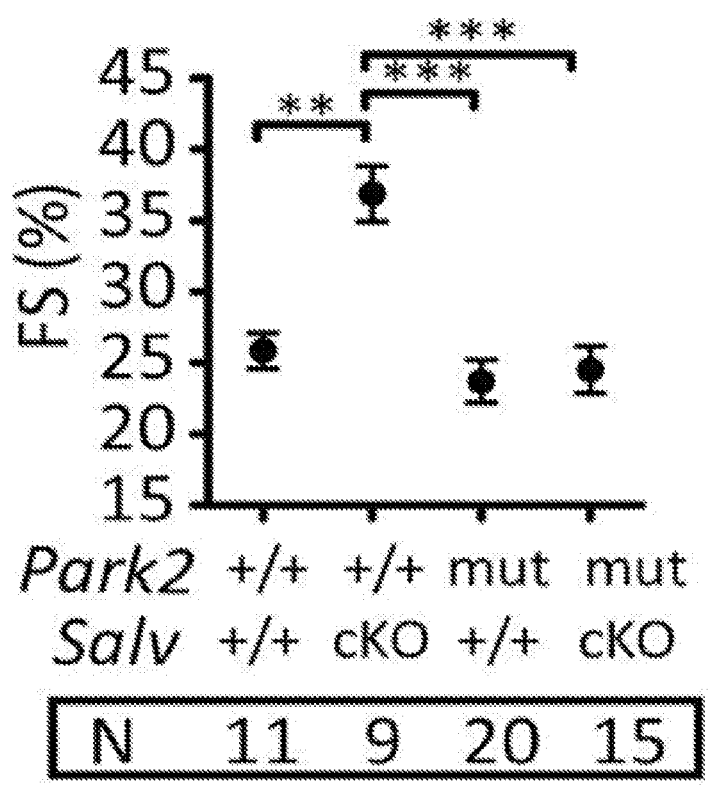
Figure 14F:
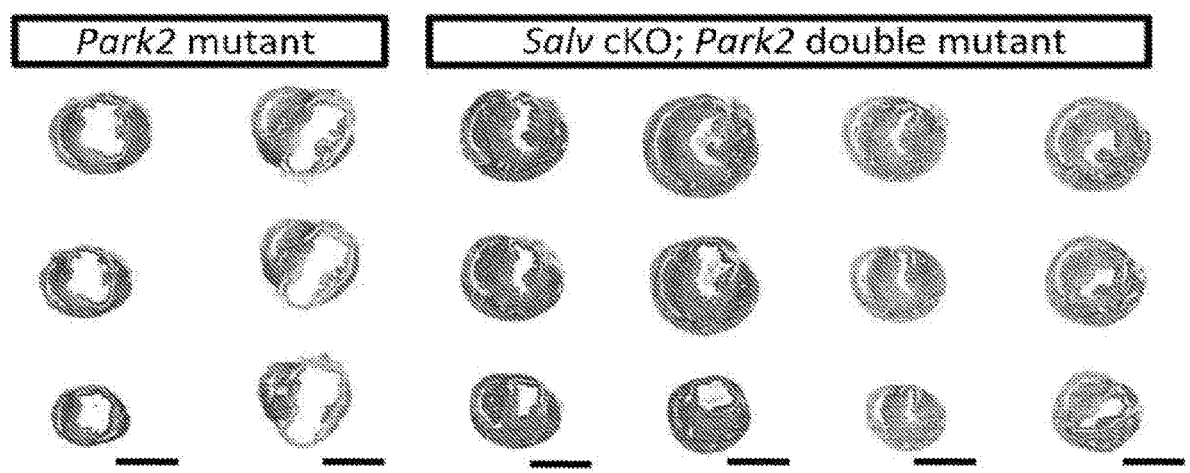
Figure 14G:
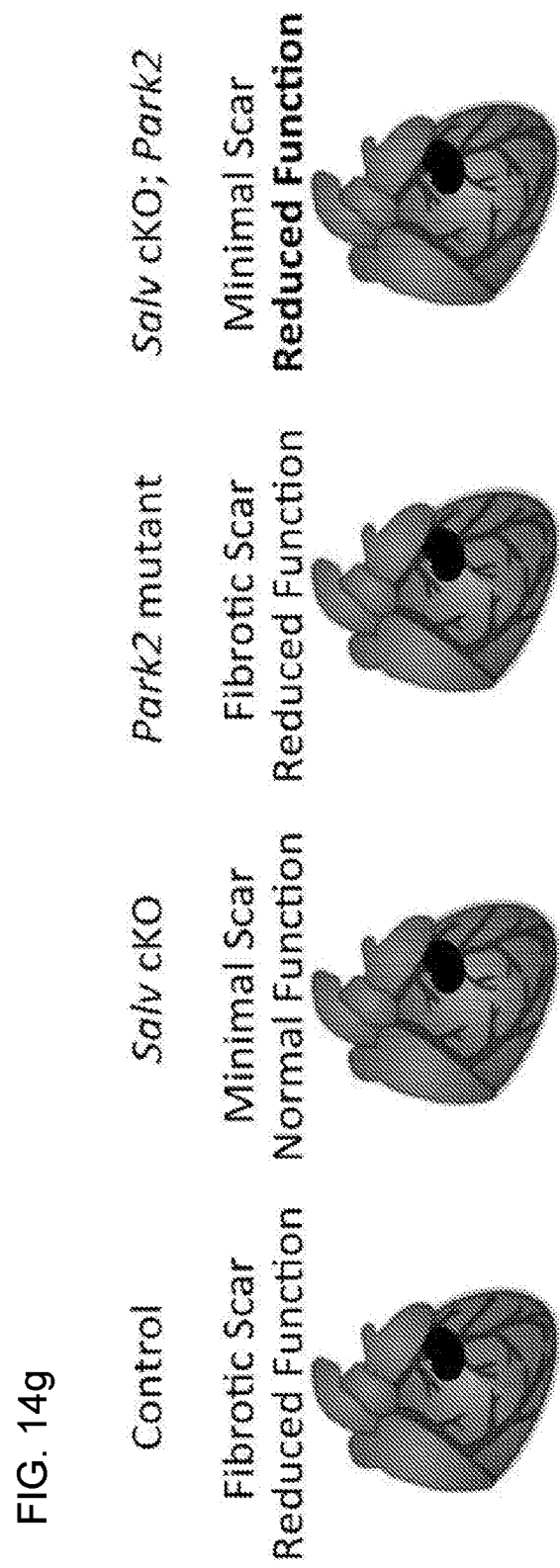

We tested whether Park2 was required for regeneration in P8 SalvCKO (Hellen et al., 2013). After P8 myocardial infarction, SalvCKO had higher mitochondrial DNA content and increased Park2 protein levels (FIGS. 14a, 14b), suggesting that mitochondrial quality control is more active in SalvCKO hearts. Park2 was required for recovery of myocardial function in SalvCKO hearts after P8 myocardial infarction (FIGS. 14c-14g). Interestingly, although myocardial function was reduced, fibrosis did resolve in SalvCKO; Park2$^{-/-}$ hearts, indicating a myocardial-autonomous requirement for Park2 in SalvCKO neonatal hearts (FIGS. 14c, 14g).

Figure 4A:
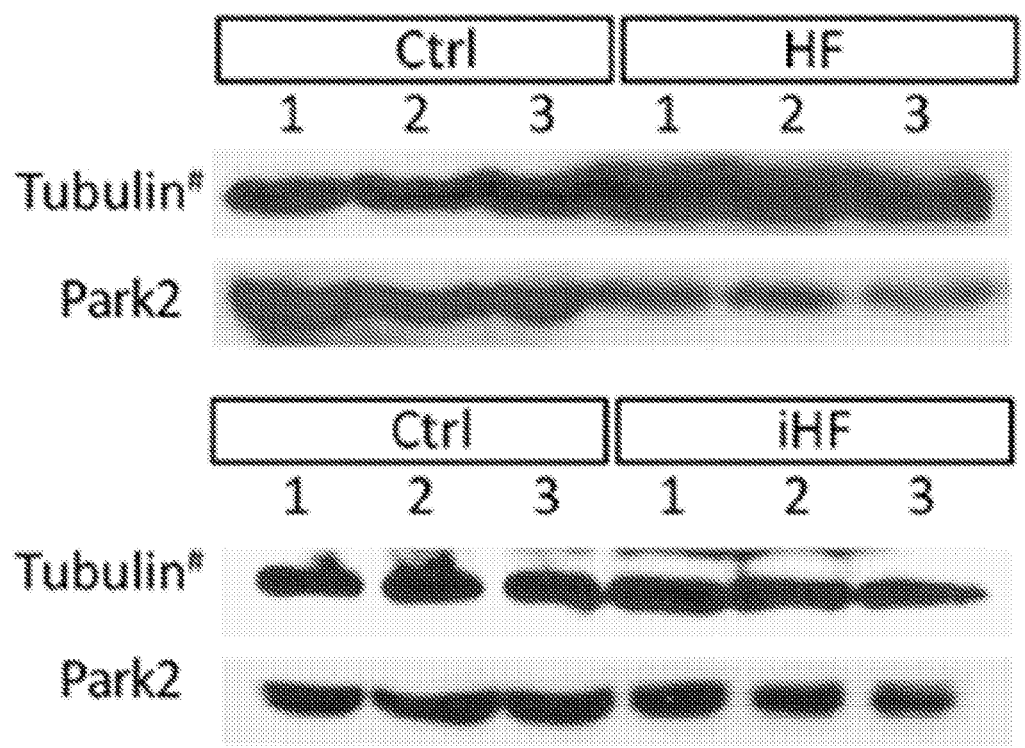
FIGS. 4a-4o. Park2 in heart failure and Salv gene therapy. 4a, 4b Western blot human heart (4a) and quantification (4b), Mann-Whitney U-test. (Tubulin #from FIG. 1a, b (n=6); additional samples FIG. 5). 4c, 4d, Fractional shortening (4c) and ejection fraction (4d); ANOVA, Tukey's pairwise post-hoc test, control sham*, control myocardial infarction†, SalvCKO sham*, SalvCKO myocardial infarction* repeated from FIGS. 2a-2c. 2e, 2f, Masson's trichrome: Park2$^{-/-}$ (n=3) (4e) Park2$^{-/-}$; SalvCKO (n=4) (4f) 9 weeks after myocardial infarction. Scale bar, 2 mm 4g, Left ventricle scar size, control myocardial infarction‡, SalvCKO myocardial infarction‡ repeated from FIG. 2f (n=7). 4h, Knockdown (KD) efficiency of Salv siRNA, n=3 per group. i, AAV9 diagram.
Figure 4B:
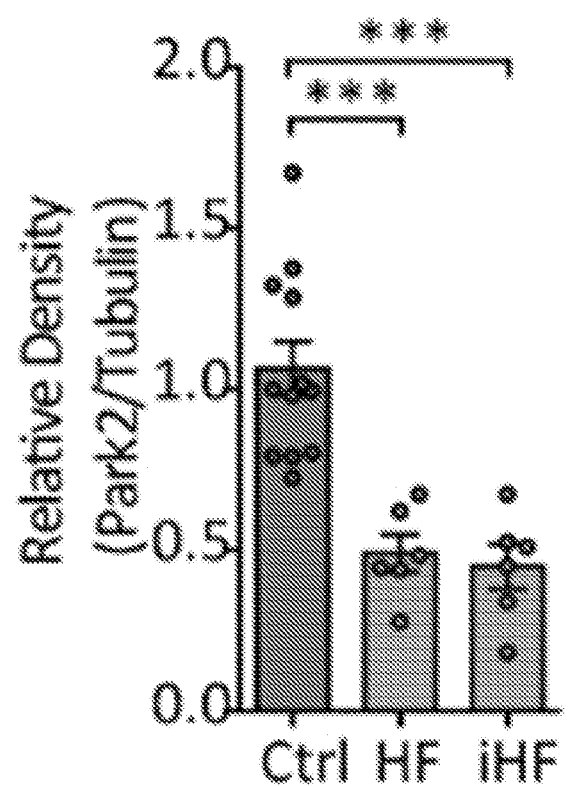
FIG. 4i discloses SEQ ID NOS 36-38, respectively, in order of appearance. 4j, 4k, Fractional shortening (4j) and ejection fraction (4k); ANOVA, Tukey's pairwise post-hoc test. 4l, 4m, GFP expression Salv knockdown border zone (n=3 per group), Low GFP (arrow); scale bar, 50 µm. 4n, 4o, EdU-labelled cardiomyocytes (arrow); scale bar, 50 µm; quantification (4o), n=3 per group, Mann-Whitney U-test. Data are mean±s.e.m., P>0.05 non-significant (NS), *P<0.05, P<0.01, *P<0.001.
Figure 4C:
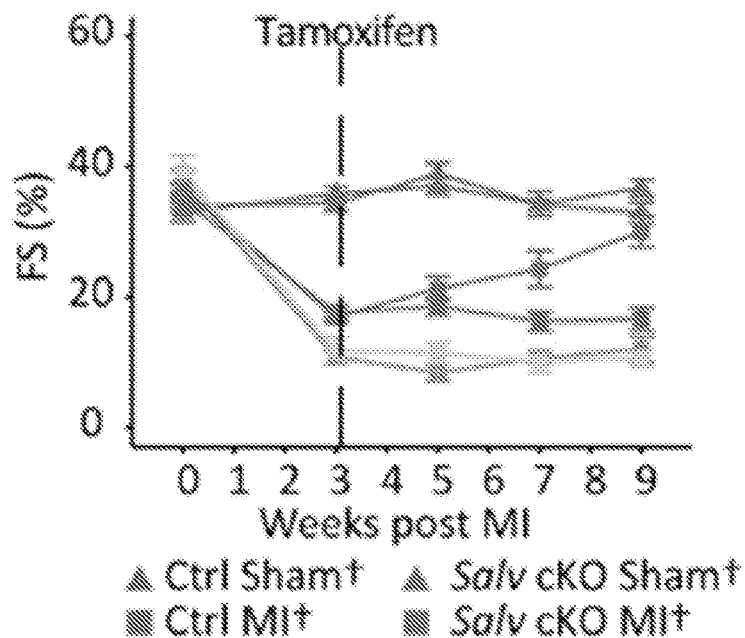
Figure 4D:
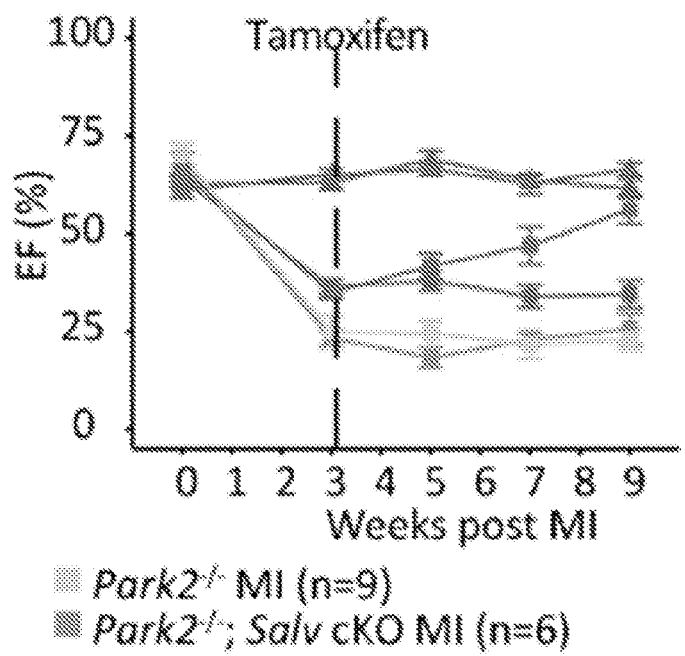
Figure 4E:
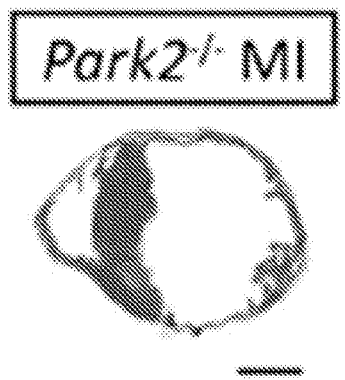
Figure 4F:
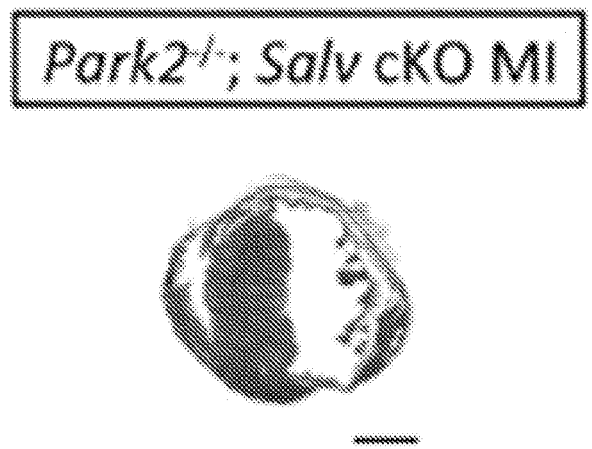
Figure 4G:
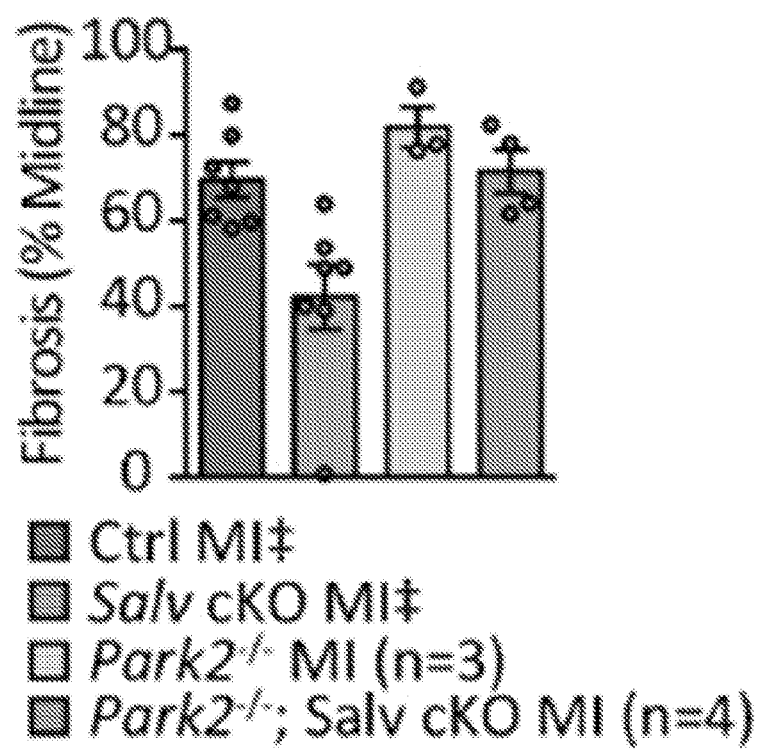

Park2 was required for cardiac function recovery in adult ischaemic heart failure (FIGS. 4c-4g). Compared with SalvCKO mice, double-mutant SalvCKO;Park2$^{-/-}$ mice did not recover contractile function (FIGS. 4c, 4d). However, unlike SalvCKO adult hearts and SalvCKO;Park2$^{-/-}$ neonatal hearts (FIG. 14c), scar failed to resolve in SalvCKO; Park2$^{-/-}$ adult hearts, revealing a differential requirement for Park2 in neonatal versus adult fibrosis resolution (FIGS. 4e-4g).

Figure 4H:
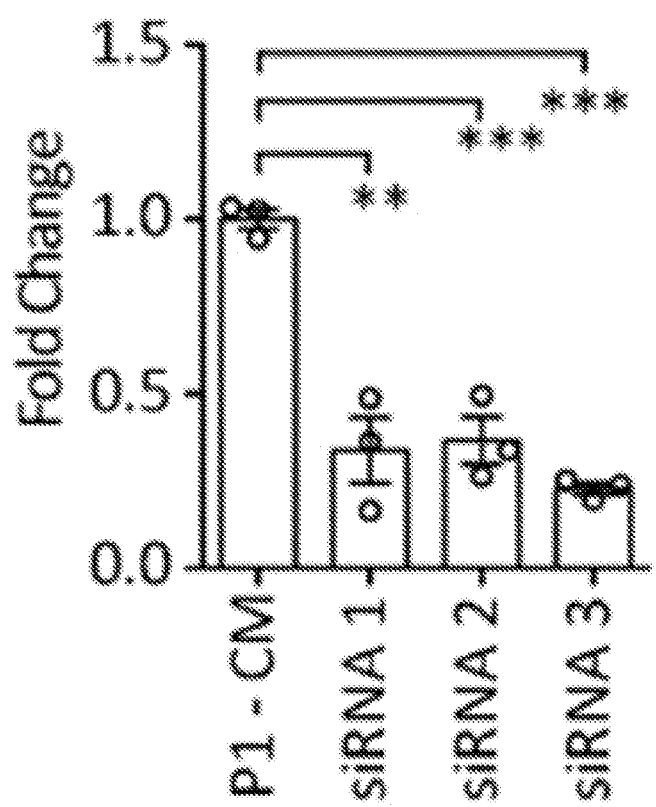
Figure 4I:
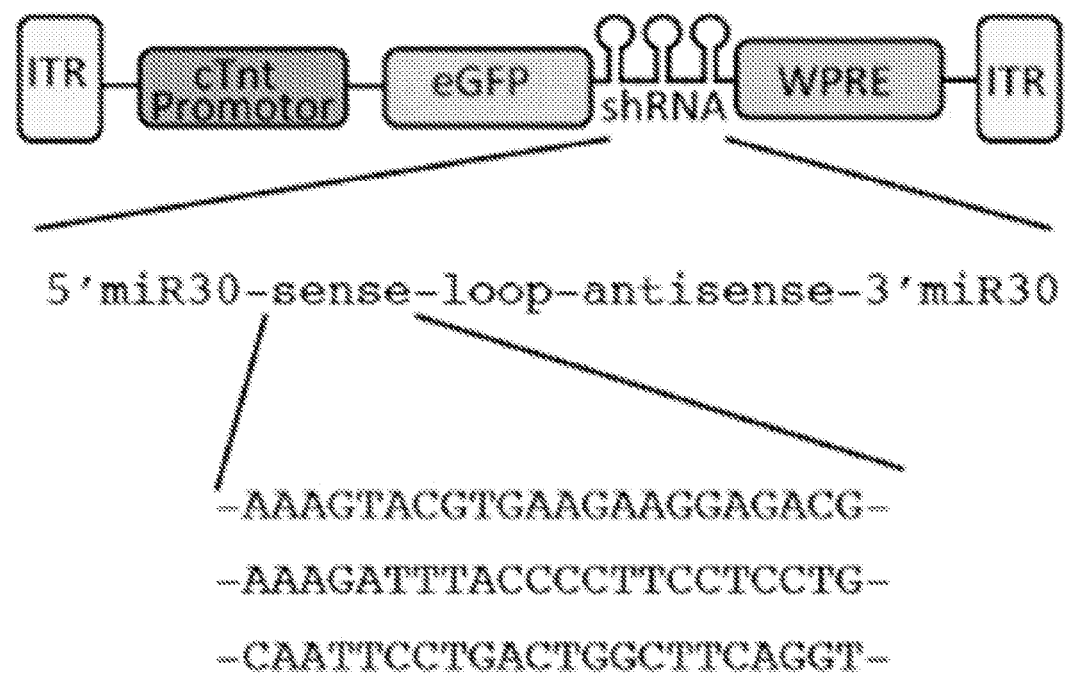
Figure 4J:
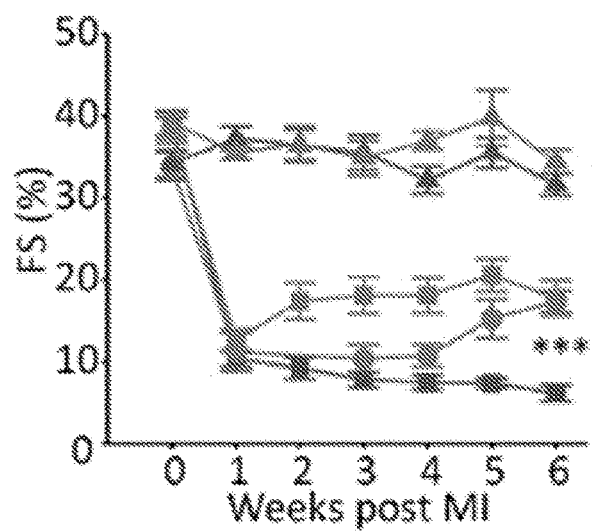
Figure 4K:
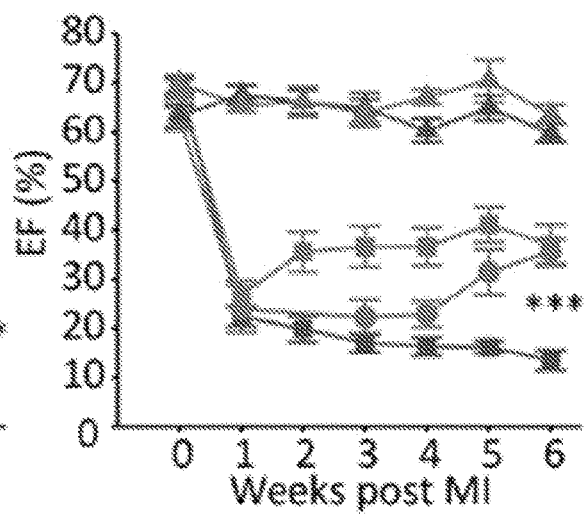
Figure 4L:
Figure 4M:
Figure 4N:
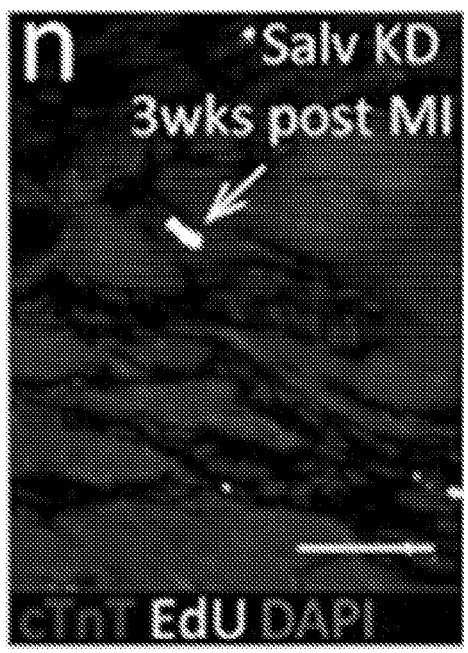
Figure 4O:
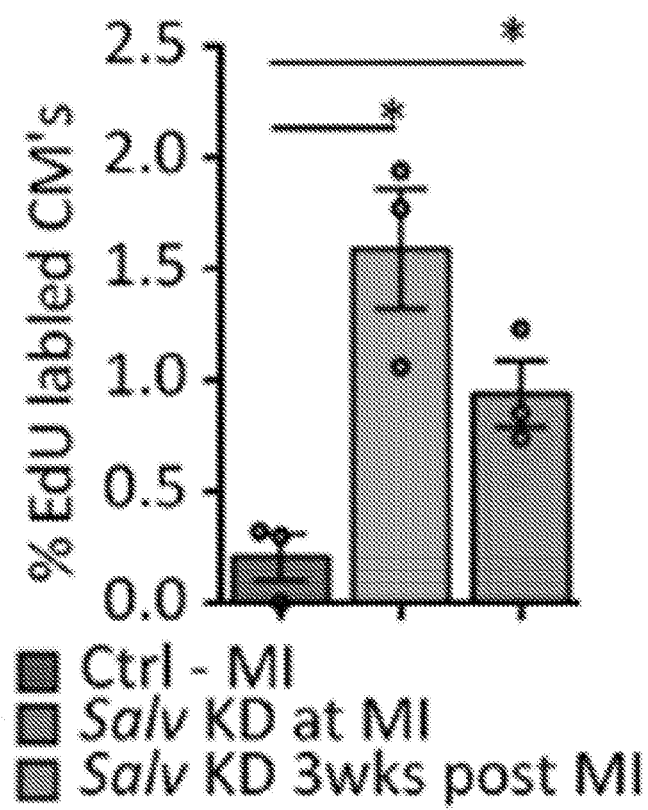

The inventors engineered a viral vector to knockdown Salv in cardiomyocytes (FIGS. 4h, 4i). Direct myocardial viral injection at the time of myocardial infarction or systemic viral injection 3 weeks after myocardial infarction resulted in improved cardiac function and cell cycle induction (FIGS. 4j-4o). Hippo pathway inhibition, genetically or with gene therapy, results in an effective stress response in ischaemic heart failure with organ failure reversal.

Because Hippo signalling is upregulated in human ischaemic heart failure, Hippo pathway inhibition may have a therapeutic benefit for patients with ischaemic heart failure. The inventors identified cardiomyocyte-directed, non-cell-autonomous injury responses that improve vascular perfusion. New cardiomyocytes, derived from pre-existing cardiomyocytes, direct recovery of a border zone microvasculature by expressing vessel-promoting factors including fibroblast growth factors that are protective against cardiac damage (Itoh et al., 2016; Korf-Klingebiel et al., 2011; Singla et al., 2015). Reversal of ischaemic heart failure requires a proliferative response and injury resistance because newly generated cardiomyocytes must withstand both mechanical and hypoxic stress. At-risk cardiomyocytes also probably benefit from Hippo pathway inhibition.

The data provide insight into Park2 function in cardiac regeneration. In addition to mitochondrial quality control, Park2 functions in mitochondrial maturation and in fetal-to-adult metabolic transition (Gong et al., 2015). Park2 is essential for neonatal regeneration and for cardiac repair in non-regenerative P8 SalvCKO hearts and in ischaemic heart failure. In P8 SalvCKO hearts, Park2 deletion was detrimental to cardiac function, but dispensable for fibrosis resolution. In contrast, in adult ischaemic heart failure, both cardiac function and fibrosis resolution were impaired in SalvCKO;Park2$^{-/-}$ mice.

Example 2

Examples of Materials and Methods

Patient Samples

Three types of human heart tissue were used for this study: control samples (non-failing, non-transplantable hearts, n=6), heart failure samples (hearts with non-ischaemic idiopathic cardiomyopathy in end-stage failure, n=3), and ischaemic heart failure samples (hearts with ischaemic heart disease in end-stage failure, n=3). For the control and both types of heart failure, samples were obtained from the left ventricular apex. The heart failure samples were collected at the time of implantation of a left ventricular assist device, the area from which the tissue core is obtained. The tissue samples were provided by the Texas Heart Institute Center for Cardiac Support Cardiovascular Surgery Research and Cardiovascular Pathology Research in accordance with human research protocol approved by the Texas Heart Institute Institutional Review Board under which patient informed consent was obtained. Sample analysis was conducted in accordance with human research protocol approved by the Baylor College of Medicine Institutional Review Board for which additional patient consent was waived. The tissue samples were digested to obtain protein lysates with the following buffer: 50 mM Tris-Cl (pH 7.5), 150 mM NaCl, 1% Triton X-100, 0.25% sodium deoxycholate, and protease/phosphatase inhibitors. Samples were homogenized with a Dounce tissue homogenizer, passed through a 22-gauge needle, and sonicated for ten cycles (30 s on, 30 s off) in a Diagenode Bioruptor Pico Plus NGS. For western blot analysis, we used antibodies against total YAP (Novus NB110-58358), pYAP (Cell Signaling 4911S), pLats1 (Cell Signaling 9157), Sav1 (Novus NBP2-13282), Park2 (Cell Signaling 2132S), and α-tubulin (Sigma T5168).

Mice

Adult C57/BL6×129/S mice, 8-10 weeks old, were used for the heart failure studies, and underwent either a sham procedure or a myocardial infarction procedure. C57/BL6 and 129/S strains are weakly regenerative[30]. For the AAV9 experiments, adult (8-10 weeks old) ICR (CD1) mice were used. The regenerative characteristics of outbred ICR (CD1) compared with inbred strains has not been systematically investigated. At 3 weeks after myocardial infarction, the inventors injected tamoxifen into mice to induce Cre activity in cardiomyocytes. Control mice included tamoxifen-injected αMHC-mcm; ROSA$^{mT/mG}$ (mTmG) mice, tamoxifen-injected Salv$^{fl/fl}$ mice, and oil-injected αMHC-mcm; and Salv$^{fl/fl}$ mice to control for tamoxifen and Cre recombinase cardiotoxicity[31-33]. SalvCKO mice included tamoxifen-injected αMHC-mcm; ROSA$^{mT/mG}$; Salv$^{fl/fl}$ mice and tamoxifen-injected αMHC-mcm; and Salv$^{fl/fl}$ mice. The ROSA$^{mT/mG}$ reporter was used to linage trace αMHC-mcm cardiomyocytes. Tamoxifen-injected αMHC-mcm; Rpl22$^{HA}$ mice were used as controls for TRAP experiments. For experiments involving TRAP SalvCKO mice, the inventors used tamoxifen-injected αMHC-mcm; Salv$^{fl/fl}$; and Rpl22$^{HA}$ mice. For the P1 Park2 experiments, the inventors used C57BL/6J and Park2$^{tm1shm/j}$ mice. For the P8 and adult double-mutant experiments, the inventors used αMHC-mcm; Salv$^{fl/fl}$; and Park2$^{tm1shm/j}$ mice injected with tamoxifen.

To achieve recombination of floxed alleles in the adult mice, tamoxifen dissolved in peanut oil was administered via intraperitoneal injection at a dose of 1 mg per day for 4 days beginning 3 weeks after myocardial infarction. No tamoxifen was administered to the mice in the P1 experiments. To achieve recombination of the floxed alleles in the P8 mouse experiments, tamoxifen was administered at P7, P8, P9, and P10, at 0.5 mg per day dissolved in peanut oil, as previously described[8].

All mouse procedures were performed in accordance with institutional and governmental guidelines, and approved by the Baylor College of Medicine Institutional Animal Care and Use Committee.

Model of heart failure in adult mice. To induce myocardial infarction in 8- to 10-week-old mice, the inventors permanently ligated the left anterior descending artery as previously described[8]. Briefly, mice were anaesthetized with 2% isoflurane and then intubated. The inventors exposed the heart by performing a thoracotomy through the fourth or fifth intercostal space and tied an 8-0 nylon suture around the left anterior descending artery. The mice were allowed to recover for 3 weeks, and then heart function was analysed by using echocardiography. Because the clinical definition of heart failure is a 20% reduction in left ventricular ejection fraction as indicated on echocardiography (that is, from >50% ejection fraction to <40% ejection fraction in humans) (Sam et al., 2000) only mice with >20% decrease in left ventricular ejection fraction were included in the study (Gao et al., 2000). The observed rates of survival (64%) and inclusion (70%) were consistent with those previously reported (50-60% and 54-92%, respectively) (Gao et al,. 2000; Sam et al., 2000; Wang et al., 2006).

Model of myocardial infarction in early and late neonatal mice. To induce myocardial infarction in neonatal mice, we permanently ligated the left anterior descending artery on P1 or P8, as previously described (Heallen et al., 2013). Briefly, mice were anaesthetized with hypothermia, the heart was exposed via thoracotomy through the fourth or fifth intercostal space, and an 8-0 nylon suture was tied around the left anterior descending coronary artery.

Echocardiography

Cardiac function was determined by echocardiography (VisualSonics, Vevo 2100, 40 MHz 550S probe). After alignment in the transverse B-mode with the papillary muscles, cardiac function was measured on M-mode images.

Injury Regions

Cardiac tissue regions used for RNA or image characterization are described as whole heart, ischaemic zone (left ventricle free wall), border zone (left ventricle anterior and posterior walls), or distal zone (interventricular septum).

Histological Analysis

Whole hearts were fixed with 10% formalin, embedded in paraffin, and sectioned at 7-μm intervals. Each slide had 10 sections, which started at the apex and ended at the suture ligation site (approximately 50 slides). Every fourth slide was stained with Masson's trichrome to identify areas of fibrosis. To determine scar size, the inventors examined serial sections from the apex to the ligation suture site and calculated the average percentage fibrosis of the midline circumference around the left ventricle (Nascimento et al., 2011). To quantify cardiomyocytes, we used PCM-1 immunostaining and methods as described (Bergmann et al., 2015).

Immunofluorescence Experiments

To assess cell cycle entry, the inventors added thymidine analogues to the drinking water for a duration of 4 days before dissection. The analogue 5-iodo-2'-deoxyuridine (IdU; 0.2 g l$^{-1}$, MP Biomedical, 0210035701) was used at the time point of 3 weeks after myocardial infarction before tamoxifen delivery. The analogue EdU (0.2 g l$^{-1}$, Santa Cruz, sc-284628A) was used for the time points at 4, 6, and 9 weeks after myocardial infarction. Immunofluorescence experiments were performed on formalin-fixed and paraffin-embedded sections or on fresh frozen optimum cutting temperature-embedded sections. The stains and antibodies used for these experiments included a Click-iT EdU kit, IdU staining (IdU cross-reactive BrdU antibody, BD Biosciences, 347580), mTmG lineage trace (endogenous mTomato and mGFP fluorescence), isolectin B4 (Vector Labs, FL-1201), CD31 antibody (Pecam, BD Pharmingen, 550274), PCM1 (Sigma, HPA023370), cTnT (ThermoFisher, MS295), wheat germ agglutinin (WGA, Vector Labs, RL-1022), and pH H3 (Cell Signaling, 9701).

Linage tracing was done using the Rosa26$^{mT/mG}$ reporter at 4 and 9 weeks after myocardial infarction in the border zone. A full dose of tamoxifen was administered, and mosaicism of the reporter was observed in the border zone. Mosaicism was not observed in the distal zone. We assumed this was because of the variability of drug-included Cre activity because of the poor border zone vascularity. The time point at 4 weeks after myocardial infarction was used as a baseline to determine Cre activity in the border zone.

RNA

Total RNA. Using trizol reagent, the inventors isolated total RNA from the non-fibrotic myocardium (interventricular septum, anterior and posterior free wall) below the ligation suture.

TRAP RNA. The TRAP method utilizes an inducible haemagglutinin (HA) epitope-tagged ribosomal allele for the Cre-mediated cell-specific isolation of RNA (SAnz et al., 2009). By crossing this allele into the SalvCKO background and then performing TRAP-seq, the inventors enriched mRNAs that were loaded onto ribosomes in cardiomyocytes and determined the cardiomyocyte translating RNA profile. The inventors quickly excised the whole heart from each mouse and obtained the left ventricle anterior and posterior free walls (the myocardial border zone) below the ligation suture to isolate ribosomal-associated cardiomyocyte-specific RNA. The tissue was homogenized on ice in 1 ml of supplemented homogenization buffer (1% NP-40, 0.1 M KCl, 0.05 M Tris, 0.012 M MgCl$_2$, 0.1 mg ml$^{-1}$ cyclohexamide, protease inhibitors, RNAsin, 0.01 M DTT). The samples were centrifuged, and the supernatants were incubated at 4° C. for 4 h with the primary HA-antibody (Cell Signaling, 3724) and then overnight with protein-G magnetic beads (Pierce, 88847). Bead-antibody RNA isolation was performed on the homogenate, which was washed with a high-salt buffer (1% NP-40, 0.3 M KCl, 0.05 M Tris, 0.012 M MgCl$_2$, 0.1 mg cyclohexamide, 0.01 M DTT). In samples with no expression of the Rpl22$^{HA}$ transgene, we recovered less than 1% of the total input RNA; therefore, the inventors assumed that the RNA isolation was highly specific.

Quantitative PCR. Transcript levels were quantified by using qPCR. First-strand synthesis was performed by using iScript reverse transcription super mix for qPCR (BioRad, 1708841); then, qPCR was performed by using iTaq Universal SYBR Green super mix (BioRad, 172-5121). All qPCR primers, merely as examples, are listed in Supplementary Table 1.

| Supplementary Table 1; qPCR primers | |
|---|---|
| Angpt1 Forward | GAGGATTGAGCTGATGGACTG |
| Angpt1 Reverse | ACCGTGTAAGATCAAGCTGC |
| Angpt2 Forward | GCTGGTGAAGAGTCCAACTAC |

Supplementary Table 1; qPCR primers

| | |
|---|---|
| Angpt2 Reverse | GATGCTACTTATTTTGCCCGC |
| Fgf14 Forward | ACAAGAACCCAACTGATCCC |
| Fgf14 Reverse | ACTGGGATGAGGTTGAACAG |
| Fgf18 Forward | CAAGGGCAAGGAGACAGAAT |
| Fgf18 Reverse | GTACTTGGCAGACATCAGGG |
| GapDH Forward | CTTTGTCAAGCTCATTTCCTGG |
| GapDH Reverse | TCTTGCTCAGTGTCCTTGC |
| Myh6 Forward | GCTTCAGCTGGAAGAAAAGCTC |
| Myh6 Reverse | CCTCCTCCAGCTCCTCGAT |
| Myh7 Forward | CAAGCAGCAGTTGGATGAGC |
| Myh7 Reverse | CGTGCCTGAAGCTCCTTGA |
| Nppa Forward | GTGCGGTGTCCAACACAGAT |
| Nppa Reverse | CCCTGCTTCCTCAGTCTGCT |
| Nppb Forward | GGACCAAGGCCTCACAAAAG |
| Nppb Reverse | TACAGCCCAAACGACTGACG |
| Vegfa Forward | GGCAGCTTGAGTTAAACGAAC |
| Vegfa Reverse | TGGTGACATGGTTAATCGGTC |
| Vegfb Forward | GCAACACCAAGTCCGAATG |
| Vegfb Reverse | GTATGGCAACCCTGTCTGG |
| Salv Forward | GCTTCTGGAGATGGTGTAGTTT |
| Salv Reverse | CAGTCTGTGGCTTTCTCTTCTC |

(from top to bottom of Supplementary Table 1, the sequences are identified by SEQ ID NO:1 through SEQ ID NO:24).

RNA-seq library preparation and data analysis. To isolate mRNA from total RNA and TRAP RNA samples, the inventors used a Dynabeads mRNA DIRECT Micro kit. ERCC Ex Fold RNA Spike-In control mixes were added before mRNA purification. Ion torrent RNA-seq libraries were prepared with an Ion Total RNA-seq kit v2 for whole-transcriptome libraries. RNA sequencing was performed by using the Ion Proton system for next-generation sequencing. Reads were mapped to the mouse genome (mm10) and read counts quantified using STAR (version 2.5). Differentially expressed genes were detected using R package DESeq2 with the following parameters: threshold P≤0.05, fold change≥0.5, and false detection rate≤10%. GO analysis was performed on differentially expressed genes (P<0.05) with the Metascape online platform, and annotation clusters with terms that had P≤0.05 were included.

The inventors compared their TRAP versus total RNA analysis with the cardiomyocyte and non-cardiomyocyte isolation data set (GSE49906) (Giudice et al., 2014). When sorted by fold change, the top 400 cardiomyocyte-enriched genes extracted from the GSE49906 P60 mouse hearts were on average 1.5-fold more highly expressed in TRAP-seq samples than in total-RNA-seq samples. Likewise, the top 400 non-cardiomyocyte enriched genes were on average 1.5-fold more highly expressed in the total-RNA-seq data.

AAV9 Targeting Salv

First, three siRNA constructs targeting Salv were tested in vitro in primary isolated neonatal mouse cardiomyocytes. Then, a triple short hairpin (sh)RNA construct with flanking miR30 sequences was cloned into the pENN.AAV.cTNT, p1967-Q vector downstream of GFP. Expression of both the GFP and the shRNA is driven by the cardiac troponin T promotor. The miR30-based shRNA design allows for efficient shRNA expression from an RNA Pol II promoter (Dow et al., 2012). The resulting construct was packaged into the muscle-trophic serotype AAV9 by the Intellectual and Developmental Disabilities Research Center Neuroconnectivity Core at Baylor College of Medicine. Two methods of viral delivery were used: direct myocardial injection at the time of myocardial infarction or systemic injection by retro-orbital injection 3 weeks after myocardial infarction. Viral titre for efficient knockdown was performed as described previously and shown to effectively knockdown Salv (Dow et al., 2012). For direct myocardial injection at the time of myocardial infarction, the mice were given two or three intra-myocardial injections by Hamilton syringe (50 µl capacity) with a 33-gauge needle to deliver a total of $2\times10^{11}$ viral genomes (10 µl total volume delivered) into the ischaemic risk area. In a separate cohort of mice, AAV9 was injected systemically by retro-orbital injection to deliver a total of $1\times10^{12}$ viral genomes (50 µl total volume delivered).

Statistical Analysis

Throughout this study, the inventors used either the Mann-Whitney U-test or analysis of variance (ANOVA) with Tukey's pairwise post-hoc test or Bonferroni's post-hoc test to compare means and an F-test to compare variance. All error bars show the s.e.m. mice were assigned unique identifiers to blind experimenters to genotypes. A block randomization scheme was used to assign animals to groups on a rolling admissions basis to obtain adequate samples for each time point and each experiment. For echocardiography, sample sizes were estimated using power analysis determined from our previously described experiments.

REFERENCES

All patents and publications mentioned in the specification are indicative of the level of those skilled in the art to which the invention pertains. All patents and publications are herein incorporated by reference to the same extent as if each individual publication was specifically and individually indicated to be incorporated by reference.

Bergmann, O. et al. Dynamics of cell generation and turnover in the human heart. Cell 161, 1566-1575 (2015).

Bersell, K. et al. Moderate and high amounts of tamoxifen in ☐MHC-MerCreMer mice induce a DNA damage response, leading to heart failure and death. Dis. Model. Mech. 6, 1459-1469 (2013).

Birks, E. J. Molecular changes after left ventricular assist device support for heart failure. Circ. Res. 113, 777-791 (2013).

Braunwald, E. Heart failure. JACC Heart Fail. 1, 1-20 (2013).

Del Re, D. P. et al. Mst1 promotes cardiac myocyte apoptosis through phosphorylation and inhibition of Bcl-xL. Mol. Cell 54, 639-650 (2014).

Dorn, G. W., II. Parkin-dependent mitophagy in the heart. J. Mol. Cell. Cardiol. 95, 42-49 (2016).

Doupé, D. P. et al. A single progenitor population switches behavior to maintain and repair esophageal epithelium. Science 337, 1091-1093 (2012).

Dow, L. E. et al. A pipeline for the generation of shRNA transgenic mice. *Nat. Protocols* 7, 374-393 (2012).

Gao, X. M., Dart, A. M., Dewar, E., Jennings, G. & Du, X. J. Serial echocardiographic assessment of left ventricular dimensions and function after myocardial infarction in mice. *Cardiovasc. Res.* 45, 330-338 (2000).

Giudice, J. et al. Alternative splicing regulates vesicular trafficking genes in cardiomyocytes during postnatal heart development. *Nat. Commun.* 5, 3603 (2014).

Gong, G. et al. Parkin-mediated mitophagy directs perinatal cardiac metabolic maturation in mice. *Science* 350, aad2459 (2015).

Halder, G. & Johnson, R. L. Hippo signaling: growth control and beyond. *Development* 138, 9-22 (2011).

Halder, G., Dupont, S. & Piccolo, S. Transduction of mechanical and cytoskeletal cues by YAP and TAZ. *Nat. Rev. Mol. Cell Biol.* 13, 591-600 (2012).

Heallen, T. et al. Hippo signaling impedes adult heart regeneration. *Development* 140, 4683-4690 (2013).

Heineke, J. & Molkentin, J. D. Regulation of cardiac hypertrophy by intracellular signalling pathways. *Nat. Rev. Mol. Cell Biol.* 7, 589-600 (2006).

Itoh, N., Ohta, H., Nakayama, Y. & Konishi, M. Roles of FGF signals in heart development, health, and disease. *Front. Cell Dev. Biol.* 4, 110 (2016).

Jessup, M. & Brozena, S. Heart failure. *N. Engl. J. Med.* 348, 2007-2018 (2003).

Kim, S. Y., Morales, C. R., Gillette, T. G. & Hill, J. A. Epigenetic regulation in heart failure. *Curr. Opin. Cardiol.* 31, 255-265 (2016).

Koitabashi, N. et al. Avoidance of transient cardiomyopathy in cardiomyocyte-targeted tamoxifen-induced MerCreMer gene deletion models. *Circ. Res.* 105, 12-15 (2009).

Korf-Klingebiel, M. et al. Conditional transgenic expression of fibroblast growth factor 9 in the adult mouse heart reduces heart failure mortality after myocardial infarction. *Circulation* 123, 504-514 (2011).

Kostin, S., Hein, S., Arnon, E., Scholz, D. & Schaper, J. The cytoskeleton and related proteins in the human failing heart. *Heart Fail. Rev.* 5, 271-280 (2000).

Kubli, D. A. et al. Parkin protein deficiency exacerbates cardiac injury and reduces survival following myocardial infarction. *J. Biol. Chem.* 288, 915-926 (2013).

Leask, A. Getting to the heart of the matter: new insights into cardiac fibrosis. *Circ. Res.* 116, 1269-1276 (2015).

Lenneman, A. J. & Birks, E. J. Treatment strategies for myocardial recovery in heart failure. *Curr. Treat. Options Cardiovasc. Med.* 16, 287 (2014).

Loehr, L. R., Rosamond, W. D., Chang, P. P., Folsom, A. R. & Chambless, L. E. Heart failure incidence and survival (from the Atherosclerosis Risk in Communities study). *Am. J. Cardiol.* 101, 1016-1022 (2008).

Lopez, A. D., Mathers, C. D., Ezzati, M., Jamison, D. T. & Murray, C. J. Global and regional burden of disease and risk factors, 2001: systematic analysis of population health data. *Lancet* 367, 1747-1757 (2006).

Marín-García, J. & Akhmedov, A. T. Mitochondrial dynamics and cell death in heart failure. *Heart Fail. Rev.* 21, 123-136 (2016).

Matsuda, T. et al. NF2 activates Hippo signaling and promotes ischemia/reperfusion injury in the heart. *Circ. Res.* 119, 596-606 (2016).

Meredith, A. J. et al. Circulating biomarker responses to medical management vs. mechanical circulatory support in severe inotrope-dependent acute heart failure. *ESC Heart Fail.* 3, 86-96 (2016).

Morikawa, Y., Heallen, T., Leach, J., Xiao, Y. & Martin, J. F. Dystrophin-glycoprotein complex sequesters Yap to inhibit cardiomyocyte proliferation. *Nature* 547, 227-231 (2017).

Morikawa, Y. et al. Actin cytoskeletal remodeling with protrusion formation is essential for heart regeneration in Hippo-deficient mice. *Sci. Signal.* 8, ra41 (2015).

Nascimento, D. S. et al. MIQuant—semi-automation of infarct size assessment in models of cardiac ischemic injury. *PLoS ONE* 6, e25045 (2011).

Patterson, M. et al. Frequency of mononuclear diploid cardiomyocytes underlies natural variation in heart regeneration. *Nat. Genet.* 49, 1346-1353 (2017).

Pontén, A., Folestad, E. B., Pietras, K. & Eriksson, U. Platelet-derived growth factor D induces cardiac fibrosis and proliferation of vascular smooth muscle cells in heart-specific transgenic mice. *Circ. Res.* 97, 1036-1045 (2005).

Pugach, E. K., Richmond, P. A., Azofeifa, J. G., Dowell, R. D. & Leinwand, L. A. Prolonged Cre expression driven by the a-myosin heavy chain promoter can be cardiotoxic. *J. Mol. Cell. Cardiol.* 86, 54-61 (2015).

Singla, D. K., Singla, R. D., Abdelli, L. S. & Glass, C. Fibroblast growth factor-9 enhances M2 macrophage differentiation and attenuates adverse cardiac remodeling in the infarcted diabetic heart. *PLoS ONE* 10, e0120739 (2015).

Sam, F. et al. Progressive left ventricular remodeling and apoptosis late after myocardial infarction in mouse heart. *Am. J. Physiol. Heart Circ. Physiol.* 279, H422-H428 (2000).

Sanz, E. et al. Cell-type-specific isolation of ribosome-associated mRNA from complex tissues. *Proc. Natl Acad. Sci. USA* 106, 13939-13944 (2009).

Tao, G. et al. Pitx2 promotes heart repair by activating the antioxidant response after cardiac injury. *Nature* 534, 119-123 (2016).

Wang, J. et al. A simple and fast experimental model of myocardial infarction in the mouse. *Tex. Heart Inst. J.* 33, 290-293 (2006).

Xin, M. et al. Hippo pathway effector Yap promotes cardiac regeneration. *Proc. Natl Acad. Sci. USA* 110, 13839-13844 (2013).

Although the present disclosure and its advantages have been described in detail, it should be understood that various changes, substitutions and alterations can be made herein without departing from the spirit and scope of the design as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the present disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A method of treating an individual for heart failure, the method comprising administering to the individual an effective amount of a Park2 nucleic acid encoding a polypeptide comprising SEQ ID NO: 25, and an effective amount of an shRNA that targets Salvador, wherein the shRNA comprises a sequence selected from the group consisting of SEQ ID NO: 27, SEQ ID NO: 28, and SEQ ID NO: 29.

2. The method of claim 1, wherein the Park2 nucleic acid is administered to the individual more than once.

3. The method of claim 1, wherein the Park2 nucleic acid is administered to the individual systemically.

4. The method of claim 1, wherein the Park2 nucleic acid is administered locally to the heart of the individual.

5. The method of claim 1, wherein the individual is provided an additional therapy for the heart failure.

6. The method of claim 1, wherein the shRNA is administered to the individual more than once.

7. The method of claim 1, wherein the shRNA is administered to the individual systemically.

8. The method of claim 1, wherein the shRNA is administered locally to the heart of the individual.

9. The method of claim 1, wherein the heart failure is ischemic heart failure.

* * * * *

SEQUENCE LISTING

<160> NUMBER OF SEQ ID NOS: 38

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gaggattgag ctgatggact g                                              21

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
accgtgtaag atcaagctgc                                                20

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gctggtgaag agtccaacta c                                              21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gatgctactt attttgcccg c                                              21

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
acaagaaccc aactgatccc                                                20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
actgggatga ggttgaacag                                                20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
caagggcaag gagacagaat                                              20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gtacttggca gacatcaggg                                              20

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ctttgtcaag ctcatttcct gg                                           22

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tcttgctcag tgtccttgc                                               19

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gcttcagctg gaagaaaagc tc                                           22

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cctcctccag ctcctcgat                                               19

```
<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
caagcagcag ttggatgagc                                                 20

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cgtgcctgaa gctccttga                                                  19

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gtgcggtgtc caacacagat                                                 20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ccctgcttcc tcagtctgct                                                 20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ggaccaaggc ctcacaaaag                                                 20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tacagcccaa acgactgacg                                                 20
```

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ggcagcttga gttaaacgaa c                                              21

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tggtgacatg gttaatcggt c                                              21

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gcaacaccaa gtccgaatg                                                 19

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gtatggcaac cctgtctgg                                                 19

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gcttctggag atggtgtagt tt                                             22

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
cagtctgtgg ctttctcttc tc                                             22

<210> SEQ ID NO 25

<211> LENGTH: 387
<212> TYPE: PRT
<213> ORGANISM: Homo sapiens

<400> SEQUENCE: 25

```
Met Ile Val Phe Val Arg Phe Asn Ser Ser His Gly Phe Pro Val Glu
1               5                   10                  15

Val Asp Ser Asp Thr Ser Ile Phe Gln Leu Lys Glu Val Val Ala Lys
            20                  25                  30

Arg Gln Gly Val Pro Ala Asp Gln Leu Arg Val Ile Phe Ala Gly Lys
        35                  40                  45

Glu Leu Arg Asn Asp Trp Thr Val Gln Asn Cys Asp Leu Asp Gln Gln
50                  55                  60

Ser Ile Val His Ile Val Gln Arg Pro Trp Arg Lys Gly Gln Glu Met
65                  70                  75                  80

Asn Ala Thr Gly Gly Asp Pro Arg Asn Ala Ala Gly Gly Cys Glu
                85                  90                  95

Arg Glu Pro Gln Ser Leu Thr Arg Val Asp Leu Ser Ser Ser Val Leu
            100                 105                 110

Pro Gly Asp Ser Val Gly Leu Ala Val Ile Leu His Thr Asp Ser Arg
        115                 120                 125

Lys Asp Ser Pro Pro Ala Gly Ser Pro Ala Gly Arg Ser Ile Tyr Asn
130                 135                 140

Ser Phe Tyr Val Tyr Cys Lys Gly Pro Cys Gln Arg Val Gln Pro Gly
145                 150                 155                 160

Lys Leu Arg Val Gln Cys Ser Thr Cys Arg Gln Ala Thr Leu Thr Leu
            165                 170                 175

Thr Gln Gly Pro Ser Cys Trp Asp Asp Val Leu Ile Pro Asn Arg Met
        180                 185                 190

Ser Gly Glu Cys Gln Ser Pro His Cys Pro Gly Thr Ser Ala Glu Phe
    195                 200                 205

Phe Phe Lys Cys Gly Ala His Pro Thr Ser Asp Lys Glu Thr Ser Val
210                 215                 220

Ala Leu His Leu Ile Ala Thr Asn Ser Arg Asn Ile Thr Cys Ile Thr
225                 230                 235                 240

Cys Thr Asp Val Arg Ser Pro Val Leu Val Phe Gln Cys Asn Ser Arg
            245                 250                 255

His Val Ile Cys Leu Asp Cys Phe His Leu Tyr Cys Val Thr Arg Leu
        260                 265                 270

Asn Asp Arg Gln Phe Val His Asp Pro Gln Leu Gly Tyr Ser Leu Pro
    275                 280                 285

Cys Val Gly Thr Gly Asp Thr Val Val Leu Arg Gly Ala Leu Gly Gly
290                 295                 300

Phe Arg Arg Gly Val Ala Gly Cys Pro Asn Ser Leu Ile Lys Glu Leu
305                 310                 315                 320

His His Phe Arg Ile Leu Gly Glu Glu Gln Tyr Asn Arg Tyr Gln Gln
            325                 330                 335

Tyr Gly Ala Glu Glu Cys Val Leu Gln Met Gly Gly Val Leu Cys Pro
        340                 345                 350

Arg Pro Gly Cys Gly Ala Gly Leu Leu Pro Glu Pro Asp Gln Arg Lys
    355                 360                 365

Val Thr Cys Glu Gly Gly Asn Gly Leu Gly Cys Gly Tyr Gly Gln Arg
370                 375                 380

Arg Thr Lys
```

<210> SEQ ID NO 26
<211> LENGTH: 1575
<212> TYPE: DNA
<213> ORGANISM: Homo sapiens

<400> SEQUENCE: 26

```
gggatttaac ccaggagagc cgctggtggg aggcgcggct ggcgccgctg cgcgcatggg    60
cctgttcctg gcccgcagcc gccacctacc cagtgaccat gatagtgttt gtcaggttca   120
actccagcca tggtttccca gtggaggtcg attctgacac cagcatcttc cagctcaagg   180
aggtggttgc taagcgacag ggggttccgg ctgaccagtt gcgtgtgatt ttcgcaggga   240
aggagctgag gaatgactgg actgtgcaga attgtgacct ggatcagcag agcattgttc   300
acattgtgca gagaccgtgg agaaaaggtc aagaaatgaa tgcaactgga ggcgacgacc   360
ccagaaacgc ggcgggaggc tgtgagcggg agccccagag cttgactcgg gtggacctca   420
gcagctcagt cctcccagga gactctgtgg ggctggctgt cattctgcac actgacagca   480
ggaaggactc accaccagct ggaagtccag caggtagatc aatctacaac agcttttatg   540
tgtattgtaa aggcccctgt caaagagtgc agccggggaa actcagggta cagtgcagca   600
cctgcaggca ggcaacgctc accttgaccc agggtccatc ttgctgggat gatgttttaa   660
ttccaaaccg gatgagtggt gaatgccaat ccccacactg ccctgggact agtgcagaat   720
ttttctttaa atgtggagca caccccacct ctgacaagga acatcagta gctttgcacc   780
tgatcgcaac aaatagtcgg aacatcactt gcattacgtg cacagacgtc aggagccccg   840
tcctggtttt ccagtgcaac tcccgccacg tgatttgctt agactgtttc cacttatact   900
gtgtgacaag actcaatgat cggcagtttg ttcacgaccc tcaacttggc tactccctgc   960
cttgtgtggg aactggagac acagtggtgc ttagaggagc tctgggggga ttcaggagag  1020
gagtcgctgc ctgtcccaac tccttgatta aagagctcca tcacttcagg attctgggag  1080
aagagcagta caaccggtac cagcagtatg gtgcagagga gtgtgtcctg cagatggggg  1140
gcgtgttatg cccccgccct ggctgtggag cggggctgct gccggagcct gaccaggaga  1200
aagtcacctg cgaaggggc aatggcctgg gctgtgggta tggacaacga agaacaaaat  1260
aagctgcctc agggagaagt gagtgcctca ttcaatacat cgttcaagga aaagtcattg  1320
gtagcaaagc tatagaagaa ttacagagtt ccagatgtgg aaaaagccct agacgtcatt  1380
aactccagtg attatcagga tgtggttcac agatttattg taagatgcct gtgaattcac  1440
ccgtgcttaa tttttttttc cctcaattat caagataaa aaagtacaac tcttaccatg  1500
tgggtatgca agaaatgtta gctgttacaa aaaaaatcgc gtataaaaaa gttgaaaacc  1560
aaataaaaaa aaaaa                                                   1575
```

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 27

```
aagtacgtga agaaggagac g                                              21
```

<210> SEQ ID NO 28

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
aagatttacc ccttcctcct g                                              21

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
attcctgact ggcttcaggt                                                20

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
aagtacgtga agaaggagac g                                              21

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
aagatttacc ccttcctcct g                                              21

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
attcctgact ggcttcaggt                                                20

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
aagtacgtga agaaggagac g                                              21

<210> SEQ ID NO 34
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
aagatttacc ccttcctcct g                                              21

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
attcctgact ggcttcaggt                                                20

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
aaagtacgtg aagaaggaga cg                                             22

<210> SEQ ID NO 37
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
aaagatttac cccttcctcc tg                                             22

<210> SEQ ID NO 38
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
caattcctga ctggcttcag gt                                             22
```